(12) United States Patent
Barg et al.

(10) Patent No.: US 11,839,195 B2
(45) Date of Patent: Dec. 12, 2023

(54) PARTHENOCARPIC TOMATO PLANTS WITH LOSS OF FUNCTION MUTATION IN AN AGL6 GENE AND METHODS OF PRODUCING SAME

(71) Applicant: The State of Isreal, Ministry of Agriculture & Rural Development, Agricultural Research Organization (ARO) (Volcani Center), Rishon-LeZion (IL)

(72) Inventors: Rivka Barg, Rehovot (IL); Yehiam Salts, Rehovot (IL); Chen Klap, Kfar-Saba (IL); Itzhak Arazi, Kiryat-Ono (IL); Ester Yeshayahou, Kfar-Saba (IL); Anthony Bolger, Aachen (DE); Sara Shabtai, Karmei Yosef (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 474 days.

(21) Appl. No.: 16/071,097

(22) PCT Filed: Jan. 19, 2017

(86) PCT No.: PCT/IL2017/050078
§ 371 (c)(1),
(2) Date: Jul. 19, 2018

(87) PCT Pub. No.: WO2017/125931
PCT Pub. Date: Jul. 27, 2017

(65) Prior Publication Data
US 2021/0037779 A1    Feb. 11, 2021

Related U.S. Application Data

(60) Provisional application No. 62/281,227, filed on Jan. 21, 2016.

(51) Int. Cl.
*A01H 6/82*     (2018.01)
*A01H 1/06*     (2006.01)
*A01H 5/08*     (2018.01)

(52) U.S. Cl.
CPC .............. *A01H 6/82* (2018.05); *A01H 1/06* (2013.01); *A01H 5/08* (2013.01); *A01H 6/825* (2018.05)

(58) Field of Classification Search
None
See application file for complete search history.

(56) References Cited

U.S. PATENT DOCUMENTS

| | | |
|---|---|---|
| 6,268,552 B1 | 7/2001 | Li |
| 2003/0217391 A1 | 11/2003 | Van Vliet |
| 2009/0089902 P1 | 4/2009 | Takeuchi |
| 2010/0146656 A1 | 6/2010 | De Haan et al. |
| 2017/0002376 A1 | 1/2017 | Fukuoka et al. |

FOREIGN PATENT DOCUMENTS

| | | |
|---|---|---|
| WO | WO 2012/087140 | 6/2012 |
| WO | WO 2017/125931 | 7/2017 |

OTHER PUBLICATIONS

Kataoka et al. Yield of parthenocarpic tomato, "MPK-1", under plastic film house without heating in winter. (2011) Journal of Japanese Society of Agricultural Technology Management; vol. 18; pp. 67-73 (Year: 2011).*
Takisawa et al. The parthenocarpic gene Pat-k is generated by a natural mutation of SlACL6 affecting fruit development in tomato (*Solanum lycopersicum*. (2018) BMC Plant Biology; vol. 18; pp. 1-12 (Year: 2018).*
Burton-Freeman et al. Whole food versus supplement: comparing the clinical evidence of tomato intake and lycopene supplementation on cardiovascular risk factors. (2014) Adv. Nutr.; vol. 5; pp. 457-485 (Year: 2014).*
Translation of Kataoka et al (2011) Journal of Japanese Society of Agricultural Technology Management; vol. 18; pp. 67-73; translation has no publication date available; pp. 1-24 (Year: NA).*
Saito et al. Mutant resources for the miniature tomato (*Solanum lycopersicum* L.) "Mictro-Tom" (2009) J. Japan. Soc. Hort. Sci; vol. 78; pp. 6-13 (Year: 2009).*
Office Action dated Jun. 28, 2020 From the Israel Patent Office Re. Application No. 260610 and its Translation Into English. (7 Pages).
Supplementary European Search Report and the European Search Opinion dated Jun. 4, 2019 From the European Patent Office Re. Application No. 17741188.1. (7 Pages).
Marti et al. "Silencing of DELLA Induces Facultative Parthenocarpy in Tomato Fruits", The Plant Journal, XP055359142, 52(5): 865-876, Published Online Sep. 19, 2007.
Notice of Reason(s) for Rejection dated Jun. 8, 2021 From the Japan Patent Office Re. Application No. 2018-537811 and its Translation Into English. (4 Pages).
Office Action dated Jul. 6, 2021 From the Israel Patent Office Re. Application No. 260610 and its Translation Into English. (7 Pages).
Communication Pursuant to Article 94(3) EPC dated Mar. 30, 2021 From the European Patent Office Re. Application No. 17741188.1. (5 Pages).

(Continued)

*Primary Examiner* — Cathy Kingdon Worley

(57) ABSTRACT

A tomato plant exhibiting a facultative parthenocarpy is provided. The plant comprises a loss-of-function mutation in a SlAGL6 gene and alternatively or additionally characterized by an average fruit weight/plant at least about the same as that of a non-parthenocarpic tomato of the same genetic background under fertilization permissive conditions of the non-parthenocarpic tomato. Also provided are methods of producing such plants and processed products produced from same.

11 Claims, 13 Drawing Sheets
(9 of 13 Drawing Sheet(s) Filed in Color)
Specification includes a Sequence Listing.

(56) References Cited

OTHER PUBLICATIONS

Notice of Reasons for Rejection dated Jan. 19, 2021 From the Japan Patent Office Re. Application No. 2018-537811 and its Translation Into English. (8 Pages).
Kataoka et al. "Yield of Parthenocarpic Tomato, 'MPK-1' Under Plastic Film House Without Heating in Winter", Journal of Japanese Society of Agricultural Technology Management, 18(2): 67-73, 2011.
Takisawa et al. "The Parthenocarpic Gene Pat-K is Generated by a Natural Mutation of SlAGL6 Affecting Fruit Development in Tomato (*Solanum lycopersicum* L.)", BMC Plant Biology, 18(1): 72-1-7212, Apr. 27, 2018.
Communication Pursuant to Article 94(3) EPC dated Sep. 2, 2020 From the European Patent Office Re. Application No. 17741188.1. (5 Pages).
International Preliminary Report on Patentability dated Aug. 2, 2018 From the International Bureau of WIPO Re. Application No. PCT/IL2017/050078. (8 Pages).
International Search Report and the Written Opinion dated Mar. 22, 2017 From the International Searching Authority Re. Application No. PCT/IL2017/050078. (13 Pages).
Ampomah-Dwamena et al. "Down-Regulation of TM29, a Tomato Sepallata Homolog, Cuases Parthenocarpic Fruit Development and Floral Reversion", Plant Physiology, 130(2): 605-617, Oct. 2002.
Duan et al. "Characterization of Osmads6-5, A Null Allele, Reveals That OsMADS6 is a Critical Regulator for Early Flower Development in Rice (*Oryza saliva* L.)", Plant Molecular Biology, 80(4-5): 429-442, Published Online Aug. 30, 2012.
Gaj et al. "ZFN, TALEN, and CRISPR/Cas-Based Methods for Genome Engineering", Trends in Biotechnology, 20: 1-9, Published Online May 9, 2013.
Gorguet et al. "Mapping and Characterization of Novel Parthenocarpy QTLs in Tomato", Theoretical and Applied Genetics, 116(6): 755-767, Published Online Jan. 30, 2008.
Gorguet et al. "Parthenocarpic Fruit Development in Tomato", Plant Biology, 7(2): 131-139, Mar. 21, 2005. p. 134, Left, Col., 1st Para, 4th Para.
Hosokawa et al. "Establishment of Plant Regeneration Method From Stem Apex Meristem for Strong Parthenocarpic Good Taste Tomato Varieties", Japanese Journal of Taste and Smell Research, 11(1): 61-68, Apr. 2004 and its Translation Into English.
Klap et al. "Tomato Facultative Parthenocarpy Results From Siagamous-Like 6 Loss of Function", Plant Biotechnology Journal, p. 1-14, Published Online Dec. 27, 2016.
Koo et al. "Control of Lateral Organ Development and Flowering Time by the *Arabidopsis thaliana* MADS-Box Gene Agamous-Like6", the Plant Journal, 62(5): 807-816, Published Online Mar. 23, 2010.
Mazzucato et al. "A Tilling Allele of the Tomato Aux/IAA9 Gene Offers New Insights Into Fruit Set Mechanisms and Perspectives for Breeding Seedless Tomatoes", Molecular Breeding, 35(1): 22-36, Published Online Jan. 20, 2015. Abstract, p. 30, Last Para—p. 31, right Col., 2nd Para, p. 33, Left Col., 2nd Para Right col., Last Para, Tables 1, 2.
Pan et al. "Functional Diversification of AGAMOUS Lineage Genes in Regulating Tomato Flower and Fruit Development", Journal of Experimental Botany, 61(6): 1795-1806, Advance Access Publication Mar. 24, 2010.
Pnueli et al. "Isolation of the Tomato AGAMOUS Gene TAG1 and Analysis of its Homeotic Role in Transgenic Plants", The Plant Cell, 6(2): 163-173, Feb. 1994.
Rijpkema et al. "The Petunia AGL6 Gene has a SEPALLATA-Like Function in Floral Patterning", The Plant Journal, 60(1): 1-9, Published Online Jun. 15, 2009.
The Gale Group "Fruits, Seedless", Plant Sciences, Encyclopedia. com: Free Online Encyclopedia, Definition, 1 P., Dec. 31, 2001. Last Para.
Wang et al. "Regulatory Features Underlying Pollination-Dependent and -Independent Tomato Fruit Set Revealed by Transcript and Primary Metabolite Profiling", The Plant Cell, 21(5): 1428-1452, Published Online May 12, 2009. p. 1446, Left col. 2nd Para, Figs.1b, 8, 15.
Yao et al. "Parthenocarpic Apple Fruit Production Conferred by Transposon Insertion Mutations in a MADS-Box Transcription Factor", Proc. Natl. Acad. Sci. USA, PNAS, 98(3): 1306-1311, Jan. 30, 2001.
Yi et al. "Differential Regulation of Lehsp23.8 in Tomato Plants: Analysis of a Multiple Stress-Inducible Promoter", Plant Science, 171(3): 398-407, Available Online May 26, 2006. Abstract, Figs.4-7.
Yoo et al. "AGAMOUS-Like 6 is a Floral Promoter That Negatively Regulates the FLC/MAF Clade Genes and Positively Regulates FT in *Arabidopsis*", The Plant Journal, 65(1): 62-76, Published Online Nov. 10, 2010.
Office Action dated Oct. 23, 2019 From the Israel Patent Office Re. Application No. 260610 and its Translation Into English. (6 Pages).
Notification of Office Action and Search Report dated Oct. 19, 2021 From the State Intellectual Property Office of the People's Republic of China Re. Application No. 201780018857.8 and its Translation Into English. (5 Pages).
Examen de Fondo [Examination Report] dated Sep. 28, 2022 From the Instituto Mexicano de la Propiedad Industrial, IMPI, Secretaria de Economía,Dirección Divisional de Patentes Re. Application No. MX/a/2018/008910 and its Translation Into English (12 Pages).
Search Report dated Sep. 9, 2022 from the National Institute of Industrial Property of Brazil Re. Application No. BR 11 2018 014902 0 with an English Translation. (6 pages).
Examination Report dated Mar. 1, 2022 From the Instituto Mexicano de la Propiedad Industrial, Direccion Divisional de Patentes Re. Application No. MX/a/2018/008910 and its Summary in English (9 Pages).
Notice of Reason(s) for Rejection dated Oct. 25, 2022 From the Japan Patent Office Re. Application No. 2021-165483 and its Translation Into English.(6 pages).
Notification of Office Action dated Jun. 15, 2022 From the State Intellectual Property Office of the People's Republic of China Re. Application No. 201780018857.8 and its Translation of Office Action Into English. (19 Pages).

\* cited by examiner

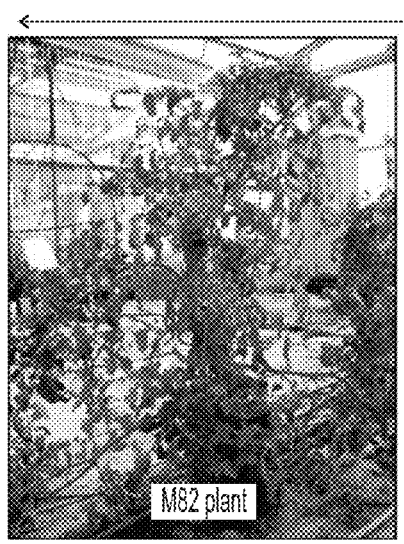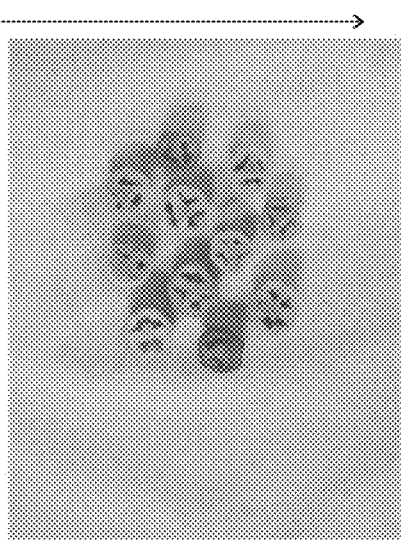
FIG. 1A  FIG. 1B  FIG. 1C
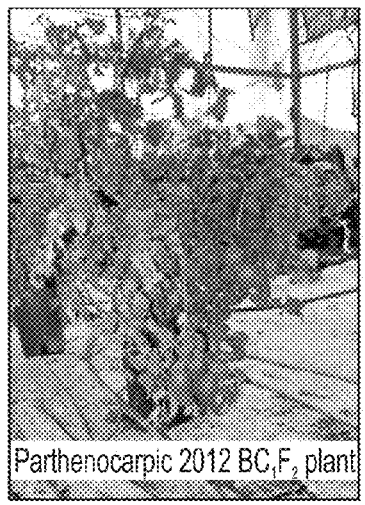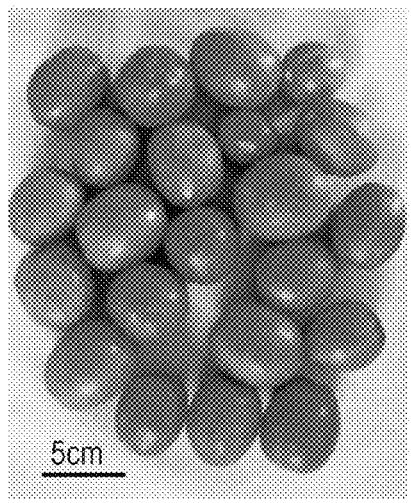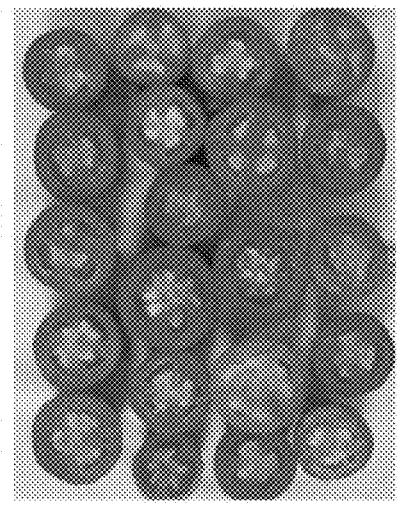
FIG. 1D  FIG. 1E  FIG. 1F
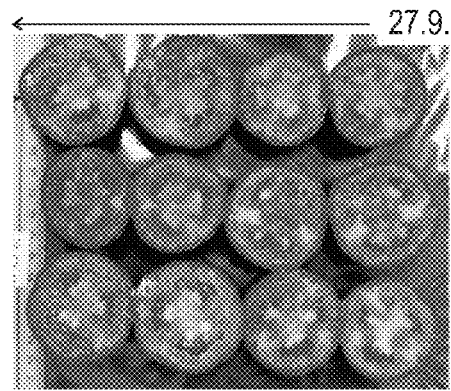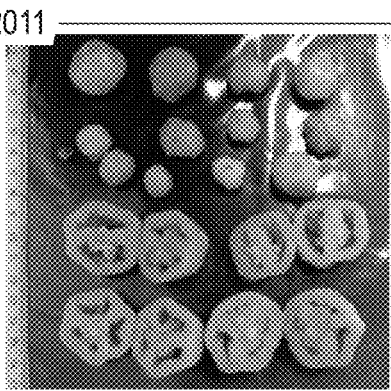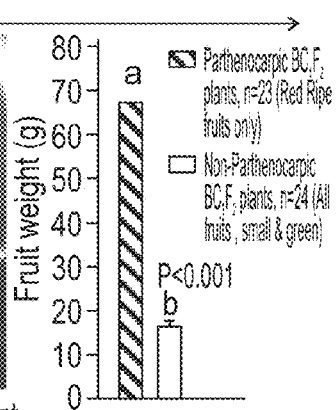
Parthenocarpic 2012 BC₁F₂ plant
FIG. 1G
Non-Parthenocarpic 2012 BC₁F₂ plant
FIG. 1H
FIG. 1I MGRGRVELKRIENKINRQVTFSKRRNGLLKKAYELSVLCEAEVALIIFSSRGKLYEFGSAGTKTLERYQRCCLNP
MADS-box (aa 2-72)
QDNCGERETQSWYQEVSKLKAKFEALQRTQRHLLGEDLGALSVKELQNLEKQLEGALAQARQRKTQIMME
K-box (aa 79-169)
QMEELRRKERHLGDVNKQLKIKVSLELSSFEGEGQGVPFPWSNCNASLDEAGSSTFHVHHSQSNHMDCDLP

DPVLQIGYHQYMAADGASGSRNMAVESNIIHGWGL*

FIG. 2A

ATGGGGAGAGGGAGAGTGGAACTAAAGAGAATAGAGAACAAAATCAACCGTCAAGTGACATTTTCTAAGAGGAGG

AATGGTTTGTTGAAGAAAGCTTATGAATTATCAGTGCTTTGTGAGGCTGAAGTTGCTCTCATCATCTTCTCTAGTCGTG

PAM ↓
GAAAGCTCTATGAGTTTGGTAGTGCAGGTATCACTAAAACCCTTGAGAGGTACCAACGTTGTTGCCTTAATCCTCAAG
Exon 1                                                                 AclI
                                                                  $C_{28d}/t$ (2012)
ACAATTGTGGTGAAAGAGAAACACAGAGCTGGTACCAAGAGGTCTCTAAATTAAAGGCCAAGTTTGAAGCACTTCA
Exon 2

ACGAACTCAAAGGCACTTGCTTGGTGAAGATCTTGGAGCACTAAGTGTGAAGGAGTTGCAAAAATCTTGAAAAACAA
Exon 3

CTTGAAGGTGCACTTGCACAAGCTAGACAAAGAAAGACACAAATAATGATGGAACAGATGGAGGAGCTTCGTAGAA
Exon 4                                                                    Exon 5
AGGAGCGTCATCTTGGTGATGTGAACAAGCAGTTGAAGATTAAGGTTTCTCTTGAACTATCATCGTTTGAGGGTGAA
                                                        Exon 6
GGACAAGGTGTTCCTTTTCCATGGAGTAATTGTAATGCATCTTTAGATGAAGCAGGAAGCAGCACCTTTCATGTCCAC CATTCTCAATCAAATCACATGGACTGTGATTTACCTGATCCAGTTCTTCAAATAGGGTATCATCAGTATATGGCTGCAGA
                                                        Exon 7
TGGAGCCTCAGGGTCAAGGAACATGGCTGTTGAGAGTAACATTATCCATGGTTGGGGTCTTTAA
                                                        Exon 8

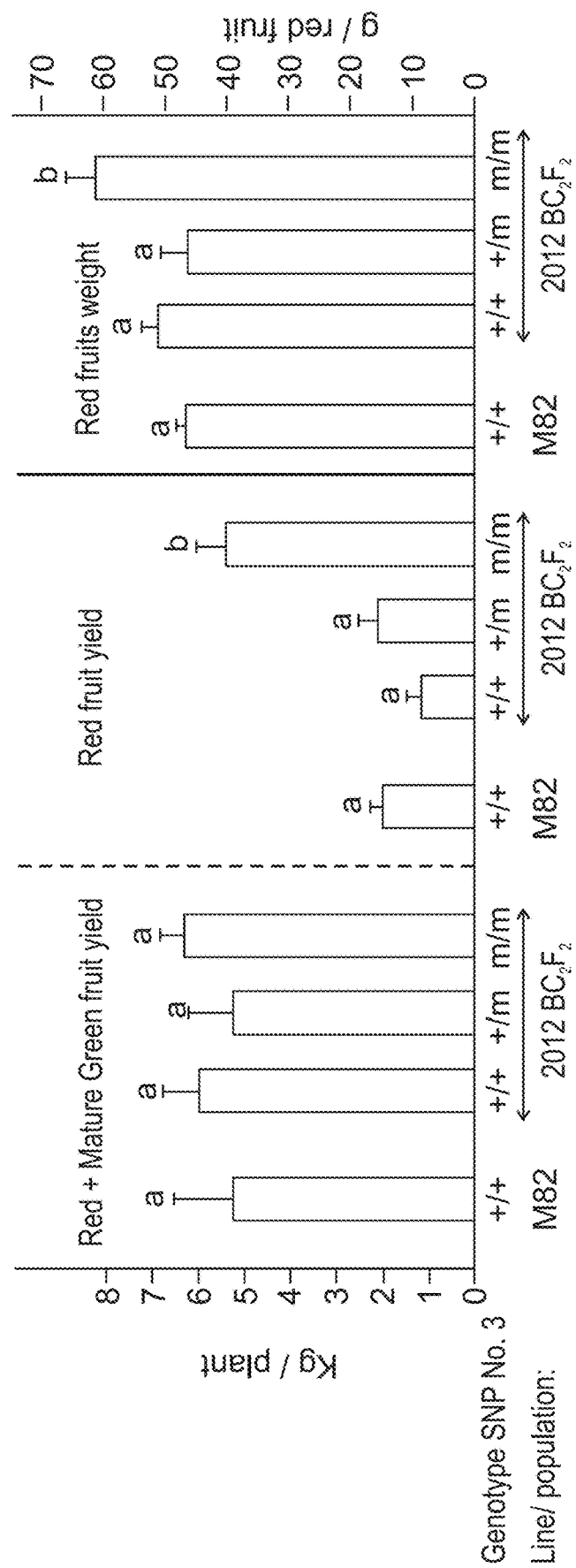

M82 (+/+)

2012 BC₂F₂ (+/+)

2012 BC₂F₂ (+/m)

2012 BC₂F₂ (m/m)

2012 BC₂F₂ (+/m)

2012 BC₂F₂ (m/m)

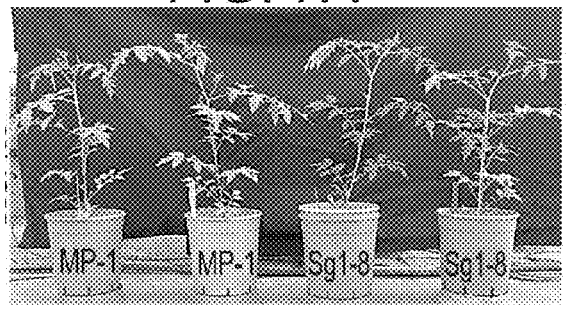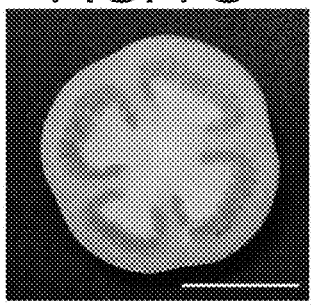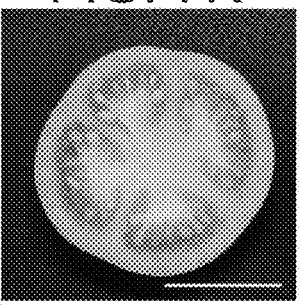
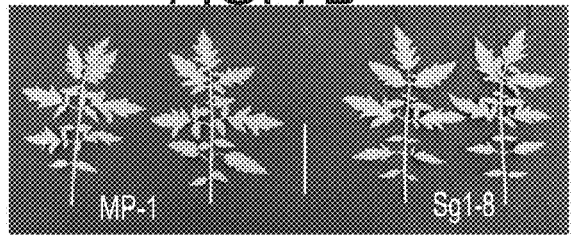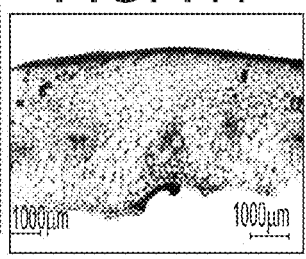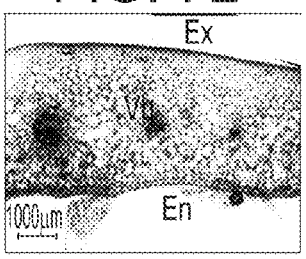
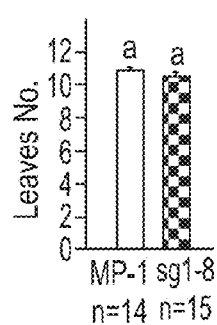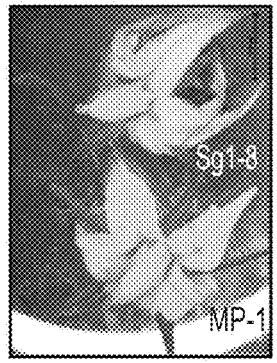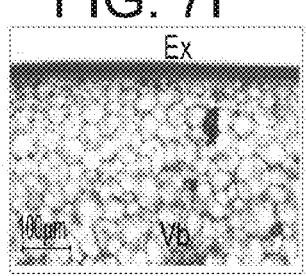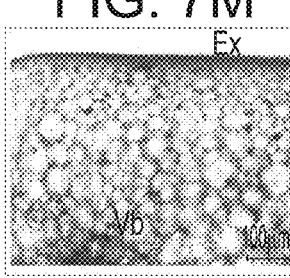
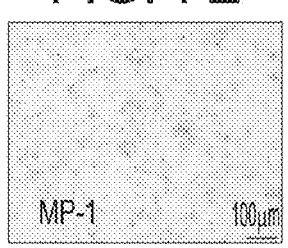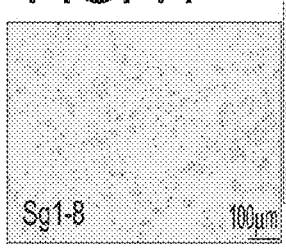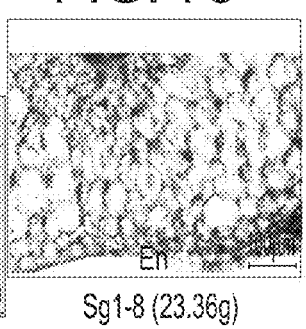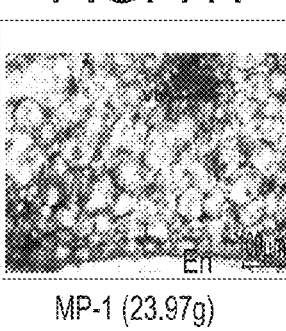

PARTHENOCARPIC TOMATO PLANTS WITH LOSS OF FUNCTION MUTATION IN AN AGL6 GENE AND METHODS OF PRODUCING SAME

RELATED APPLICATIONS

This application is a National Phase of PCT Patent Application No. PCT/IL2017/050078 having International filing date of Jan. 19, 2017, which claims the benefit of priority under 35 USC § 119(e) of U.S. Provisional Patent Application No. 62/281,227 filed on Jan. 21, 2016. The contents of the above applications are all incorporated by reference as if fully set forth herein in their entirety.

SEQUENCE LISTING STATEMENT

The ASCII file, entitled 74477SubstituteSequenceListing.txt, created on Sep. 29, 2020, comprising 48,277 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to parthenocarpic plants and methods of producing same.

Fruit development following fertilization is essential for the completion of the plant life cycle. In tomato, the ovary, which develops in concert with the rest of the flower organs (growth phase I, according to Gillaspy et al. 1993), ceases to undergo cell divisions shortly (1-2 days) before anthesis, hence entering "ovary arrest" state. Only if fertilization is successfully completed, a signal believed to be produced by the young embryo provokes the ovary to resume growth. This growth involves initially a phase of rapid cell division and expansion (designated phase II) for 7-10 days (Varga and Bruinsma 1986; Bohner and Bangerth 1988), and subsequently (during phase III) growth is driven mainly by cell enlargement concomitant with nuclear polyploidization (Joubes and Chevalier 2000, and references therein). Once reaching full size, ripening processes initiate.

The default program of fertilization-dependent fruit development safeguards the plant's fitness as resources are not wasted sustaining futile organ development. Alternatively, parthenocarpy, i.e. fertilization-independent seedless fruit development is a counterproductive trait in all wild species incapable of vegetative propagation. Yet mutations that enable fruit development in the absence of seeds development are of considerable importance in modern breeding of many crops, including tomato, and that for several reasons.

First, the microsporogenesis process and the mature male gametes are extremely sensitive to moderately high or low temperatures, and to extreme humidity or light intensity (El Ahmadi and Stevens 1979; Picken 1984; Sato et al 2006). This is a major hindrance for year-round fertilization dependent fruit yielding under field conditions of many important vegetable crops including tomato, pepper (*Capsicum annuum*), eggplant (aubergine) (*Solanum melongena*) and melon. Consequently, breeding for pollination-independent fruit yielding is considered a valuable goal especially in the context of maintaining sustainable agriculture under diverse environmental conditions (Gorguet et al. 2005; Ruan et al 2012; Ariizumi et al 2013, Shinozaki and Ezura 2016).

Second, seedlessness is a desired trait in elite cultivars intended for the fastidious consumers who find the seeds to impair the quality of various fruits including: watermelons, grapes, citrus, apple, pear, fig, eggplant, cucumber, squash, tomato, (particularly cherry tomato), banana, and different cactus fruits.

Third, in certain cases it was found to improve fruit quality. For example, in tomato seedlessness was reported to be associated with elevated content of total soluble solids (Falavigna et al. 1978; Casas Diaz et al. 1987; Ficcadenti et al. 1999; Carmi et al 2003), apparently because less of the assimilates are relocated from the flesh of the fruits into the seeds. Seedlessness was reported to delay the aging and deterioration of watermelon fruit supposedly because the seeds are the source of aging related hormones (Adelberg et al 1997).

Fourth, seedlessness can be of advantage in crops raised for processed products, such as tomato paste, paprika spice and canned melons, because the energy invested in separating the seeds from the processed product can be saved.

And lastly, parthenocarpy can be beneficial to seed companies as it assists in protecting their varieties.

Since tomato and other vegetables that could benefit from parthenocarpy are commonly propagated from seeds, hence only genetic sources for facultative parthenocarpy, where seeded fruits can develop following successful fertilization (Varoquaux et al 2000), are of practical value. Presently, the most extensively characterized non-transgenic sources for facultative parthenocarpy in tomato are: The three monogenic sources, pat (Beraldi et al., 2004; presumably a mutated Solyc03g120910, Selleri 2011), procera (a mutated SlDELLA, Bassel et al., 2008) and entire (mutated SlAUX/IAA9, Mazzucato et al., 2015; Saito et al., 2011), all of which manifest undesired pleotropic effects. The three digenic sources, pat-2 (Hazra and Dutta, 2010; Vardy et al., 1989b), IL5-1 and IVT-line1 (Gorguet et al., 2008), all manifesting acceptable parthenocarpic phenotype. Though pat-2 was reported to be associated with determinate growth habit (Lin et al 1984), and the fruit size is usually somewhat smaller than that of the recurrent parent (Vardy et al 1989b). And the inferior oligogenic source pat-3/pat-4 (Nuez et al., 1986; Philouze and Maisonneuve, 1978, Vardy et al 1989b). Despite the importance of this trait, exploitation of these mutants in breeding programs is still rather limited. Some of them are associated with mild or severely undesirable pleotropic effects (e.g., Ariizumi et al., 2013; Carrera et al., 2012; Lin et al., 1984; Mazzucato et al., 1998; Philouze 1989; Shinozaki and Ezura 2016). And introgression of a digenic source is much more laborious, especially since the identity of the genes underlying any of these three digenic sources was not reported so far (Shinozaki and Ezura 2016).

MADS-box genes have been previously reported to regulate flower and fruit development (Yao 2001, Proc. Natl. Acad. Sci. 98(3):1306-1311; Rijpkema et al. Plant J. 60(1):1-9, Wang et al. 2009 Plant Cell. 21:1428-1452). However, no real parthenocarpy was ever observed in tomatoes genetically modified in a MADS-box gene (e.g., Pnueli et al 1994 Plant Cell 6(2):163-173; Amporah-Dwamena et al., Plant Physiol. 2002 130(2):605-17, Pan et al 2010, J. Exp. Bot. 61:1795-1806) since parthenocarpy, even if observed, was always manifested by severe homeotic aberrations, rather than resulting in development of a normal fruit which is devoid of seeds in the absence of fertilization.

In other species, silencing or mutations of genes homologous to SlAGL6, did not cause parthenocarpy: e.g. *Petunia*, where parthenocarpy was not reported (Rijpkema et al. Plant J. 60(1):1-9), *Arabidopsis* where it affected time to flowering and branching but did not cause parthenocarpy (Koo et al 2010). Knocking-down its *Nigella damascene* homolog affected sepals and petals structure indicating an A-function, yet parthenocarpy was not reported (Wang et al., 2015). In Rice it caused severe alteration in flower morphology (Zhang et al 2010, Duan et al 2012), very different from the phenotype we see in tomato, (in rice where the seeds are the product one cannot seriously talk about parthenocarpy anyway).

Additional related background art:
US Pat. Appl. 20100146656
US Pat. Appl. 20090089902
US Pat. Appl. 20030217391
US Pat. Appl. 20070250945
U.S. Pat. No. 6,268,552.

SUMMARY OF THE INVENTION

According to an aspect of some embodiments of the present invention there is provided a Solanaceous plant selected from the group consisting of tomato, pepper and eggplant exhibiting a facultative parthenocarpy and comprising a loss-of-function mutation in an AGL6 gene.

According to an aspect of some embodiments of the present invention there is provided a Solanaceous plant selected from the group consisting of tomato, pepper and eggplant exhibiting a facultative parthenocarpy and an average fruit weight/plant at least about the same as that of a non-parthenocarpic tomato of the same genetic background.

According to some embodiments of the invention, the Solanaceous plant further exhibits at least one of:
  (i) a fruit yield/plant at least about the same as that of a non-parthenocarpic tomato of the same genetic background under fertilization permissive conditions of the non-parthenocarpic tomato;
  (ii) an average fruit weight/plant at least about the same as that of a non-parthenocarpic tomato of the same genetic background under fertilization permissive conditions of the non-parthenocarpic tomato;
  (iii) comprising jelly fill when the Solanaceous plant is tomato;
  (iv) at least 80% of the fruit yield being devoid of homeotic aberrations; and (v) enlarged ovules within the seedless fruits developed from non-fertilized ovaries.

According to some embodiments of the invention, the fruit yield is red fruit yield.

According to some embodiments of the invention, the plant is a tomato.

According to some embodiments of the invention, the plant is a processing tomato.

According to some embodiments of the invention, the plant is a determinate tomato.

According to some embodiments of the invention, the plant is an indeterminate tomato.

According to some embodiments of the invention, the plant is a semi-determinate tomato.

According to some embodiments of the invention, the plant is of an elite line.

According to some embodiments of the invention, the plant is transgenic.

According to some embodiments of the invention, the tomato is of a species selected from the group consisting of *Lycopersicon esculentum, Lycopersicon cerasiforme, Lycopersicon pimpinellifolium, Lycopersicon cheesmanii, Lycopersicon parviflorum, Lycopersicon chmielewskii, Lycopersicon hirsutum, Lycopersicon penellii, Lycopersicon peruvianum, Lycopersicon chilense* and *Solanum lycopersicoides*.

According to some embodiments of the invention, are tomato is selected from the group consisting of a single fruit per truss, branched tomato and cherry tomato.

According to some embodiments of the invention, are facultative parthenocarpy is manifested under heat or cold stress.

According to some embodiments of the invention, the plant is an inbred.

According to some embodiments of the invention, the plant comprises a loss-of-function mutation in an AGL6 gene.

According to some embodiments of the invention, are loss-of-function mutation is in a homozygous form.

According to some embodiments of the invention, the plant comprises a silencing agent for suppressing expression of an AGL6 gene.

According to some embodiments of the invention, the plant exogenously expresses a nuclease selected from the group consisting of a meganuclease, an RNA-guided DNA endonuclease, a zinc-finger nuclease and a TALEN.

According to an aspect of some embodiments of the present invention there is provided a fruit of the plant.

According to an aspect of some embodiments of the present invention there is provided a seed of the plant.

According to some embodiments of the invention, the seed is a hybrid seed.

According to an aspect of some embodiments of the present invention there is provided an edible processed product of the plant or fruit.

According to some embodiments of the invention, the processed product is selected from the group consisting of a tomato paste, a ketchup, a tomato sauce a tomato soup, a tomato juice, a tomato powder, a tomato dice, a crushed tomato, a chopped tomato and a tomato concentrate.

According to an aspect of some embodiments of the present invention there is provided a method of producing the plant, the method comprising down-regulating expression or activity of AGL6 gene in the plant.

According to some embodiments of the invention, are down-regulating is effected by treating the plant or a regenerative portion thereof with a mutagen.

According to some embodiments of the invention, are down-regulating is effected by treating the plant with an RNA silencing agent.

According to some embodiments of the invention, are down-regulating is effected by treating the plant with a DNA editing agent.

According to some embodiments of the invention, the method comprises selfing or crossing the plant.

According to an aspect of some embodiments of the present invention there is provided a method of breeding comprising selfing or crossing the plant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-I show that the mutation 2012 enables parthenocarpic fruit set under extreme hot stress. Parthenocarpic $BC_1F_2$ progenies set high quality fruits from flower developing during the extremely hot summer (July-August) of 2010, and were harvested on the 20 Sep. 2010. FIGS. 1A-C): M82 line plants did not bear any normal fruits, only tiny, hollow, "nuts" fruitlets. Compare to FIGS. 1D-F): parthenocarpic siblings of the $BC_1F_2$ population which set many red, high quality fruits under the same conditions. Stability of the trait was confirmed in the following summer. $BC_1F_2$ progenies were grown in the late summer of 2011. FIG. 1G). While parthenocarpic siblings did set high quality red ripe fruit, FIG. 1H) non-parthenocarpic siblings set only tiny "nuts" fruits, or a few small puffy fruits bearing a few seeds. Fruit were harvested on 27 Sep. 2011. FIG. 1I). The weight of the parthenocarpic red fruit harvested at that date was significantly (t-test, p<0.001) higher than that of the fruits, mostly green, collected from non-parthenocarpic siblings.

FIGS. 2A-B describe SLAGL6. (FIG. 2A, SEQ ID NO: 21) The protein sequence of the MADS box protein SlAGL6. The MADS box is highlighted dark grey, the K-box is highlighted light grey. (FIG. 2B, SEQ ID NO: 22) The ORF of SlAGL6; alternate exons are underlined by full and dashed lines. The C268/t mutation underlying the mutant 2012 is marked. The chosen target guiding sequence for CRISPR/cas9 modification is presented by thick black line above the sequence, and the adjacent PAM (its reverse complement) is depicted by dashed line, the arrowhead marks the Cas9 cleavage target site, the AclI restriction site (AACGTT) which is expected to be destroyed by Cas9 induced mutations is highlighted grey.

Figure 3A:
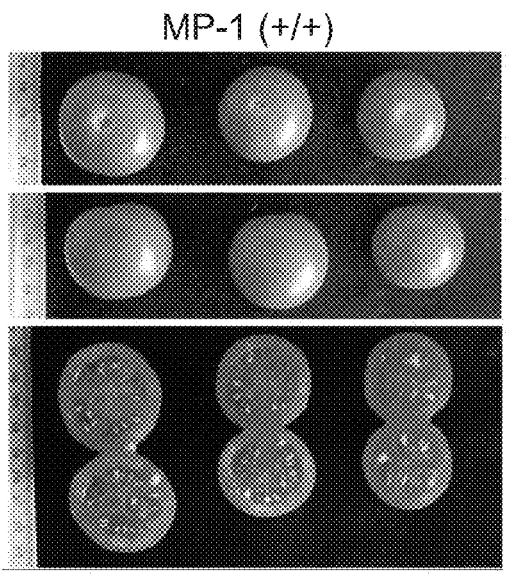
Figure 3B:
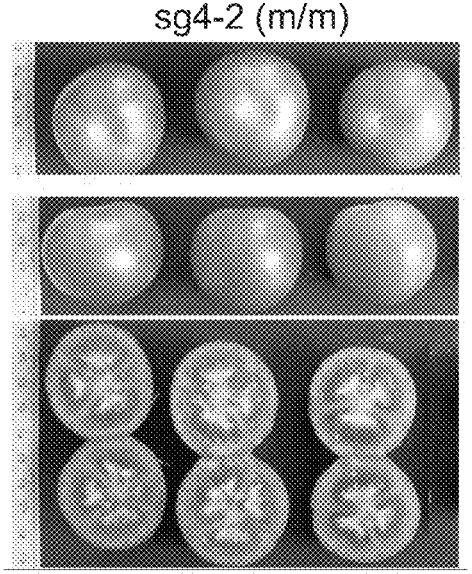
Figure 3C:
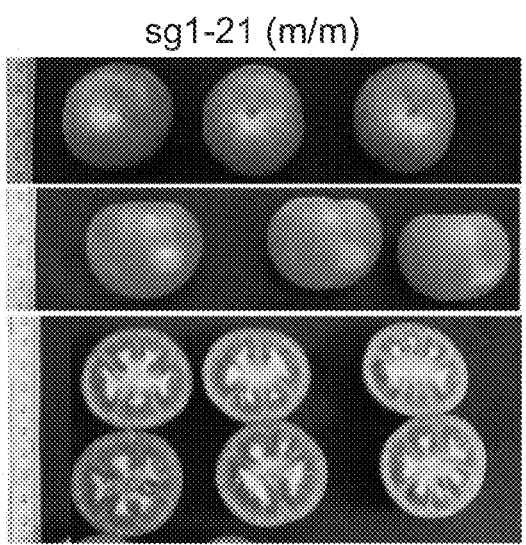
Figure 3D:
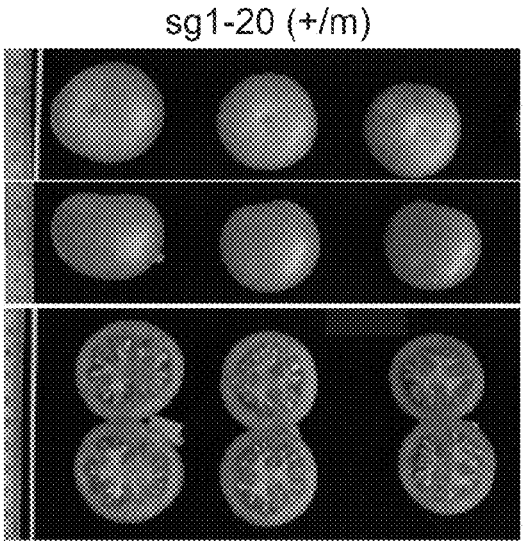
Figure 3E:
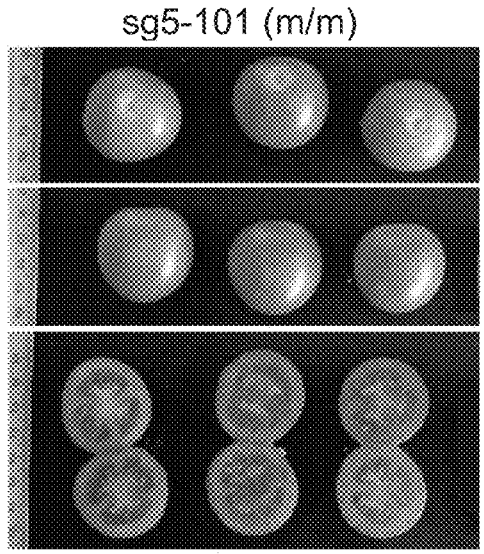
Figure 3F:
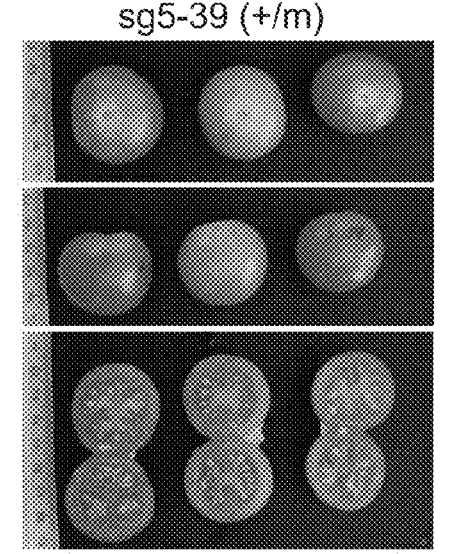

FIGS. 3A-F show parthenocarpy in plants homozygous for CRISPR/cas9 induced mutated alleles of SlAGL6. FIG. 3A). Seeded fruits of the parental WT line MP-1. FIG. 3B) Seedless fruits of sg4-2 $R_1$ progeny of $R_0$ plant sg4, carrying bi-allelic mutation. FIG. 3C) Seedless fruits of sg1-21, a homozygote progeny for the mutated version found in $R_0$ plant sg1, vs. FIG. 3D) fruits of sg1-20, a heterozygous sibling progeny bearing seeded fruits only. FIG. 3E) Seedless fruits of sg5-101, a homozygous progeny for the mutated version found in $R_0$ plant sg5, vs. FIG. 3F) fruits of sg5-39, a heterozygous sibling progeny bearing seeded fruits only. In genotype description, (+) stands for the WT allele, and (m) for all the different mutated versions of SLAGL6 induced.

Figures 4A, 4B:
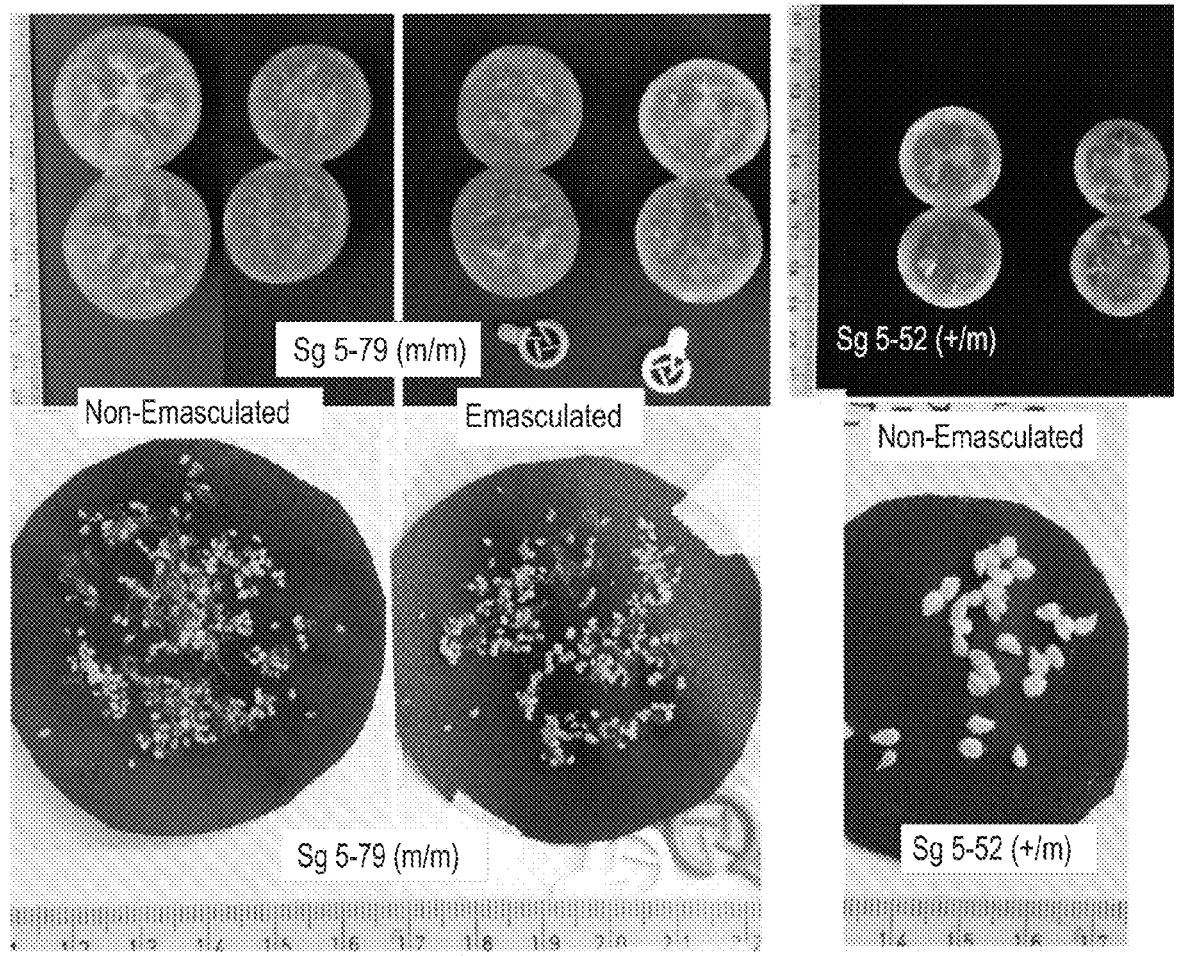
Figure 4C:
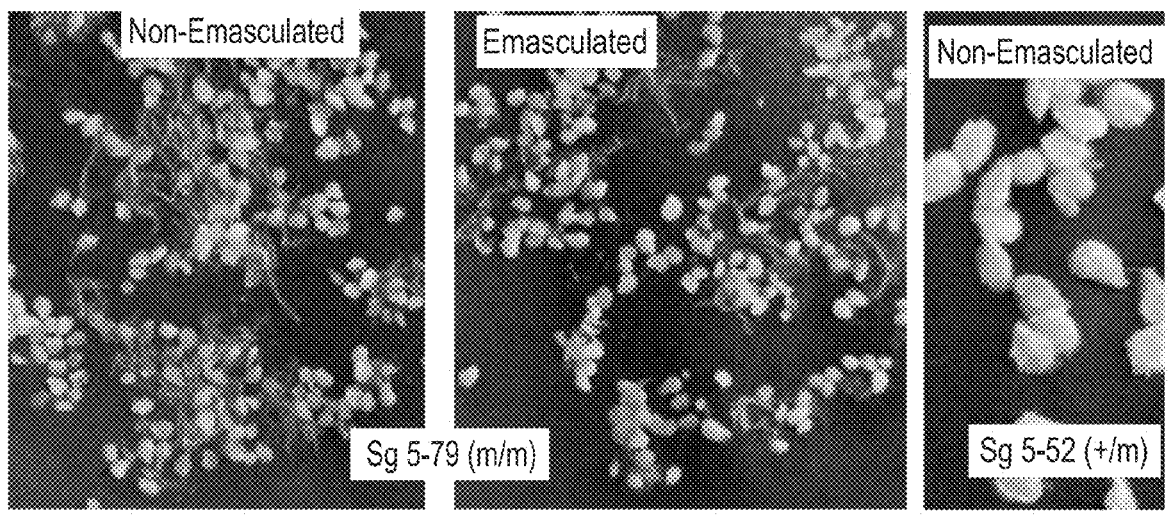

FIGS. 4A-C show similarly enlarged ovules developed on the placenta of emasculated and non-emasculated parthenocarpic fruits. FIG. 4A) Flowers of the parthenocarpic CRISPR derived plant sg5-79 (m/m) were emasculated at pre-anthesis and marked by coloured tags (fruits in the right-hand side of the upper panel). The size and appearance of the enlarged ovules collected from the emasculated and from non-emasculated fruits (left hand fruits in the upper panel) developed on the same plant do not differ in size and appearance (middle panel). FIG. 4B). For comparison presented are seeds collected from heterozygote sibling sg5-52. This fruit is small, as it bears very few seeds, further, its seeds are smaller than those developed in fruits developed under ambient rather than hot temperatures (data not shown). FIG. 4C) Higher magnification of the ovules presented in the middle row panels. All the presented fruits were collected at the same date, 30 Sep. 2015.

FIGS. 5A-C show yield analysis of 2012 $BC_2F_2$ plants with different genotypes of SNP No. 3 (SlAGL6), and the parental line M82. (FIG. 5A) Since the parthenocarpic plants manifested profoundly more concentrated fruit development and ripening (see FIGS. 6A-F), to assess the effect of the mutated genotype on yielding potential, the yield of all fruits reaching at least nearly mature green stage were included in the presented analysis, showing that the various genotypes of 2012 did not differ from M82 in total yield potential. (FIG. 5B) The marketable red fruit yield of the (m/m) parthenocarpic plants was significantly (p<0.001) higher than that of line M82 or siblings not homozygous for SNP No. 3. (FIG. 5C) The average weight of the red fruits derived from the parthenocarpic (m/m) was the only one significantly higher than that of the parental line M82. In each panel, bars accompanied by different small-case letters differ significantly.

Figure 6A:
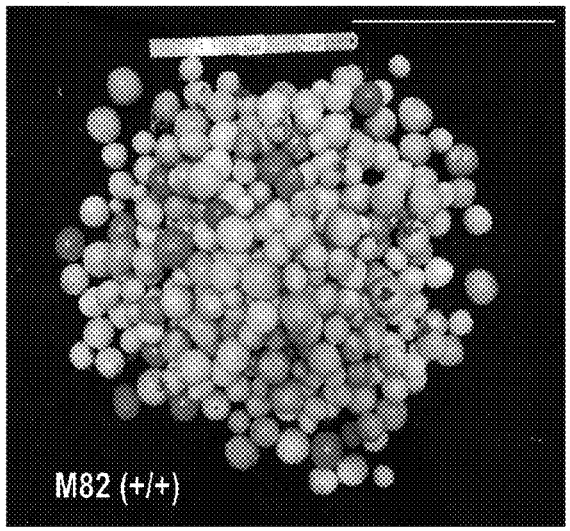
Figure 6B:
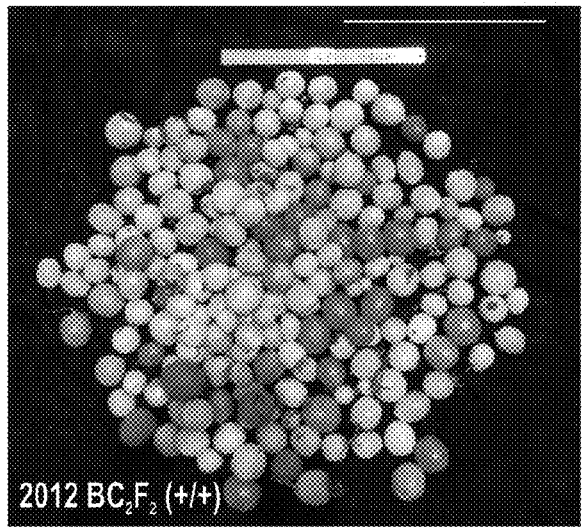
Figure 6C:
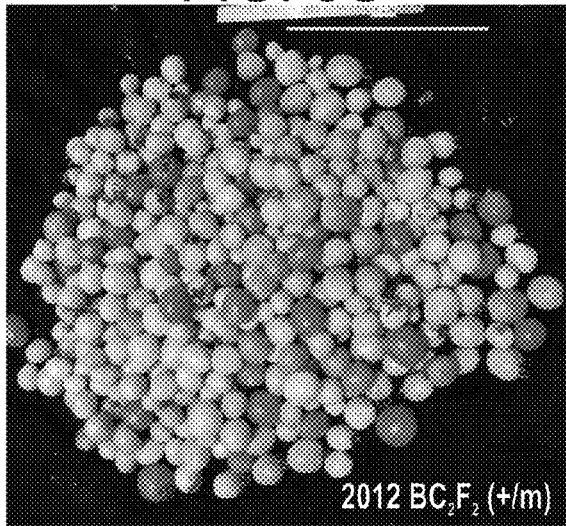
Figure 6D:
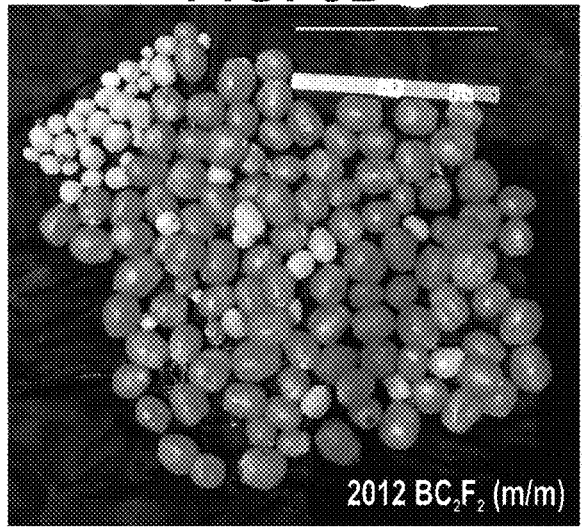
Figure 6E:
Figure 6F:

FIGS. 6A-F are fruits harvested from representative single plants from 2012 $BC_2F_2$ population. Homozygotes for mutated SNP. No. 3 (agl6), are characterized by rapid uniform ripening of the fruits. In the upper four panels the total yield (besides the tiny "nuts") of picked fruits from a single plant of the specified genotype are presented. As clearly shown, unlike for M82, (FIG. 6A) and $BC_2F_2$ plants either homozygous for the WT allele (+/+) (FIG. 6B), or heterozygous for SNP No. 3 (FIG. 6C), most of the fruits of (m/m) plant (FIG. 6D) are red ripe. All plants were harvested at the same date (Oct. 6, 2014). When examining the plants before their harvest, the concentrated nature of the (m/m) plants yielding is clearly visualized, (FIG. 6F), versus the non-concentrated fruit development on a (+/m) plant (FIG. 6E).

FIGS. 7A-N show a comparison in appearance of the parental line MP-1 and SlAGL6 mutated line sg1-8 (at $R_2$). FIG. 7A) The plants do not differ in growth habit, FIG. 7B) The shape of the leaves is similar, scale=8 cm. FIG. 7C) The first inflorescence appeared after a similar number of true leaves (Mann-Whitney rank sum test, P=0.371). FIG. 7D) the flowers are similar except of the petals of sg1-8 being paler, and somewhat narrower and longer than those of MP-1. Pollen fertility is similar in MP-1 (FIG. 7E) and sg1-8 (FIG. 7F). Presented are in vitro germinated pollen grains with similarly elongated pollen tubes, photographed after 18 h incubation, scale=100 μm. FIGS. 7G-N) The pericarp of parthenocarpic fruit of line sg1-8 (FIGS. 7G-J) is similar to that of seeded fruit of MP-1 (FIGS. 7K-N) of similar weight and size (FIGS. 7G,K scale=2 cm). FIGS. 7H,L) the pericarp is of similar width and shape, scale=1000 μm. The cells in the layers between the vascular bundle rim and the exodermis (the exocarp) (FIGS. 7I,M), and those between the vascular bundle rim and the endodermis (endocarp) (FIGS. 7J,N) are of similar appearance, FIGS. 7I, 7J, 7M, 7N scale=500 μm. Photographs (FIGS. 7H-J and L-N) are of thin free-hand transverse sections taken from the middle (equator) of the nearly mature green fruits presented in G,K, and photographed under an inverted light microscope. Line sg1-8 is mutated for SlAGL6, and devoid of the Cas9 cassette, it carries the mutation sg1 depicted in Table 4.

FIGS. 8A-D show typical shapes of 2012 $BC_2F_2$ (m/m) parthenocarpic fruits. (FIG. 8A) "Gamba like" larger fruits. (FIG. 8B) elliptic shaped fruits, upper panel-longitudinal side view, lower panel-transversely cut view, the largest fruits are seedless, the smaller bear few seeds, some of which are marked by arrowheads. (FIG. 8C) Many elliptic fruits of similar size developed on a single truss, all the fruits presented are from the same truss, 9 out of 12 are at the red ripe stage (left hand panel), transversely cut fruits from the same plant (right hand panel). Compared to (FIG. 8D) M82 seeded fruits. Scale=10 cm in all panels.

Figure 9A:
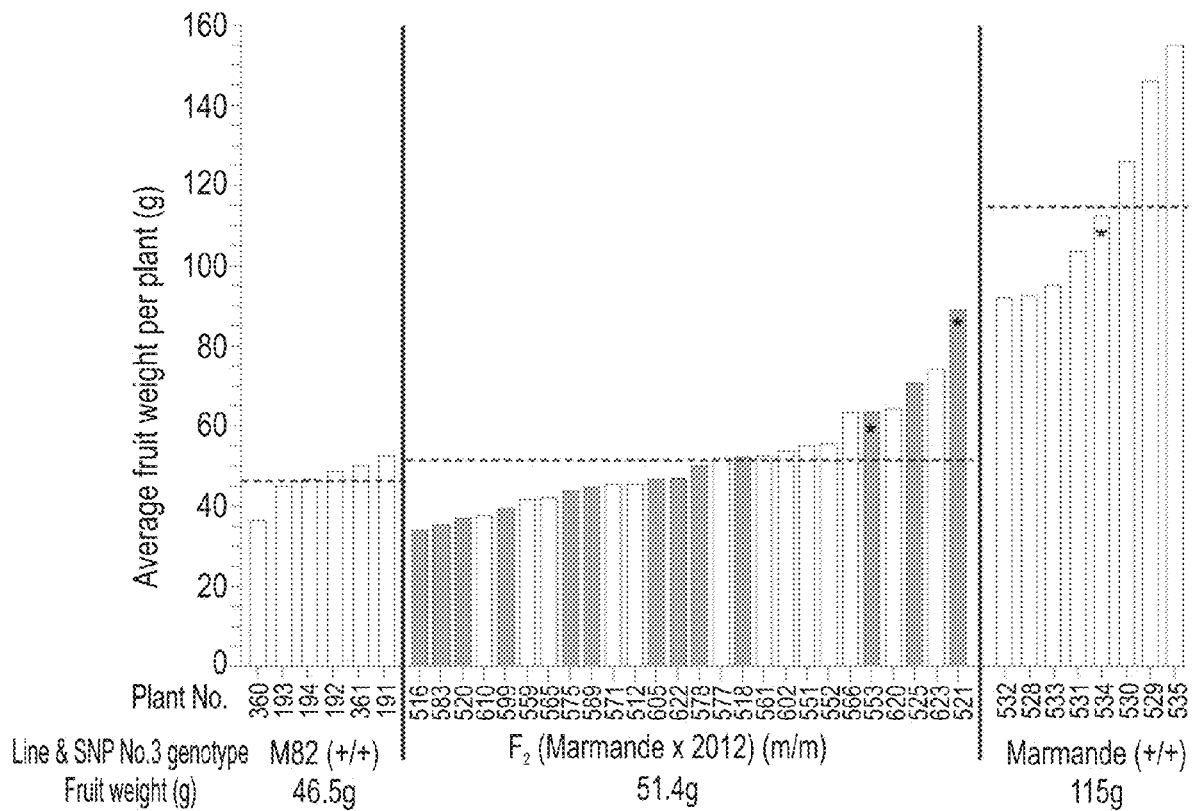
Figure 9B:
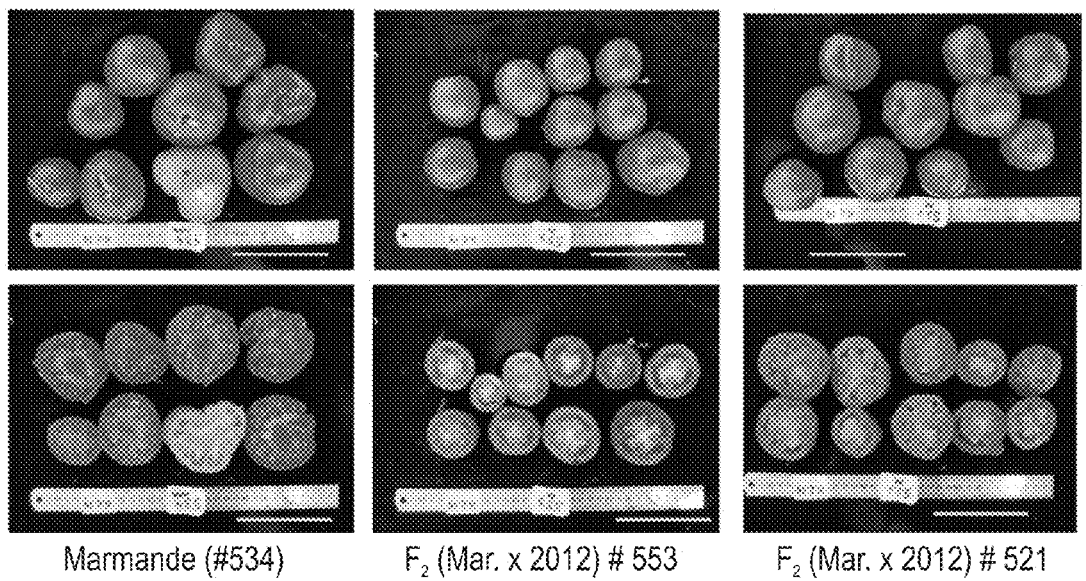

FIGS. 9A-B show the manifestation of the 2012 mutation in a larger fruit background. (FIG. 9A). Distribution of average fruit weight (g) and seedlessness among $F_2$ progenies of a cross between Marmande and parthenocarpic 2012 plant homozygous for mutated SNP No. 3 (Slag6). Only progenies homozygous for mutated SNP No. 3 are presented, in comparison to the average fruit weight of single plants of the parental lines. $F_2$ plants represented by grey bar did bear seedless fruits. The bars including asterisk (*) are those which fruits are presented in (FIG. 9B). Notice that some of the parthenocarpic fruits of plant #521 are similar in size and shape to those of Marmande fruits. Scale=10 cm.

Figure 10:
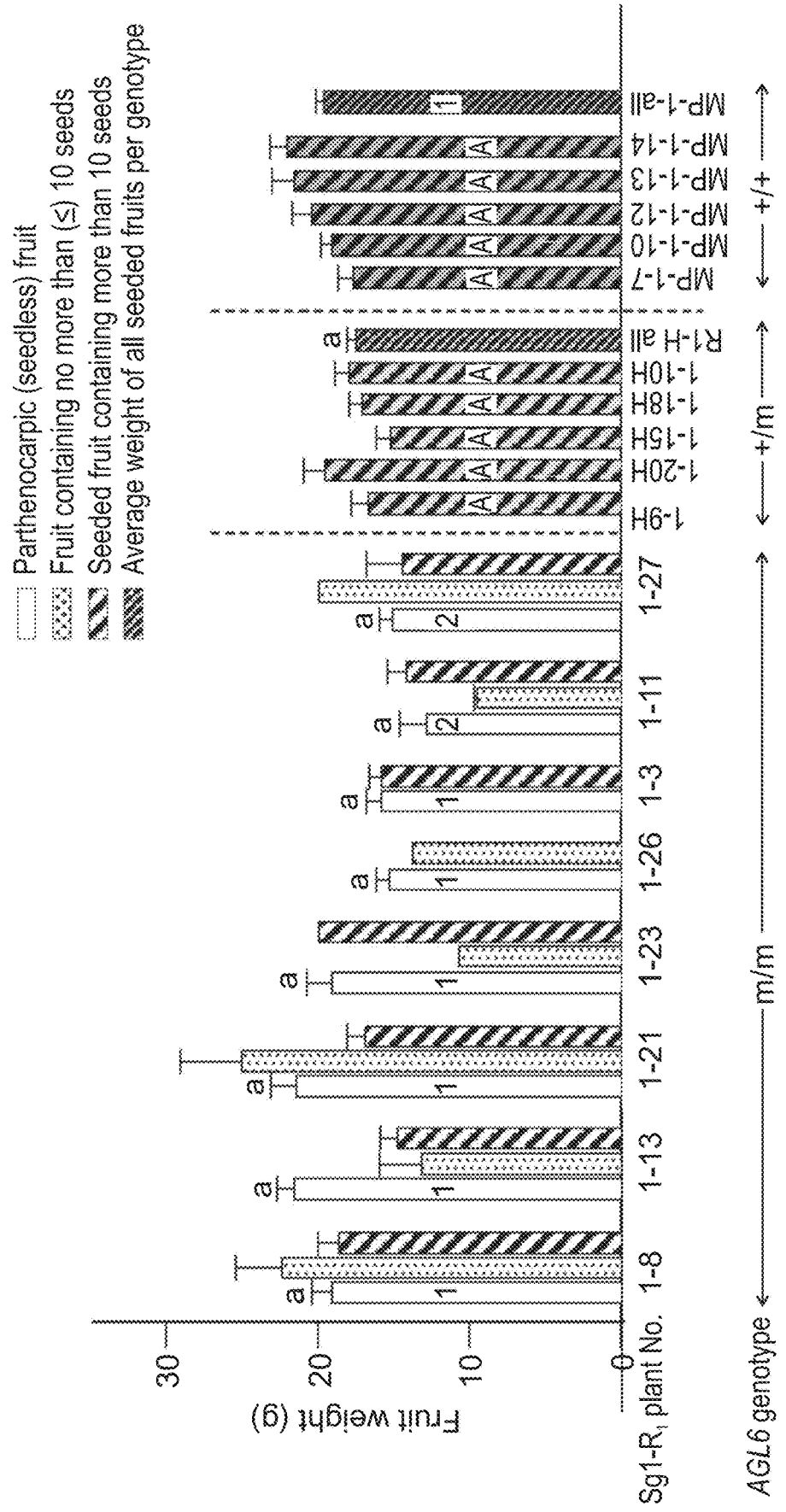

FIG. 10 shows an average weight of seeded, under-seeded and seedless fruits of $R_1$ progenies of the CRISPR/Cas9 SlAGL6 mutated line sg1, compared with the parental line MP-1. Empty bars (parthenocarpic fruits) accompanied by lower-case letters similar to that of the 1H all (average weight of seeded fruits of all heterozygous sg1 progenies) do not differ significantly (t-test, p<0.05). Empty bars (parthenocarpic fruits) marked inside the bar by a number different than that of the MP-1 all bar (average weight of seeded fruits of MP-1 plants) differ significantly (p<0.05, according to t-test, or Mann-Whitney test). Bars marked inside by the same A letter do not differ significantly (Anova, multiple range test).

Figure 11:
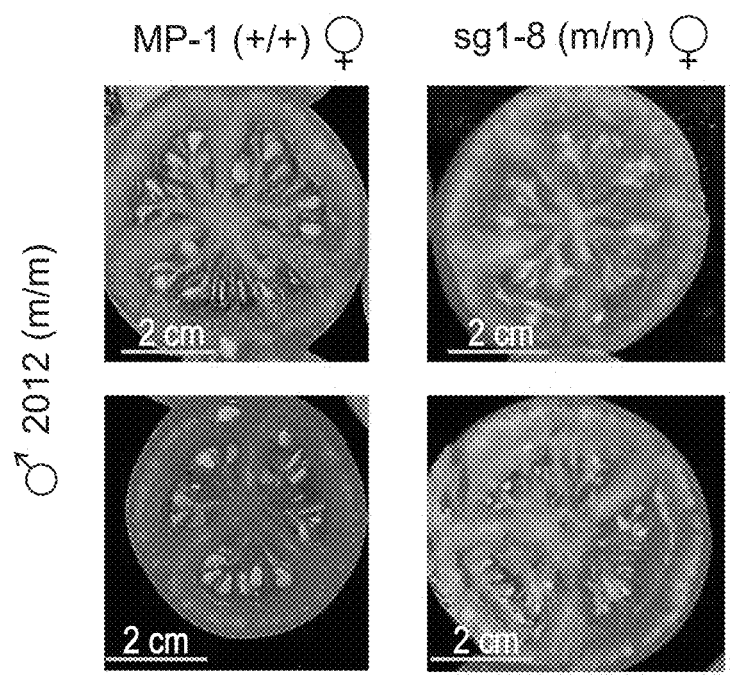

FIG. 11 shows that a hybrid between a plant homozygous for the 2012 mutated allele of SlAGL6 and a plant homozygous for the sg1 mutated allele produced seedless fruits, whereas a hybrid between the same 2012 plant and MP-1 (Wild-Type) produced seeded fruits only, testifying to allelisim of 2012 and sg1 mutated version of SlAGL6.

Figure 12:
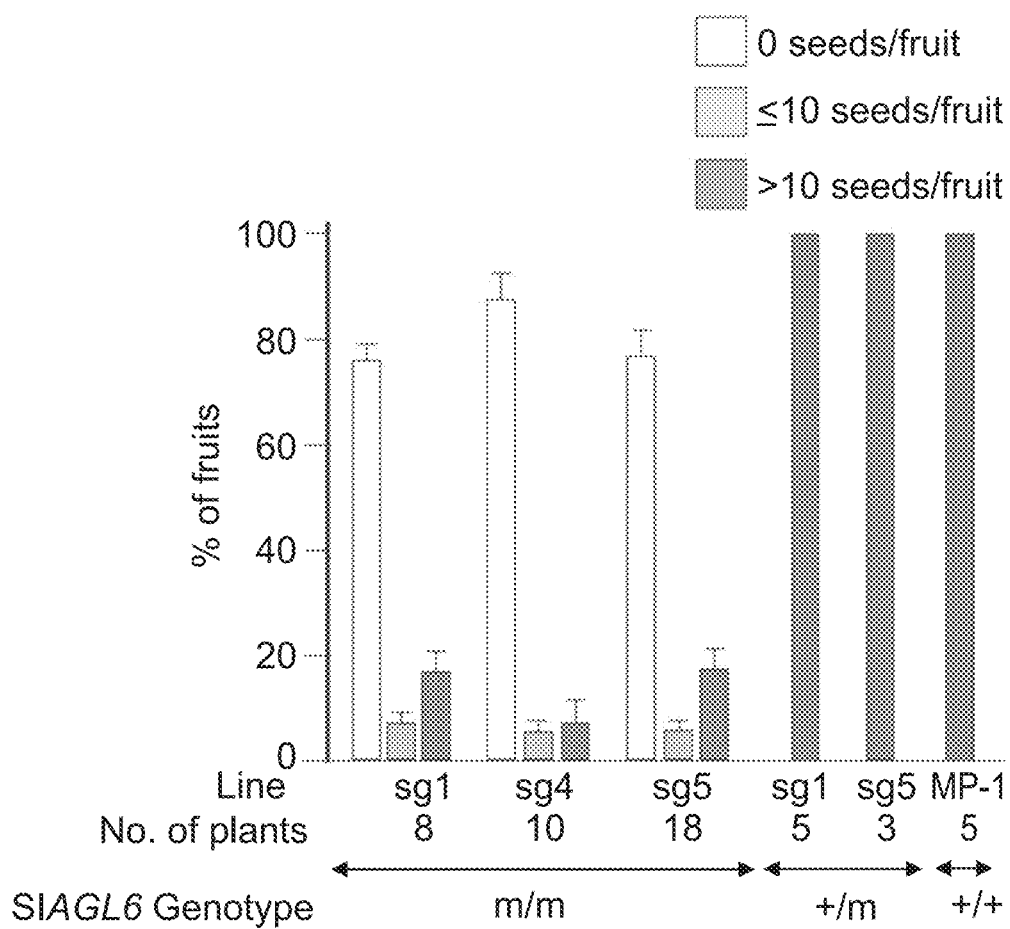

FIG. 12 shows the facultative nature of the parthenocarpy manifested in three different CRISPR induced mutations sg1, sg4 and sg5 of SlAGL6 when neither emasculating nor vibrating the flower.

Figures 13A, 13B, 13C, 13D, 13E:
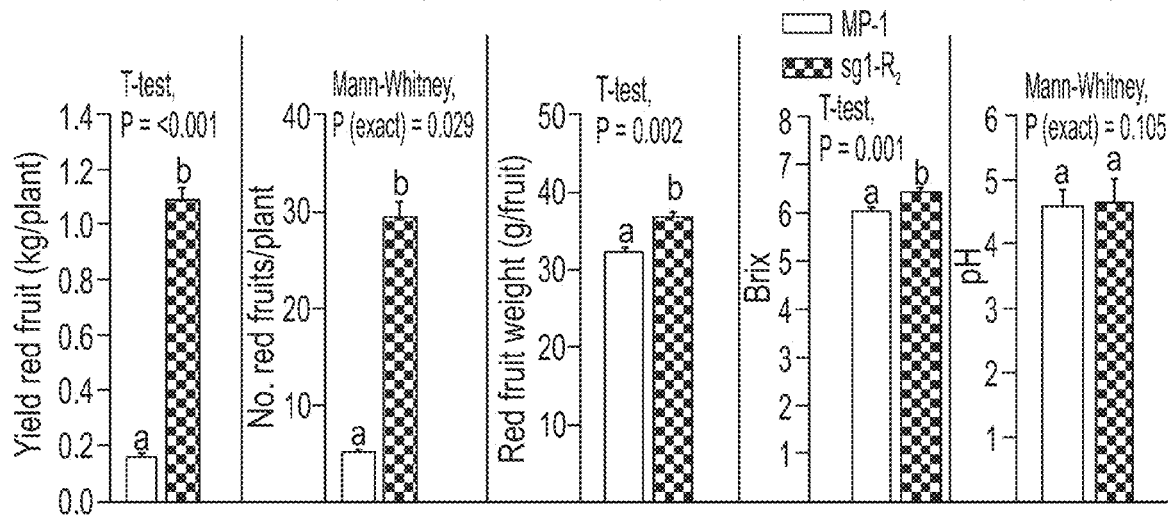
Figure 13F:
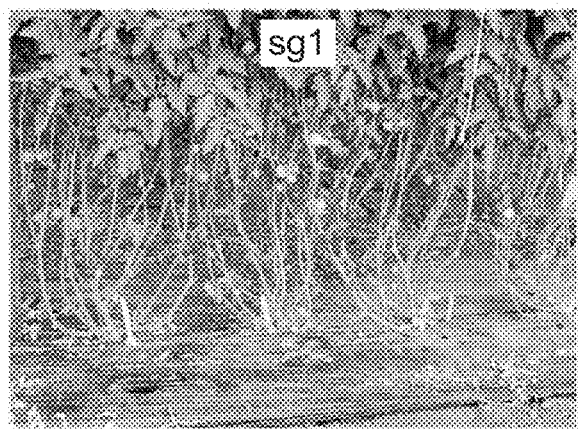
Figure 13G:
Figure 13H:
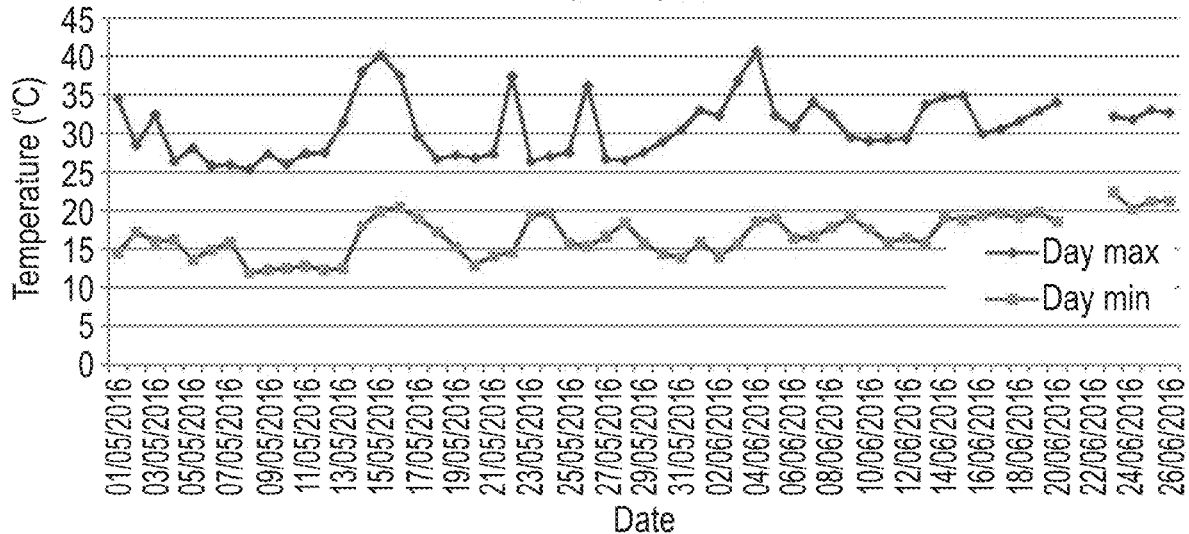

FIGS. 13A-H show that Slagl6 parthenocarpy improves yield under heat stress. Compared to line MP-1, line sg1 manifests significantly higher: FIG. 13A) red fruit yield, FIG. 13B) number of red fruits, FIG. 13C) red fruit weight, and FIG. 13D) Brix, while FIG. 13E) the fruit pH remains unchanged. Data presented in FIGS. 13A-E is derived from experiment performed on four replicates as detailed in Material and Methods. FIGS. 13F,G) Difference in fruit load between MP-1 (FIG. 13F) and sg1 (FIG. 13G) plants partly defoliated and photographed before harvest. FIG. 13H) Heat stress conditions prevailing during the summer of 2016, when comparing the yield of MP-1 and the Slagl6 line sg1. Seedlings were planted in the net-house 20 Apr. 2016, and first harvested 26 Jun. 2016 (data in FIGS. 13A-E, was obtained from this harvest). Notice the exceptionally high day and night temperatures between 14-16 May 2016 (FIG. 13H). Line sg1 (at $R_2$) is homozygous for the sg1 mutation and devoid of the Cas9 cassette.

DESCRIPTION OF SPECIFIC EMBODIMENTS OF THE INVENTION

The present invention, in some embodiments thereof, relates to parthenocarpic plants and methods of producing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst reducing the present invention to practice, the present inventors demonstrated that (various) mutated alleles of the MADS box gene Agamous like 6 (SlAGL6) confer strong though facultative parthenocarpy in tomato, and that without any visible pleotropic effects, thus rendering it a new useful source for parthenocarpy in tomato.

Specifically, the present inventors have established that the parthenocarpic 2012 mutant found in EMS mutagenized tomato population, generated in the background of the determinate processing cultivar M82, is caused by a mutated SlAGL6 gene containing a premature stop codon after the first 89 aa. Its identification was based on bioinformatics analysis of NGS data followed by molecular markers assisted mapping of SNPs (Tables 1, 2, 3; FIGS. 1A-I, 5A-C, 6A-F, 8A-D). The finding was validated by generating de novo the same parthenocarpic phenotype exploiting CRISPR/cas9 technology to mutate exclusively the SlAGL6 (FIGS. 2A-B), and that in the background of the indeterminate line MP-1 (Tables 4B, 5, 6, FIGS. 3A-F). An additional proof for the identity of 2012 as mutated SlAGL6 was provided by showing that the $F_1$ cross between homozygous 2012 and homozygous CRISPR mutant sg 1 produced seedless progenies (FIG. 11).

This mutation in a homozygous state enables fruit development both under chronic heat stress (FIG. 13H) that seriously hampered yielding of plant not carrying the mutation in a homozygous state (FIGS. 13A-C) and also under extreme heat and cold conditions, such that practically prevent yielding of plants not carrying the mutation in a homozygous state (FIGS. 1A-I).

The mutation does not adversely affect the yielding potential (FIGS. 5A-C), or the vegetative development of the plants. In determinate background it improves the concentration of the yield (FIGS. 5A-C, 6A-F), a trait of utmost importance for determinate processing tomato cultivars that are grown in the field, and expected to yield a concentrated crop which is collected by a single mechanical harvest. Outdoor growth risks exposure to short spells of extremely fluctuating temperatures which damage pollen development and hence profoundly reduced the marketable yield. This in turn abolishes yielding on consecutive flowering stages, resulting in non-uniform ripening and severe yield losses. This risk is minimized in Slagl6 parthenocarpic mutants. The mutation enables fruit set and development in the indeterminate line MP-1, under very high or low temperatures, thus its incorporation to commercial semi-determinate or indeterminate fresh market cultivars, will ensure continuous yielding along several months without losing yield from trusses flowering under pollination restrictive environmental conditions.

Importantly, whilst further conceiving the embodiments of the invention, the present inventors have realized that the same teachings can be applied toward other Solanaceous plants having fleshy fruit i.e., pepper and eggplant. Hence, according to an embodiment of the invention the present disclosure is directed to this subclass of Solanaceous plants though each plant species is considered an independent embodiment.

Thus, according to an aspect there is provided a Solanaceous plant selected from the group consisting of tomato, pepper and eggplant exhibiting a facultative parthenocarpy and comprising a loss-of-function mutation in an AGL6 gene.

Alternatively or additionally, there is provided a Solanaceous plant selected from the group consisting of tomato, pepper and eggplant exhibiting a facultative parthenocarpy and an average fruit weight/plant at least about the same as that of a non-parthenocarpic tomato of the same genetic background.

The term "plant" as used herein encompasses whole plants, a grafted plant, ancestors and progeny of the plants and plant parts, including seeds, shoots, stems, roots, rootstock, scion, and plant cells, tissues and organs. The plant may be in any form including suspension cultures, embryos, meristematic regions, callus tissue, leaves, gametophytes, sporophytes, pollen, and microspores.

The tomato plant can be of a cultivated genetic background or a wild tomato genetic background.

As used herein, the term "tomato" refers to a plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium,* or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into S. 'N *peruvianum*' and S. 'Callejon de Hueyles', *S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense,* and *L. pimpinellifolium* may become *S. pimpinellifolium.*

Generally a cultivated tomato refers to tomato which is suitable for consumption and meets the requirements for commercial cultivation, e.g. typically classified as *Solanum lycopersicum*. In addition to the tomato plants themselves, and the parts thereof suitable for consumption, such as the fruit, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

The present invention is aimed at using any tomato cultivars, such as of domestic use, fresh market tomatoes and processing tomatoes.

The choice of the variety depends on market demand, regional adaptability, disease resistance and the end use of the product. Exemplary segments for fresh market tomatoes include, but are not limited to, Beef (fruit weight of about 220-400 gr), Standard (fruit weight of about 160-220 gr) and Cluster (uniform fruit weight of about 120-180 gr). Such varieties are available from major seed companies e.g., Grodena, Macarena, Estatio, Zouk, Climbo and Climstar, all available from Syngenta. Other varieties can be proprietary or available from other vendors, including but not limited to, Cherry-micro (up to 5 gr) round cherry, mini round cherry (7.5-15 gr), mini plum elongated cherry (10-25 gr). Examples for these varieties are: Creativo (Clause), Batico (Nirit seeds), Shiren (Hazera Genetics). Cocktail round and elongated (25-40 gr): Romanita, Cherry and Cocktail with red, yellow, orange, pink, zebra, chocolate background. Examples include, but are not limited to, Summer sun (Hazera Genetics), Black pearl (Burpee) Tyty (Tomodori). Roma determinate and indeterminate. 120-200 gr. Examples for the intermediate marker include, but are not limited to, lancelot (Vilomorin) and Parsifal (Vilomorin). Pink tomato divided to beef (220-400), standard (160-220) and cluster (120-180). Example: Momotaro type, Cor di bue tomato, (150-350 gr), Pinton (250-300 gr), open field tomato-determinate or semi-determinate (180-400 gr).

Exemplary cultivars of processing tomatoes include, but are not limited to, Roma, SUN 6366, AB 2, Heinz 9780, Heinz 9557, Halley 3155 and Hypeel 303.

There are 2 major types of tomato growth: determinate and indeterminate. Determinate growth produces "bush" tomatoes and which are bred for compactness. The entire plant stops growing once the terminal fruit ripens, the remainder of the fruit all ripen nearly simultaneously, and then the plant dies. Indeterminate growth produces tomatoes that can grow up to 10 feet in height (so-called "vining" tomatoes) and will only stop growing when killed (e.g. by frost). Their fruits ripen sequentially. In a typical plant, all growth arises from the reiteration of modular sympodial units that each produce three leaves and a multiflowered inflorescence. Most field-grown varieties of tomato, including M82, are determinate plants whose shoots produce an average of six sympodial units, each harboring a single inflorescence, within which leaf number gradually decreases before a precocious termination of growth. In general, determinate tomatoes are suitable for open field production. Semi-determinate and indeterminate "cultivated" varieties are suitable for staked cultivation in the open field or protected nets and for glasshouse cultivation.

According to an embodiment of the invention the tomato plant is a determinate tomato.

According to an embodiment of the invention the tomato plant is an indeterminate tomato.

According to an embodiment of the invention the tomato plant is a semi-determinate tomato.

According to an embodiment, the tomato is selected from the group consisting of a single fruit per truss, branched tomato and cherry tomato.

As used herein "pepper" refers to the cultivated species "*Capsicum* (hereinafter, referred to as "C") *annuum*", or wild species "*C. pubescens*", "*C. baccatum*", "*C. chinense*", and "*C. frutescens*". Moreover, "pepper" is a concept that encompasses plants called by names other than "pepper", e.g., horticultural crops called "piment", "paprika", and "sweet pepper".

As used herein "eggplant" refers to the cultivated species "*Solanum* (hereinafter, referred to as "S") *melongena*" or wild species "*S. incanum*", "*S. torvum*", "*S. nigrum*", "*S. aethiopicum*", "*S. macrocarpon*", and "*S. quitoense*".

It will be appreciated that the terms "parthenocarpy", "parthenocarpic fruit formation" "seedlessness" and "fertilization-independent fruit formation" are used interchangeably herein.

As used herein "parthenocarpy" refers to fruit production in the absence of fertilization. Hence, the parthenocarpic fruits according to some embodiments are characterized by no or less than 5 seeds per fruit.

Maintenance of sexual reproduction capability is evident upon the production of seed bearing fruit.

For example, in tomato seed-bearing fruits are considered as at least 10 seeds per fruit or at least 15% of the seeds produced in the same cultivar when carrying the wild type allele of SlAGL6.

Facultative parthenocarpy refers to seedless fruit formation under fertilization restrictive conditions such as abiotic stress conditions e.g., temperature stress i.e., heat or cold stress, humidity, light intensity that can be acute or chronic.

In general, deviation of 5-15° C. from the optimal temperature hamper fertilization dependent fruit set.

According to some exemplary embodiments, the mean daily temperature range for stable fruit set is provided as follows: 13-25° C. for tomato, 16-25° C. for eggplant, and 18-25° C. for sweet pepper (as reviewed by: Karapanos et al 2008, Kawasaki 2015). Consequently, cold stress relate to such low temperatures that prevent viable pollen production. For most tomato cultivars it means temperatures below 10° C. for over 3-4 h during the night, but reduced viability is encountered already below 12° C., especially during the post meiosis stage of pollen development, i.e. −5 to +2 days post anthesis. Temperatures below 10° C. also damage pollen adherence to stigma and its germination and pollen tube elongation (Picken 1984). Typically, heat stress occurs when temperatures rise 5-15° C. above the optimum for plant growth and development (Sato et al 2006, Mesihovic et al 2016, and references therein). In tomato, pending on the variety, day temperature of above 36° C.-38° C. for 2-4 h and night temperatures of 18-20° C. and above damage the process of microsporogenesis, which is especially sensitive to heat stress with temperatures≥35° C. for 2-4 h between −9 to −5 days post anthesis and hence lead to severe reduction in fruit set (e.g. see the MP-1 line in FIG. 13A).

In pepper: the process of pollen production is sensitive to heat stress. In particular, exposure to temperatures of 33° C. during early flower development, corresponding to microspore mother cell meiosis (14-17 days before anthesis), and during late flower development, corresponding to microspore maturation, anthesis, and pollination (−2 to 0 days before anthesis) lead to most severe adverse effect on fruit set (Erickson and Markhart 2002). Pepper male fertility is severely damaged if the flower buds are exposed to 10° C. or lower. Yet fruit set is already damaged when nigh temperatures are lower than 15.5° C. or higher than 24° C. In eggplant, the crop is sensitive to low temperatures and fruit set is damaged at night temperatures of 10° C. or lower. Pollen production and fertilization are also damaged at temperatures above 35° C. during microsporogenesis (Karapanos et al 2008, Kawasaki 2015).

Thus, according to some embodiments of the invention, fruit is produced under heat and cold stress conditions as well as high humidity (>90%) or low light intensity that hamper fertilization-dependent fruit set.

Facultative parthenocarpy is of high commercial value in this case since eggplant, tomato and pepper are propagated from seeds. Alternatively or additionally fruits are generated even under abiotic stress that preferentially hamper pollen production and/or fertilization (e.g., moderately extreme temperatures, extreme high or low humidity) or any other conditions which hamper fertilization e.g., genetic male sterility.

The observed phenotypes are evident throughout various genetic backgrounds as shown in the Example section, where maintenance of fruit weight was observed in parthenocarpic fruits of (i) the segregating 2012 BC2F2 population, in the background of the determinate cultivar M82, (ii) the segregating F2 population derived from a cross between the big fruit semi-determinate cultivar Marmande and parthenocarpic 2012 plant, and (iii) R1 progenies of the CRISPR/Cas9-derived line sg1 in the indeterminate MP-1 line background.

As used herein "AGL6" refers to a transcription factor which is a key regulator gene of the transition between the state of 'ovary arrest' imposed towards anthesis and the fertilization-triggered fruit set.

When the Solanaceous plant is tomato then the AGL6 gene is SlAG6 gene i.e., Solyc01g093960 coding sequence, SEQ ID NO: 1, 2, 3.

When the Solanaceous plant is eggplant then the AGL6 gene is Sme2.5_06058.1 SEQ ID NO: 7, 8, 9.

When the Solanaceous plant is pepper then the AGL6 gene is Capana01g001334 (Chr01-44476983-44483323) SEQ ID NO: 4, 5, 6.

The skilled artisan would know how to uncover sequence information for different cultivars within the cultivated species.

As used herein, the phrase "loss-of-function alterations" refers to any mutation in the DNA sequence of a gene (in this case AGL6), which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the regulatory activity of the protein; a nonsense mutation, i.e., a mutation which introduces a stop codon in a protein, e.g., an early stop codon which results in a shorter protein devoid of the regulatory activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the regulatory activity), or in a longer amino acid sequence (e.g., a readthrough protein) which affects the secondary or tertiary structure of the protein and results in a non-functional protein, devoid of the regulatory activity of the non-mutated polypeptide; a readthrough mutation due to a frame-shift mutation or a modified stop codon mutation (i.e., when the stop codon is mutated into an amino acid codon), with an abolished regulatory activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

According to other specific embodiments loss-of-function alteration of a gene comprises both alleles of the gene. In such instances the e.g. AGL6 may be in a homozygous form or in a heterozygous form. According to this embodiment, homozygosity is a condition where both alleles at the e.g. AGL6 locus are characterized by the same nucleotide sequence. Heterozygosity refers to different conditions of the gene at the e.g. AGL6 locus.

According to a specific embodiment the loss of function mutation is in a homozygous or heterozygous form yet both encode for dis-functioning products.

According to a specific embodiment, the loss of function mutation is a deletion e.g., exon 2 of e.g., SlAG16.

According to a specific embodiment, the loss of function mutation causes a premature stop codon.

According to some embodiments, the facultative parthenocarpic plant (as used herein "the plant") of the invention exhibits at least one of:
(i) a fruit yield/plant at least about the same (e.g., 80%, 90%, 100%, 110%) as that of a non-parthenocarpic tomato of the same genetic background under fertilization permissive conditions of the non-parthenocarpic tomato;
(ii) an average fruit weight/plant at least about the same as that of a non-parthenocarpic tomato of the same genetic background under fertilization permissive conditions of the non-parthenocarpic tomato;
(iii) comprising jelly fill when the plant is a tomato plant;
(iv) at least 80% of the fruit yield being devoid of homeotic aberrations; and
(v) enlarged ovules in the red seedless parthenocarpic fruit.

As used herein "about the same" refers to ±10% or 20%, at the same developmental stage and under the same conditions.

As used herein "fruit yield" refers to the total weight of the marketable harvested fruit, which is the product of the number of fruits per plant multiplied by the average weight of the harvested fruits.

The "same genetic background" refers to at least 95%, 96%, 97%, 98%, 99% or 99.9% of the genome is shared between the plant and the non-parthenocarpic plant.

As used herein "jelly fill" refers to the fluid to semi-fluid filling in the locular cavity of the fruit.

As used herein "homeotic aberrations" refers to developmental aberrations in the anatomic structure of the plant, e.g., floral or fruit structures, which deviate from the normal flower shape with regards to whorls number or shape of the organs comprising the wild type (WT) flower, or fruit shape, size and internal structure clearly different from that of seeded fruit, besides the lack of normal seeds, which is inherent to parthenocarpy.

As used herein "enlarged ovules" refers to the small pseudo-seeds observed in mature seedless fruits (e.g. as in FIG. 4C).

However, with respect to eggplant it should be noted that the fruits are harvestable at different sizes.

According to a specific embodiment, when the plant is a determinate tomato plant the fruit yield is a yield concentration where fruits along the 4-6 stages ripe almost simultaneously.

According to a specific embodiment, the plant is of an elite line. Examples of tomato elite lines are known in the art and some of which are listed herein.

Examples of Elite pepper cultivars: include, but are not limited to, Bastille, Rampart, Bayonet, Cutlass, Lafayette, Crusader, Pageant, Rising Sun, Trifecta (Syngenta); Atir, Gilad, Serenada, Vilmorin: E5661 F1, RIFLESSI, Lussac, Vivaldi, Tyson (Hazera Genetics), Razer, E20B10015 (Enza Zaden), Alma Paprika Peppe, and others.

Examples of Eggplant elite cultivars include, but are not limited to, Hybrid cultivars: Classic, Dancer, Dusky, Fairy Tale, Ghostbuster, Nadia, Purple Rain, According to a specific embodiment, the plant is a transgenic plant (e.g., for a genome editing agent or for an RNA silencing agent, as described herein below).

According to a specific embodiment, the plant may be a transgenic plant but the transgene may not be associated with (i.e., not the cause for) facultative parthenocarpy, as described herein. For example, the transgene may function to improve biotic stress resistance, pesticide resistance or abiotic stress resistance.

According to a specific embodiment, the plant comprises a diploid genome.

According to a specific embodiment, the plant is an inbred.

According to a specific embodiment, the plant is a hybrid plant or the seed is a hybrid seed, where e.g., each of the parental lines is homozygous for a loss-of-function mutation in AGL6 as described herein.

Methods of producing the plant as described herein may rely on the use of mutagens e.g., EMS or genetic engineering which is naturally a more directed method and therefore involves less breeding steps.

Thus, according to an aspect of the invention there is provided a method of producing the plant as described herein, the method comprising down-regulating expression or activity of AGL6 gene in the plant.

Following is a non-limiting description of methods of inducing loss-of-function mutation(s) in the AGL6 gene which can be used to produce the plant.

Thus, according to some embodiments of the invention, down-regulating AGL6 is effected by treating the plant or a regenerative portion thereof with a mutagen. In such a case the plant is non-genetically modified with an agent for inducing down-regulation of AGL6.

Alternatively or additionally, occurrence of the genetic event responsible for the facultative parthenocarpic trait may be achieved by exposing a plant (i.e., tomato, pepper, eggplant) or part thereof to a chemical or physical mutagen (as described in the Examples section). Examples of chemical mutagens include, but are not limited to nitrous acid, alkylating agents such as ethyl methanesulfonate (EMS), methyl methane sulfonate (MMS), diethylsulfate (DES), and base analogs such as 5-bromo-deoxyuridine (5BU). Physical mutagens include radiation (e.g. fast neutron, gamma radiation).

Initial exposure is typically followed by additional steps of selfing, selection, crossing and selfing or combinations thereof, where any step can be repeated more than once, as long as the loss-of-function in the AGL6 gene is in a homozygous form. Selection can be phenotypic or using marker-assisted breeding as further described hereinbelow.

According to another specific embodiment, the non-genetically modified plant of the invention results from a spontaneous genetic event incurred by multiple crossings/selfings.

Below is a description of platform technologies for effecting knock-out (also referred to as "genome editing") and transcriptional silencing in plants.

Methods of introducing nucleic acid alterations to a gene of interest (in this case AGL6) are well known in the art [see for example Menke D. Genesis (2013) 51:-618; Capecchi, Science (1989) 244:1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Any of the below methods can be directed to any part of the AGL6 gene as long as a loss-of-function is achieved. In specific embodiments, the agent is directed to the nucleic acid portion encoding the c-terminus part of the gene corresponding to SlAGL6 amino acid coordinates aa 172-252, which are distinctive for tomato, eggplant and pepper. Alternatively or additionally, the agent is directed to other portions of the gene e.g., positions encoding AA 71-80 as described in the Examples section. Other examples are provided in the Examples section which follows.

When needed further steps of selfing are effected in order to achieve a homozygous form of the mutation.

As used herein "target sequence" refers to the AGL6 DNA coding or RNA transcript. It will be appreciated that AGL6 can also be down-regulated at the protein level using an AGL6 antibody or chemical inhibitor. Although this option is not discussed here at length, it is still considered an embodiment for producing the plant.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8, 163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically, a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, C A).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

Another agent capable of downregulating AGL6 is a RNA-guided endonuclease technology e.g. CRISPR system (that is exemplified in great details in the Examples section which follows).

As used herein, the term "CRISPR system" also known as Clustered Regularly Interspaced Short Palindromic Repeats refers collectively to transcripts and other elements involved in the expression of or directing the activity of CRISPR-associated genes, including sequences encoding a Cas9 gene (e.g. CRISPR-associated endonuclease 9), a tracr (trans-activating CRISPR) sequence (e.g. tracrRNA or an active partial tracrRNA), a tracr-mate sequence (encompassing a "direct repeat" and a tracrRNA-processed partial direct repeat) or a guide sequence (also referred to as a "spacer") including but not limited to a crRNA sequence (i.e. an endogenous bacterial RNA that confers target specificity yet requires tracrRNA to bind to Cas) or a sgRNA sequence (i.e. single guide RNA).

In some embodiments, one or more elements of a CRISPR system is derived from a type I, type II, or type III CRISPR system. In some embodiments, one or more elements of a CRISPR system (e.g. Cas) is derived from a particular organism comprising an endogenous CRISPR system, such as *Streptococcus pyogenes, Neisseria meningitides, Streptococcus thermophilus* or *Treponema denticola*.

In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" in this case AGL6 refers to a sequence to which a guide sequence (i.e. guide RNA e.g. sgRNA or crRNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. Thus, according to some embodiments, global homology to the target sequence may be of 50%, 60%, 70%, 75%, 80%, 85%, 90%, 95% or 99%. A target sequence may comprise any polynucleotide, such as DNA or RNA polynucleotides. In some embodiments, a target sequence is located in the nucleus or cytoplasm of a cell.

Thus, the CRISPR system comprises two distinct components, a guide RNA (gRNA) that hybridizes with the target sequence, and a nuclease (e.g. Type-II Cas9 protein), wherein the gRNA targets the target sequence and the nuclease (e.g. Cas9 protein) cleaves the target sequence. The guide RNA may comprise a combination of an endogenous bacterial crRNA and tracrRNA, i.e. the gRNA combines the targeting specificity of the crRNA with the scaffolding properties of the tracrRNA (required for Cas9 binding). Alternatively, the guide RNA may be a single guide RNA capable of directly binding Cas.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In some embodiments, the tracr sequence has sufficient complementarity to a tracr mate sequence to hybridize and participate in formation of a CRISPR complex. As with the target sequence, a complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned.

Introducing CRISPR/Cas into a cell may be effected using one or more vectors driving expression of one or more elements of a CRISPR system such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors.

Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. A single promoter may drive expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron).

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, transformed into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After transformation and positive selection, homologously targeted clones are identified. Next, a second targeting vector that contains a region of homology with the desired mutation is transformed into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Silencing at the AGL6 transcript (RNA) level can be effected using the below exemplary platforms.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene (AGL6). In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al, Oligonucleotides, Oct. 1, 2003, 13(5): 381-392. doi:10.1089/154545703322617069.

According to an embodiment of the invention, the long dsRNA are specifically designed not to induce the interferon and PKR pathways for down-regulating gene expression. For example, Shinagwa and Ishii [Genes & Dev. 17 (11): 1340-1345, 2003] have developed a vector, named pDE-CAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the AGL6 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem-Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Constructs useful in the methods according to the present invention may be constructed using recombinant DNA technology well known to persons skilled in the art. The coding sequence constructs may be inserted into vectors, which may be commercially available, suitable for transforming into plants and suitable for expression of the gene of interest in the transformed cells. The genetic construct can be an expression vector wherein the nucleic acid sequence is operably linked to one or more regulatory sequences allowing expression in the plant cells.

Plant cells may be transformed stably or transiently with the nucleic acid constructs of the present invention. In stable transformation, the nucleic acid molecule of the present invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:
  (i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.
  (ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217;

Glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

However other methods of production are also contemplated including sexual reproduction (and selection for the phenotype whether morphologically or using molecular markers as described herein), tissue culture and more.

Micropropagation is a process of growing new generation plants from a single piece of tissue that has been excised from a selected parent plant or cultivar. This process permits the mass reproduction of plants having the preferred tissue expressing the fusion protein. The new generated plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet gradually increased so that it can be grown in the natural environment.

Viruses that have been shown to be useful for the transformation of plant hosts include CaMV, TMV, TRV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Regardless of the method used to produce the Solanaceous plant (i.e., eggplant, tomato and pepper e.g., tomato) of some embodiments of the invention, once plants or any reproductive material is at hand, it is selected for the facultative parthenocarpic trait.

Thus, according to an aspect of the invention there is provided a method of selecting a Solanaceous plant (i.e., eggplant, tomato and pepper e.g., tomato) plant being facultative parthenocarpic, the method comprising detecting in a genome of a Solanaceous plant (i.e., eggplant, tomato and pepper e.g., tomato) plant a loss of function mutation in the AGL6 gene, wherein presence of the mutation is indicative of a Solanaceous plant (i.e., eggplant, tomato and pepper e.g., tomato) having being facultative parthenocarpic.

Many methods are known in the art for analyzing for mutations including for example single base extension (SBE), allele-specific primer extension sequencing (ASPE), DNA sequencing, RNA sequencing, microarray-based analyses, universal PCR, Melting Curve SNP method, allele specific extension, hybridization, mass spectrometry, ligation, extension-ligation, Flap Endonuclease-mediated assays, restriction fragment length polymorphism (RFLP), electrophoresis, sequence alignment, allelic specific oligonucleotide hybridization (ASO) and random amplified polymorphic DNA (RAPD).

Thus, the present invention contemplates oligonucleotides (e.g. Primers) that can be used to distinguish between the mutated and non-mutated form of AGL6.

Thus, once a plant carrying the loss of function genetic alteration is identified it is considered as being facultative parthenocarpic. This plant material can be used as a breeding material in the development of Solanaceous plant (i.e., eggplant, tomato and pepper e.g., tomato) varieties having agriculturally desired traits.

According to one embodiment, the plants of the present invention are of a hybrid variety—i.e. are generated following the crossing (i.e. mating) of two non-isogenic plants both being homozygous for a loss of function mutation in the AGL6 gene. The hybrid may be an $F_1$ Hybrid.

An "$F_1$ Hybrid" as used herein, refers to first generation progeny of the cross of two non-isogenic plants.

The development of Solanaceous plant (i.e., eggplant, tomato and pepper e.g., tomato) hybrids of the present invention requires the development of stable parental lines. In breeding programs desirable traits from two or more germplasm sources or gene pools are combined to develop superior breeding varieties. Desirable inbred or parent lines are developed by continuous self-pollinations and/or backcrosses and selection of the best breeding lines, sometimes utilizing molecular markers to speed up the selection process.

Once the parental lines that give the best hybrid performance have been identified e.g., both carrying the loss of function mutation as described above e.g., in the AGL6 gene, the hybrid seed can be produced indefinitely, as long as the homozygosity of the parents are maintained. According to one embodiment the Solanaceous plant (i.e., eggplant, tomato and pepper e.g., tomato) plants of the present invention are stable parent plant lines (carrying the loss of function mutation e.g., in the AGL6 gene in a heterozygous form or a homozygous form).

As defined herein, the phrase "stable parental lines" refers to open pollinated, inbred lines, stable for the desired plants over cycles of self-pollination and planting. According to a specific embodiment, 95% of the genome is in a homozygous form in the parental lines of the present invention.

A common practice in plant breeding is using the method of backcrossing to develop new varieties by single trait conversion.

The phrase "single trait conversion" as used herein refers to the incorporation of new single gene into a parent line wherein essentially all of the desired morphological and physiological characteristics of the parent lines are recovered in addition to the single gene transferred.

The term "backcrossing" as used herein refers to the repeated crossing of a hybrid progeny back to one of the parental Solanaceous plant (i.e., eggplant, tomato and pepper e.g., tomato) plants. The parental Solanaceous plant (i.e., eggplant, tomato and pepper e.g., tomato) plant which contributes the gene for the desired characteristic is termed the non-recurrent or donor parent. This terminology refers to the fact that the non-recurrent parent is used one time in the backcross protocol and therefore does not recur. The parental Solanaceous plant (i.e., eggplant, tomato and pepper e.g., tomato) plant to which the gene from the non-recurrent parent are transferred is known as the recurrent parent as it is used for several rounds in the backcrossing protocol.

In a typical backcross protocol, a plant from the original varieties of interest (recurrent parent) is crossed to a plant selected from second varieties (non-recurrent parent) that carries the single gene of interest to be transferred. The resulting progeny from this cross are then crossed again to the recurrent parent and the process is repeated until a Solanaceous plant (i.e., eggplant, tomato and pepper e.g., tomato) is obtained wherein essentially all of the desired morphological and physiological characteristics of the recurrent parent are recovered in the converted plant, in addition to the single transferred gene from the non-recurrent parent.

Thus, near-isogenic lines (NIL) may be created by many backcrosses to produce an array of individuals that are nearly identical in genetic composition except for the trait or genomic region under interrogation in this case loss of function genetic alteration e.g., in the AGL6 gene.

Backcrossing methods can be used with the present invention to improve or introduce a characteristic into the parent lines. Marker assisted breeding (selection) as described above can be used in this method.

According to a specific embodiment, the plant or the plant seed is an inbred.

According to a specific embodiment, the plant is a hybrid plant or the seed is a hybrid seed.

The invention also relates to progeny of the tomato, eggplant, pepper plants of the invention. Such progeny can be produced by sexual or vegetative reproduction of a plant of the invention or a progeny plant thereof. The regenerated progeny plant grows fruits independent of fertilization in the same or a similar way as the facultative parthenocarpic parent. In addition to this, the progeny plant may be modified in one or more other characteristics. Such additional modifications are for example effected by mutagenesis or by transformation with a transgene.

As used herein the word "progeny" is intended to mean the offspring or the first and all further descendants from a cross with a plant of the invention that shows fertilization independent fruit formation. Progeny of the invention are descendants of any cross with a plant of the invention that carries the mutation (in a homozygous form) trait that leads to fertilization independent fruit formation.

"Progeny" also encompasses plants that carry the trait of the invention which are obtained from other plants of the invention by vegetative propagation or multiplication.

As mentioned, embodiments described herein, furthermore, relate to hybrid seed and to a method of producing hybrid seed comprising crossing a first parent plant with a second parent plant and harvesting the resultant hybrid seed. In this case the trait is recessive, therefore both parent plants need to be homozygous for the fertilization independent fruit formation trait in order for all of the hybrid seed to carry the trait of the invention. They need not necessarily be uniform for other traits.

Embodiments described herein also relate to the germplasm of the plants. The germplasm is constituted by all inherited characteristics of an organism and according to the invention encompasses at least the facultative fertilization independent fruit formation trait of the invention.

Embodiments described herein also relate to cells of the plants that show the facultative fertilization independent fruit formation trait. Each cell of such plants carries the genetic information (i.e., loss of function mutation in AGL6) that leads to the facultative parthenocarpy. The cell may be an individual cell or be part of a plant or plant part, such as the fruit.

The present teachings further relate to consumed products which comprise the genomic (DNA) information (i.e., loss of function mutation in AGL6) that leads to the facultative parthenocarpy.

Fruits of any of the plants described herein may be selected or qualified for fruit color, Brix, pH, sugars, organic acids and defect levels (insect damage, mold, etc.) at ripening or post harvest. For example, tomatoes are typically transported to a large processing facility, where they are collected and where they may subsequently be washed, typically using chlorinated water and rinsed using tap water and further selected to remove those that present defects (e.g., inadequate ripening, disease damage, molds etc.). Tomatoes may be stored (especially those exhibiting improved shelf-life as described above) or immediately sent to the consumer (fresh-market tomatoes). Processing tomatoes may be processed into a wide variety of products.

For juice or pulp production, the tomatoes may be subject to oven dehydration and are comminuted and macerated (disintegrated and broken) to obtain a pumpable mass. As will be clear to the skilled person these operations per se are known and common in the field of tomato processing and any adjustments to the method can be made in this regard without departing from the scope.

Methods for processing tomatoes and/or producing tomato-based compositions are well known in the art, see generally U.S. Pat. No. 6,924,420. Also reported are specific methods for preparing, for example, paste (U.S. Pat. No. 7,074,451), sterile paste (U.S. Pat. No. 4,206,239), puree (U.S. Pat. No. 4,556,576), sauce (U.S. Pat. No. 7,122,217), solidified sauce (U.S. Pat. No. 4,038,424), barbecue sauce (U.S. Pat. No. 6,869,634), salsa (U.S. Pat. No. 5,914,146), ketchup (U.S. Pat. No. 6,689,279), tomato fiber composition (U.S. Pat. No. 7,166,315) and dehydrated tomato-product (U.S. Pat. No. 5,035,909). Methods of modifying the texture and consistency of tomato paste, pulp, and puree has also been reported, see, for example, U.S. Pat. No. 6,720,019.

Also provided is an edible processed tomato product comprising the tomato or an edible portion thereof (e.g., fruit or an edible part thereof).

Also provided is a tomato paste generated according to the present teachings.

Examples of such edible products include, but are not limited to, canned tomatoes (whole), a tomato paste, a ketchup, a tomato sauce a tomato soup, a dehydrated tomato, a tomato juice, a tomato powder, a tomato dice, a crushed tomato, a chopped tomato and a tomato concentrate.

Pepper products that can benefit from seedlessness include: varieties for fresh consumption, as well as for processed and preserved pepper. Cultivars grown for spices (paprika) production consist of dried, ground pods of *Capsicum annuum* L., sweet red pepper. Sweet paprika spice processing includes removal of the seeds before grinding of the pericarp, which is otherwise of reduced quality. Other products are made from paprika oleoresin, an oil-soluble extract from the fruits of *Capsicum annuum* which is primarily used as a colouring and/or flavouring in food products. It is also used to colour cosmetics products including bath and beauty products and moisturizing lipstick.

Seedless eggplant are in great demand by the consumers as the seeds add bitterness and are associated with fruit flesh browning. Eggplant is consumed usually following cooking, backing, frying, or roasting. It is also consumed pickled or as dried, and dried baby eggplant skins serve for stuffing. It is also consumed as processed products like frozen entrees and specialty dips.

According to some embodiments, the products comprise the DNA (carrying a loss of function mutation in the AGL6 gene causing the facultative parthenocarpic phenotype) of the tomato, pepper or eggplant (e.g., paste, dried fruit, juice and the like)

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Screening the EMS induced M2 population for yielding under extreme temperatures: Each of the ca. 1000 $M_2$ EMS mutagenized families was represented in the field by 12 plants divided between two replicates, each consisting of 6 plants and planted in a separate block. The parental line M82, serving as a control, was similarly represented by 6 plants replicates, at least once per each of the 22 double rows planted in the field. Seedlings were planted in the field in the late summer (Jul. 7, 2009), and the field was repeatedly screened starting August 12, for fruit set and development during the very hot months of August-September. Single plants from several families were found to set parthenocarpic fruits, yet except for the chosen mutation 2012 and another one that yielded big parthenocarpic fruits but of somewhat distorted shape of theirs distal (style) end, all the others set relatively small (less than 35 g) seedless fruits, presumably representing mutations, which only partly compensate for the contribution of the seeds to fruit development to its full potential.

Generation of populations for mapping and analysis of the 2012 mutant: 2012 $BC_1F_2$ population: The $BC_1$ was generated by pollinating M82 emasculated flowers with pollen collected from the 2012 plant, these were grown and allowed to self to generate $BC_1F_2$.

Test-cross (TC) population: Several 2012 $BC_1F_2$ plants manifesting WT phenotype, i.e. not parthenocarpic were emasculated and pollinated with pollen collected from a parthenocarpic sibling. About 100 progenies from each of three of these crosses were planted in the summer of 2013 (17 Jun. 2013). One of the $F_1$ populations was identified as a TC population since it manifested a clear 1:1 segregation for the parthenocarpic phenotype, when yielding under the high temperatures prevailing during the late summer in the net-house. This population served for the analysis summarized in Table 2.

2012 $BC_2F_2$ population: One of the plants from the $BC_1F_2$ population showing a clear parthenocarpic phenotype was used to pollinate the parental line M82, the $F_1$ plants were grown and selfed to generate $BC_2F_2$.

$F_2$ population derived from 2012×Marmande cross: Pollen of a parthenocarpic 2012 $BC_1F_2$ plant served to pollinate emasculated flowers of the medium-large, multi-locules fruit, open variety Marmande (www(dot)rareseeds(dot)com/marmande-tomato/). $F_2$ seeds were collected from selfed $F_1$ plants.

Growth and Phenotyping 2012 $BC_2F_2$ plants grown under nearly ambient conditions: Towards the end of the winter (26 Feb. 2014), 498 $BC_2F_2$ plants were planted in a none-heated net-house, together with plants from the parental line M82. At the beginning of May 2014, some of the $BC_2F_2$ plants were already bearing red and even red-ripe fruits. Hence the first round of phenotyping was performed on the 13-15 of May 2014. All the plants that could not be categorically phenotyped at that time were re-sampled several times later on to establish whether they are parthenocarpic or not. Since the 2012 mutation was found to cause a strong yet facultative parthenocarpy, a stringent protocol was set for phenotyping the progenies, especially as they grew and set fruit under nearly ambient conditions. From each plant were picked the 6-8 most ripen fruits. If there were none, as in the control and most of the $BC_2F2$ plants, the six largest green fruits were picked. These were photographed, cut transversely and the presence or absence of seeds was recorded. Plants bearing big, usually red seedless fruits were defined as parthenocarpic, even if some of the other picked fruits contained few seeds. Plants were defined as non-parthenocarpic, based on seed bearing and the size of the fruits.

All the plants that could not be categorically phenotyped upon the first screen were re-assessed at least two times at later dates. Plants that did bear clear parthenocarpic fruits were defined as parthenocarpic even if they set also nice seeded fruits, plants were defined as non parthenocarpic if delayed in fruit development, and most importantly, setting only seeded fruits, even if the number of seeds per some of their fruits was low.

For the analysis of yield parameters including yielding potential (presented in FIGS. 5A-C), the plants were allowed to grow for another month. On 10-11 Jun. 2014 all the mature green, breaker and red fruits from each of 10-13 plants per SlAGL6 (SNP No. 3) genotype were harvested. For each plant, were determined the number and weight of all the harvested fruits, and the number and weight of the red fruits. To reduce environmental effects on yielding, fruits were not collected from plants located at the ends of the rows.

Growth and phenotyping 2012 $BC_2F_3$ families: From each of the 2012 $BC_2F_2$ homozygous for mutated SlAGL6, seeds, if produced, were collected. Progenies derived from three such plants that did not manifest parthenocarpic phenotype (see Table 3), were planted on the 22 Oct. 2014 in a non-heated net house, side by side with progenies of four plants defined as clear parthenocarpic. These plants grew during the very harsh winter of 2015. Fruits were collected and assessed for seed bearing on 26 Mar. 2015.

SNPs genotyping of 2012 derived progenies: Genotyping was performed as a service by DYN R&D Ltd, Sagi Industrial park, Migdal-Haemek, Israel, following the Melting Curve SNP (McSNP) method (Ye et al., 2002). To confirm the reliability of the DYN R&D analyses, DNA derived from 9 TC plants, and the parental line M82, served as template for PCR amplification of sequences flanking each of the 6 SNPs (Table 1, column 2). The same results were obtained from traditional sequencing of the PCR products and parallel genotyping by DYN R&D for all the six SNPs in all the tested DNA samples. As a routine from each young plant established and numbered in the net-house, four leaf pieces were sampled. Each plant was genotyped twice, i.e. on two of the four sampled leaves, and the analysis was performed as "double-blind". In the rare cases where the duplicates genotyping was inconsistent, the two other duplicates, and if necessary new samples from the questionable plants were genotyped to positively establish the SNP genotype in each of the analyzed plants.

Genomic DNA libraries generation and sequencing: From each of 20 plants derived from 2012 $BC_1F_2$ population, defined as "strong parthenocarpic" one young leaf (ca. 150 mg FW) was picked and from the pool of the 20 leaves DNA was extract. Similarly, DNA was extracted from a pool of 23 leaves sampled at the same date from 23 "non parthenocarpic" plants. The DNA samples were sent to the Technion, (The Life Sciences and Engineering Infrastructure Center) Haifa, Israel, to prepare the two sequencing libraries, one was designated '2012 library' and the other 'NP (non-parthenocarpic) library'. The libraries were sequenced using 100 bp paired end reads on an Illumina HiSeq 2000 platform. The raw sequence data, comprising 15.4 Gbp and 15.9 GBp respectively, was filtered using Trimmomatic to remove adapter and low quality sequence (below Q10) (Bolger et al 2014). The resulting datasets were aligned using BWA (Li and Durbin 2009) against the M82 sequence (Bolger et al 2014). The alignments were filtered to remove ambiguous, secondary, or pairwise discordant alignments. The remaining high quality alignments where then used with SAMtools (Li et al 2009) to generate a 'read pileup' for the parthenocarpic and non-parthenocarpic pools. Custom scripts were used to interpret the pileup, and identify genomic locations where the pools differed substantially. These regions were then plotted and used to identify a 10.4 Mbp region on chromosome one, from 75.8 Mbp to 86.2 Mbp, which most likely contained the causal mutation. It was possible to identify 19 high-confidence mutations within this window which were unique to the phenotypic pool. The sequence around each mutation was extracted and mapped using BLAST to the Heinz genome. The majority of the mutations were intergenic or in introns. Of the total of 4 which hit exons, 2 were synonymous changes and 2 were non-synonymous changes with minor effect (Valine to Isoleucine). In addition, the functional annotation the affected genes did not suggest an obvious connection to the observed phenotype.

To improve the analysis, another lane was sequenced from each of the two libraries. Furthermore, to ensure background differences between the published M82 and local M82 lines did not affect results, the parental M82 line was also sequenced. These datasets comprised 39.6 Gbp, 38.1 Gp and 31.5 Gbp of data for the 2012 library the NP library and the parental M82 line, respectively. All datasets were trimmed using Trimmomatic as before, and the 2012 and NP pools were combined with the previously sequenced data. Reads from the parental line was aligned using BWA and almost 30K high-confidence variants were called using SAMtools. These variants were applied to the public M82 sequence to create the parental M82 genome sequence.

The new and existing parthenocarpic and non-parthenocarpic datasets were then aligned using BWA against the newly determined parental M82 genome, and processed as before to determine genomic locations were the pool differed substantially. The larger dataset allowed the causal window to be narrowed to a region spanning from 76.67 Mbp to 80.73 Mp on chromosome 1, which corresponds to a region spanning from 84.9 Mbp to 89.0 Mbp on the Heinz genome. Nine high confidence mutations, unique to the parthenocarpic pool were identified within the window. These were mapped as before to the Heinz genome to determine the corresponding locations, as shown in Table 1. Surprisingly, the strongest candidate mutation from this analysis, which caused an early stop codon in Solyc01g093960, was not clearly detectable in the original dataset, since it was present at 57% (8 of 14 reads) in the non-phenotypic pool, far above the 33% expected.

Construction of a CRISPR/Cas9 Knockout Plasmid, and Tomato Transformation:

The CRISPR/Cas9 construct was designed to create a deletion after 212 bp of the Solyc01g093960coding sequence (predicted exon 2, after 70 aa, see FIG. 2B). The 20 bp target sequence was chosen to be followed by protospacer adjacent motif (PAM), the requisite binding site for Cas9, TGG (depicted in FIG. 2B). The selected sgRNA was amplified using the primers: SalI-gRNA-F: AGAgtcgacAT-AGCGATTGAGGATTAAGGCAACAACGTGTTT-TAGAGCTAGAA ATAGCAAG, (SEQ ID NO: 10) and HindIII-gRNA-R: TAAGCTaagcttC-GATCTAAAAAAAGCACCGACT (SEQ ID NO: 11) (the added restriction sites are presented in lowercase letters, the specific target sequence (cRNA), is underlined in the SalI-gRNA-F primer sequence). The PCR product was restricted and cloned into the pRCS binary vector SalI-HindIII sites under the control of the synthetic *Arabidopsis* U6 promoter (Waibel and Filipowicz, 1990), alongside the plant codon-optimized version of Cas9 (Li et al., 2013). The Cas9 protein was expressed under the constitutive 35S promoter as a fusion to a nuclear localization signal (NLS) at both protein termini and FLAG tagged at its N-terminus. The binary vector was transformed to *Agrobacterium tumefaciens* strain EHA105, which served to transform the indeterminate tomato line MP-1 by co-cultivation with cotyledons dissected from 10 days old sterile seedlings as previously described, not more than one regenerated shoot was selected per transformed cotyledon (Barg et al 1997).

Detection of CRISPR/Cas9 Induced Mutations

The Solyc01g093960 gRNA target site was designed to include AclI restriction enzyme site (AACGTT, SEQ ID NO: 12) overlapping three bp upstream from the PAM (see FIG. 2B), the predicted cut site of the Cas9 nuclease, so that the DNA double-strand break (DSB) repair could disrupt the restriction site. $R_0$ plants were screened for the presence of chimeric section carrying mutated target site. To increase the probability of detecting Cas9 generated mutation which occurred at later developmental stages of the regenerated $R_0$ plants, genomic DNA was extracted from leaves younger than number 10-12 on the main stem. DNA was amplified using specific primers: 2012-F: 5'-GCCTT-GAAATCAGTAAGAGTATTGG-3' (SEQ ID NO: 13) and 2012-R: 5'-GTTCGTTGAAGTGCTTCAAACTTGG-3' (SEQ ID NO: 14), to result in a 354 bp fragment flanking the sgRNA target sequence. Unless mutated, its digest with AclI results in two bands of similar size (170/184 bp, see FIG. 2B). The digested amplicons were subjected to gel electrophoresis. DNA was extracted from the gel at the position of the uncut band, that even when no clear band was visualized under UV light. The extracted DNA was precipitated O/N at −20° C. (0.3M Na-Acetate pH=5.2, 2.2V ethanol and 1 µg glycogen), re-suspended in 10 µL water, from which 1 µL served as a template for amplification using the same pair of primers. To test for loss of the restriction site and the nature of the mutation generated, the amplified band was both restricted with AclI and sequenced, using both the forward and reverse primers. In most of the $R_0$ plants found to contain a mutated version, the AclI resistant PCR band was much fainter than the restricted double band, strongly suggesting that the mutated version was generated late rather than at the initial stages of the $R_0$ plants regeneration. The same procedure was applied to genotyping $R_1$ progenies.

Loss or maintenances of the cas9/sgRNA cassette in the progenies was PCR tested using the pair of primers: cas-F CGACAATCTGATCCAAGCTCA (SEQ ID NO: 15) and pRCS_val_rev: CGACAATCTGATCCAAGCTCA (SEQ ID NO: 16)

Analysis of Sg1 and MP-1 Yielding Under Heat Stress

The experiment was performed in four replicate, each consisting of 17-27 plants per genotype. Plants were planted in a net-house on 20 Apr. 2016 and the first harvest was performed on the 26 Jun. 2016 (see FIGS. 13A-H). All the red fruits of each replicate were harvested, and weighed. Fruit weight and fruit number per plant were calculated from the weight of 6-8 batches of 30 fruits each per replicate. The data presented in FIGS. 13A-H were calculated per plant, since the plants' number varied among replicates. Brix was measured on juice squeezed from two pools of three red ripe fruits, per replicate (following Carmi et al., 2003). pH was measured on two pools of crashed 6-8 red ripe fruits per replicate.

Example 1

Identification of Line 2012 as a New Monogenic Recessive Mutant for Parthenocarpy Derived from EMS Mutagenized M82 Population A chemically mutagenized $M_2$ population generated in the M82 cultivar, by imbibing seeds in EMS solution (population generated by J Hirschenhoren and Y. Kapulnik, The Volcani Center, ARO) was screened for mutants yielding under extremely high temperatures, as described in Materials and Methods. Family No. 2012 included two plants, each coming from a different replicate (see in Materials and Methods), that set nice parthenocarpic fruits with good jelly under these conditions, whereas the parental line plants set at the most some tiny, hollow "nuts" fruits.

The pollen of one of these two plants served in pollinating emasculated flowers of M82 plant, which set seeded fruits. These $BC_1$ plants were not parthenocarpic. However 7 out of 40 $BC_1F_2$ progenies set seedless fruits under the extremely hot conditions prevailing in the late summer of 2010, when the parental line M82 managed to set tiny "nuts" fruitlets only (FIGS. 1A-C vs. 1D-F). Thus, indicating that the trait is heritable, and behaves as a single recessive mutation. Further, plants from the same $BC_1F_2$ population were grown also in the winter in a non-heated glass house, which glass windows were kept constantly open. Under these cold conditions 9 out of the 30 $BC_1F_2$ progenies tested set seedless fruits, whereas the rest of the siblings set no normal fruits, indicating that the mutation enables parthenocarpic fruit development also under temperatures too low to allow fertilization dependent fruit set.

Example 2

NGS Assisted Mapping of the 2012 Mutation

To map the mutation, the bulk segregation approach (Michelmore et al 1991) was chosen. Deep sequencing was performed on two genomic libraries one coming from a bulk of 2012 $BC_1F_2$ parthenocarpic siblings and the other from their non-parthenocarpic siblings.

The facultative nature of the 2012 parthenocarpy together with plausible interaction with other EMS induced mutations affecting the manifestation of the trait could result in contamination of the parthenocarpic library with DNA derived from falsely phenotyped non-parthenocarpic sibling. Thus several measures were taken to try nullify this risk: First, 105 plants from the 2012 $BC_1F2$ population were grown in the late summer of 2011 in a net house, since usually from mid-July to late August the temperatures are high enough to seriously damage microsporogenesis and hence prevent fertilization dependent fruit development. On Sep. 27, 2011 the fruits were harvested, examined, and each plant was phenotyped. The parthenocarpic phenotype was determined based on yielding nice parthenocarpic fruits with good jelly fill (e.g. FIG. 1G). Besides bearing seedless fruits (alongside few seeded fruits in some of the plants phenotyping plants as "strong parthenocarpic" was based on additional visual parameters recorded along the growing season including, maintenance of petals around the developing fruit, earliness of fruit development post anthesis, number of fruits per plant, number of fruits per truss, as well as fruit size and shape. Sibling plants were characterized as non-parthenocarpic (NP) if no seedless normal size fruits developed (just "nuts" i.e., small deformed seedless hollow "Puffy" fruits, FIG. 1H). Under these conditions, the difference in fruit weight and stage of ripening between these two sub-populations of $BC_1F_2$ was very significant (FIG. 1I).

The genomic library coming from a pool of 20 $BC_1F_2$ plants characterized as "strong parthenocarpic" was designated '2012 library', and the other coming from a pool of 23 of their siblings characterized as "strong non-parthenocarpic", was designated 'NP (non-parthenocarpic) library' (as described in Materials and Methods). The filtered reads derived from each of the two sequenced libraries, were aligned to the M82 genome sequence and analyzed for regions enriched in homozygous mutated nucleotides in the 2012 library while comprising only about 33% of the reads in the NP library, that should contain the corresponding WT nucleotide in the other ca. 66% of the reads. Bioinformatics analysis was performed as described in Materials and Methods. The results of this analysis pointed to a segment of 3.85 million nucleotides in chromosome 1, spanning between SL2.5ch01:85115654-88965277, as the likely location of the mutation (Table 1). The analysis revealed nine homozygous mutated SNPs in this region in the '2012 library', that were heterozygote in the 'NP library', i.e. only 42-24% of the reads in this library showed the mutated allele, while the others included the expected WT allele. Interestingly, two of the mutated SNPs found in this region appear to result from transversion rather than the typical EMS induced transition type of point mutations (Anderson 1995. Methods Cell Biol.; 48:31-58.). However, EMS induced transversions in plants were reported before (e.g. Galpaz et al 2013, Ghio et al 2013).

Example 3

Marker Assisted Refined Mapping of the 2012 Mutation

In attempt to restrict the location of the mutation underlying the 2012 mutant, co-segregation of six SNPs dispersed along the chromosomal interval suggested as the mutation location (Table 1, column 2), with the parthenocarpic phenotype was examined in a test cross (TC) population, (Generated as described in Materials and Methods). This population was allowed to set fruit under heat stress, late in the summer of 2013. Genotyping of the TC population for each of the six candidate SNPs specified in Table 1, column 2, was performed as a service by DYN R&D, Israel. (see Materials and Methods).

Table 2 summarizes the phenotyping and genotyping results of this TC population for the six point mutations. This analysis indicated that SNPs No. 1,5 and 6 are not linked to the mutation. On the other hand, for SNPs No. 2, 3 and 4, a tight, though not absolute, link was found between the mutations and the phenotype (Table 2). This analysis indicated that either none of these SNPs resides in the gene responsible for the 2012 mutation, or that there was a problem in phenotyping some of the plants, possibly due to the dragging of other mutations that might obscure the parthenocarpic phenotype. Nevertheless, the results of this analysis decreased the region in which the mutation resides to less than 700,000 nt, spanning from SNP No. 2 to No. 4 (Tables 1, 2 below).

To further zoom in on the location of the mutation, a 2012 $BC_2F_2$ population generated as described in Materials and Methods, was similarly analyzed for co-segregation of the parthenocarpic phenotype with the mutated version of SNPs No. 2 and 3. These SNPs were chosen because in the analyzed TC population they showed somewhat tighter linkage with the trait than SNP No. 4 (Table 2, below). The $BC_2F_2$ population carries-over less non relevant EMS induced mutations than the above described test-cross population, especially less homozygous mutated SNPs, and should include more recombinants among the SNPs surrounding the 2012 mutation. Unlike the $BC_1F_2$ and the TC populations, that were phenotyped under extremely high temperatures, to hasten the analysis, the $BC_2F_2$ population was tested under near-ambient condition in the spring of 2014 as detailed in Materials and Methods. The results of this analysis are summarized in Table 3. This analysis eliminated SNP No. 2 as a candidate, since six non-parthenocarpic plants were homozygous for its mutated version.

The fact that there was not a complete linkage between the parthenocarpic phenotype and the mutated SNP No. 3, suggested that the mutation might reside between SNP No. 3 and No. 4. Hence the plants homozygous for mutated SNP No. 3, were genotyped also for SNP No. 4. However the finding that the three plants phenotypes as non-parthenocarpic were homozygous also for the mutated SNP No. 4 (Table 3, below), did not support this notion. The heritability of this "deviation" was tested in their progenies, i.e., in $BC_2F_3$ populations. Progenies of the three plants homozygous for SNP No. 3, which were not parthenocarpic, were planted late in autumn side by side with progenies of four $BC_2F_2$ plants that manifested clear parthenocarpy, and allowed to set fruit under sub optimal temperatures as described in Materials and Methods. In all the seven $BC_2F_3$ families, all the plants did bear clear parthenocarpic fruits.

Taken together, these analyses strongly suggested the mutated AGL6 as the gene underlying the parthenocarpic mutation 2012. SlAGL6 encodes for a MADS box protein (FIG. 2A) belonging to the MEF2 (myocyte enhancer factor 2)-like/Type II subfamily of MADS box proteins (Smaczniak et al 2012).

Example 4

CRISPR Based Verification of Mutated SlAGL6 as the Gene for the 2012 Parthenocarpy To confirm that the mutated AGL6 is the gene underlying the 2012 parthenocarpy, CRISPR technology was exploited to knockout the SlAGL6 gene Solyc01g093960.

Synthetic gRNA was designed to target the second exon of Solyc01g093960 (FIG. 2B). It was incorporated into a CRISPR/Cas9 knockout binary vector and transformed into tomato line MP-1, as detailed in Materials and Methods. The $R_0$ plants were tested for presence of mutated version of SlAGL6 as described in Materials and Methods. Out of 18 $R_0$ transgenic plants analyzed 11 (61%) carried mutated versions at the expected site in the tested amplified DNA samples, as expected from DNA repair by non-homologous end joining at the CAS9 digestion site (Lieber 2010). Fruits were collected from all the 11 plants; three of them did bear seedless fruits only, while the others did bear both seeded and seedless fruits. The final proof for allelism of the 2012 mutation and the CRISPR induced mutations in SlAGL6 was provided showing (FIG. 11) that $F_1$ hybrid between plant homozygous for the 2012 mutated allele of SlAGL6 and plant homozygous for the sg1 mutated allele produced seedless fruits, whereas a hybrid between the same 2012 plant and MP-1 (homozygous for Wild-Type allele of SlAGL6) produced seeded fruits only.

Example 5

CRISPR Derived AGL6 Mutated $R_1$ Progenies are Parthenocarpic

Progenies of three $R_0$ plants designated sg1, sg4 and sg5 differing in the nature of their mutation but all leading to premature stop codon (Table 4), were chosen for analysis of their ability to set parthenocarpic fruits. Since these mutations result in a premature stop codon, the aberrant mRNA transcribed from these mutated genes is expected to be destroyed via the Nonsense-Mediated Decay (NMD) RNA surveillance machinery (e.g. Chang et al. 2007; Drechsel et al. 2013; Degtiar et al 2015).

If the destruction is not complete, the mutated mRNA would translate to the truncated AGL6 proteins depicted in Table 4, below. For mutation sg1, if translated, two different products are expected pending if deletion of the 3' end of intron 1 and the first nt of intron 2, results in splicing out all of exon 2, or if the truncated intron 1 is not spliced. $R_1$ seedlings were genotyped to determine if they are homozygous (m/m) or heterozygote for a mutated allele or homozygous for the WT (+/+) version of the AGL6 allele, and that based both on AclI-digest-resistance of the PCR product flanking the target site and sequencing of the PCR product flanking the expected target of Cas9 (see Materials and Methods). Presence of the transgene Cas9 was PCR determined in each of the $R_1$ plants (Primers detailed in Materials and Methods and SEQ ID NOs. 19-20). Several of the $R_1$ progenies of plants sg4 and sg5 were found to carry new mutated alleles, different from the one specified in Table 4, or being mutated for bi-allelic mutated versions of AGL6. This is not surprising since they were all found to still contain the CRISPR/Cas9 cassette. Plants genotyped as hetero or homozygous for mutated AGL6 were grown in a greenhouse, side by side with the parental line MP-1. Red fruits were picked, weighed, and photographed before and after cutting them transversely at their equator, and presence or absence of seeds was recorded. As summarized in Table 5, heterozygote progenies did bear seeded fruits only, whereas the progenies homozygous or bi-allelic for mutated versions of SlAGL6 did set parthenocarpic fruits, and in many cases also under-seeded fruits, bearing up to 10 seeds, and fruits containing more than 10 seeds, which were defined as seeded fruits. The facultative nature of the mutation is thus manifested by the capacity of the parthenocarpic plants to produced also seeded and under-seeded fruits, as shown (FIG. 12) for each of the three CRISPR derived mutated lines. Thus similar to the 2012 mutant, they are manifesting a facultative parthenocarpic phenotype. Representative parthenocarpic and seeded fruits developed on plants homozygous or heterozygote for the Cas9 derived mutations are presented in FIGS. 3A-F.

To examine whether the tiny seed-like structures seen on the placenta of the red parthenocarpic fruits are indeed enlarged ovules rather than early aborted embryos, flowers were emasculated at preanthesis and the fruits developed from them were analyzed when ripen. As shown in Table 6, emasculated flowers of $R_1$ heterozygotes (+/m) progenies or MP-1 (+/+) plants set no fruits, whereas about 50% of the emasculated homozygous (m/m) flowers set fruits. And as demonstrated in FIGS. 4A,B, aborted ovules collected from fruits developed from emasculated flowers, are similar in size and appearance to those collected from non-emasculated parthenocarpic fruits picked from the same plants at the same date. This observation indicates that mutated SlAGL6 leads to true "vegetative parthenocarpy" and not to a "stimulative" one (Varoquaux et al 2000). The fact that $R_1$ parthenocarpic plants continued to set fruits under the very extreme heat stress prevailing for 40 days during the summer of 2015, whereas the indeterminate MP-1 plants grown side by side stopped yielding under these conditions (data not shown) is compatible with the vegetative nature of the parthenocarpy induced by the mutated AGL6.

Most importantly, compared to the parental line MP-1, besides being parthenocarpic, sg1 progenies devoid of the Cas9 cassette manifest no detectable phenotypic changes in their growth habit, leaf shape, leaves number to first inflorescence or pollen viability (FIGS. 7A-C and 7E-F). And the appearance of the pericarp and the shape of its cells do not show noticeable difference from that of seeded WT fruits of similar size and weight (FIGS. 7G-J vs. 7K-N). The only subtle difference noticed in the flowers is that the petals are paler and somewhat narrower and longer than in the WT (FIG. 7D). Subtle effect on petals color and their indentation are actually noticeable in *petunia* bearing Phagl6 mutation (Rijpkema et al 2009).

Example 6

Estimations of the Impact of Mutated SlAGL6 on Yield Parameters, Suggest No Adverse Effects As a first step towards assessing possible penalty of the AGL6 mutation on yielding parameters, its effect on fruit weight was examined in three different populations: The segregating determinate 2012 BC2F2 population, in the background of line M82, the segregating $F_2$ population between the big fruit semi determinate cultivar Marmande and parthenocarpic 2012, and in the $R_1$ progenies of the CRISPR/Cas9 line sg1 in the indeterminate MP-1 line background. In the 2012 $BC_2F_2$ population, effect on total yield was also estimated.

Figure 8A:
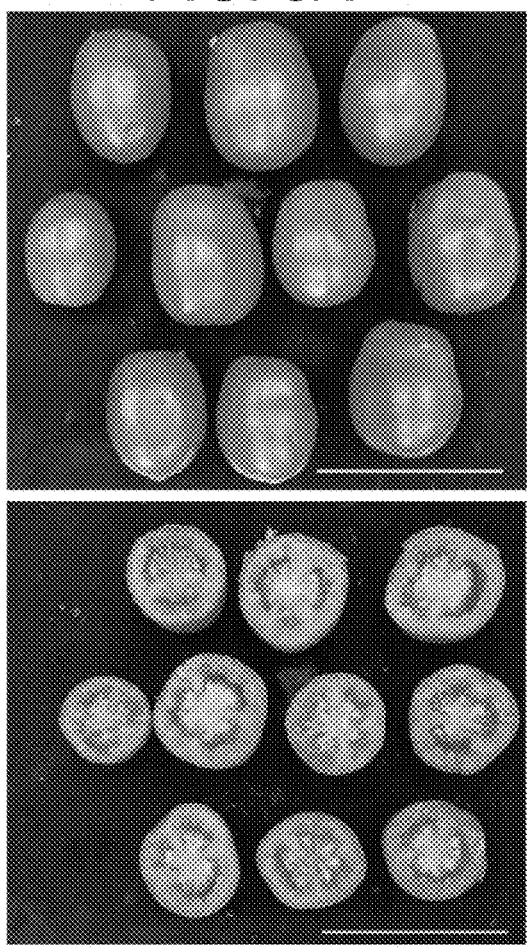
Figure 8B:
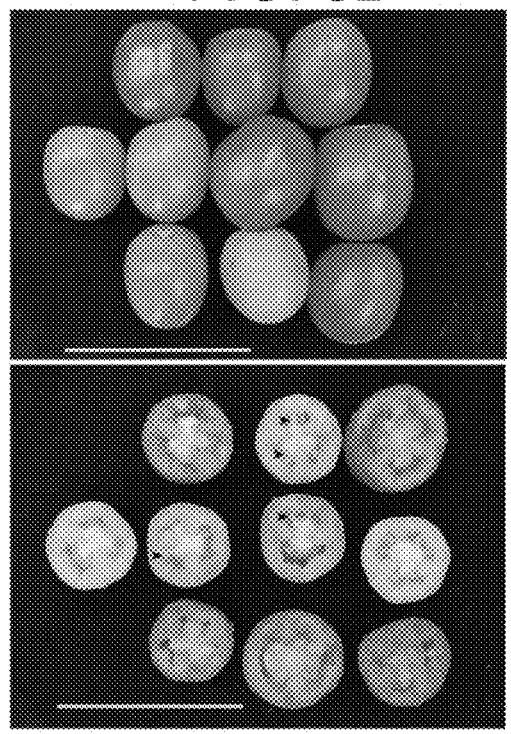
Figure 8D:
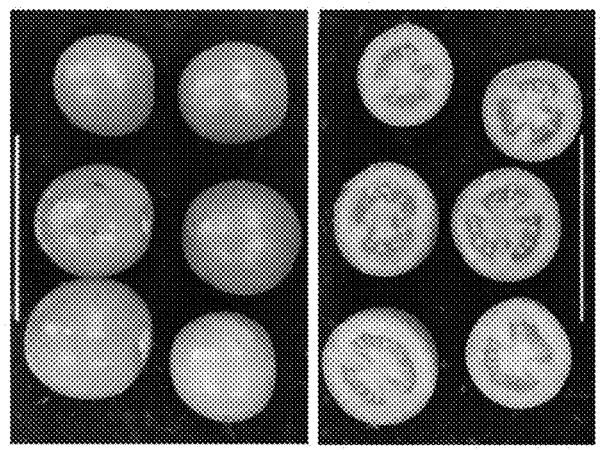
Figure 8C:
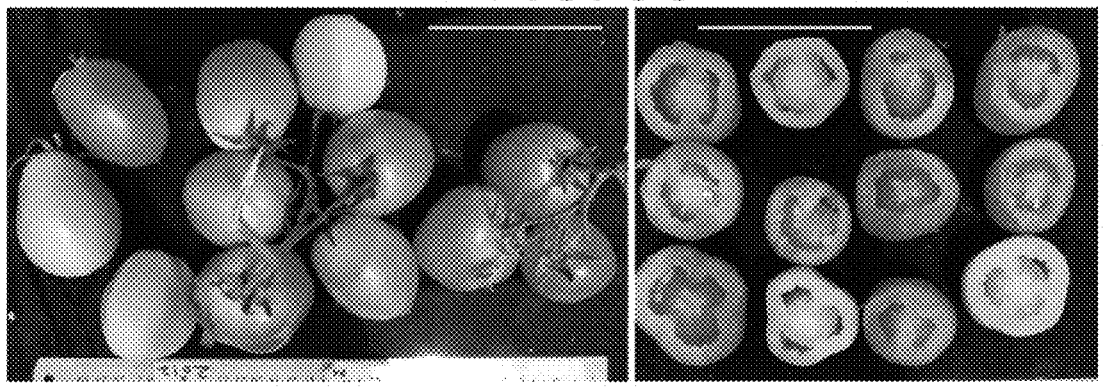

The 2012 mutation concentrates the yield, increases fruit weight, without reducing yielding potential in the 2012 $BC_2F_2$ population: The effect of the mutation on fruit weight and yielding potential was assessed on the same 2012 $BC_2F_2$ population used to map the mutation (Table 3 below). This population grew under near optimal temperatures for fertilization dependent fruit setting. At the beginning of June 2014 namely three and a half months after planting in the net-house, all the red, breaker, and mature green fruits were harvested from 10-13 plants carrying the following three alternative genotypes of SlAGL6: homozygous WT (+/+) allele, heterozygote (+/m), or homozygous mutated (m/m) allele, as well as from eight M82 plants, as detailed in Materials and Methods. As shown in FIG. 5A, the yielding potential, expressed as the yield including mature green, breaker and red fruits, harvested from the plants homozygous for the mutated allele does not differ from that of line M82, or the siblings either WT homozygous (+/+) or heterozygote (+/m) for SlAGL6 allele. Further, the plants homozygous for the mutated allele were characterized by a profoundly earlier and more concentrated yielding, manifested in a significantly higher yield of red fruits at the date of harvest (FIG. 5B). The difference in yield concentration is clearly visualized in FIGS. 6A-F. And as expected for plants with concentrated yielding, the canopy of plants bearing many red fruits at the harvest date, was profoundly smaller than that of M82 or non parthenocarpic siblings bearing less red fruits. Namely more of the plant's resources are invested in the reproductive development of the marketable crop rather than being invested in vegetative development. The average weight of the red fruits developed on the (m/m) plants is significantly higher than that of the seeded red fruits harvested from the parental line M82, or its (+/+) and (+/m) siblings (FIG. 5C). As demonstrated in FIGS. 8A-D the seedless fruits developed on the various parthenocarpic BC$_2$F2 plants were usually with complete or nearly complete jelly fill, and in many of them, on the same truss a large number of fruits of similar size reached the red ripe stage synchronously (FIG. 8C).

Expression of the 2012 mutation in F2 population derived from a cross with a large fruit cultivar does not reduce the average fruit weight: In many cases parthenocarpy was claimed to reduce fruit size compared to that of seeded fruits. In order to start estimating the potential of the 2012 mutation to support development of parthenocarpic fruits also when introduced into large fruit background, 2012 plant was crossed with the medium-large, multi-locules fruit, semi-determinate open variety Marmande (www(dot)rareseeds(dot)com/marmande-tomato/), as described in Materials and Methods. A small population of F2 progenies of this hybrid was grown in a net-house next to the BC2F2 population described above. The plants were genotyped for SNP No. 3. Fruits were collected weighed and examined for seed bearing only from plants genotyped homozygous for the mutated allele of SNP No. 3. Even at F2, when the average fruit weight is always similar to that of the small fruit parent (Perry 1915; Lippman and Tanksley 2001), out of the 26 plants analyzed, among the five plants with the highest average fruit weight, two showed a very strong parthenocarpic phenotype, as most if not all of their fruits were seedless (FIGS. 9A-B) and another one (#525, FIG. 9A) did bear both seeded and seedless fruits. This preliminary assessment indicates that the mutation does not decrease the average weight of the fruit, if at all, it may lead to increased weight.

The weight of seedless fruits of sg1 progenies does not differ from that of the parental line MP-1: Surprisingly, 12 out of the 13 tested R$_1$ progenies of plant sg1 were found to be devoid of the transgenic cassette, while all the tested progenies of plants sg5 and sg5 contained it. That enabled to assess in sg1 progenies the effect of the AGL6 mutation per se, on fruit weight. As shown in FIG. 10, in six out of the eight progenies homozygous for mutated AGL6, the weight of the seedless fruits did not differ significantly from that of their seeded heterozygote siblings and more importantly from that of the seeded fruits of the parental line MP-1. Lower average weight in two of them most likely reflects the fact that they frequently did bear more fruits per truss than the parental line, and those are usually smaller than the first fruit on the truss.

Manifestation of the facultative nature of the AGL6 induced parthenocarpy In general, most of the fruits developed on the homozygous mutated (m/m) plants of the 2012 BC$_2$F$_2$ population were seedless, even when developed under ambient conditions. However the mutation is not for obligatory parthenocarpy, which would be a serious drawback for a crop like tomato which is propagated from seeds. The exact conditions favoring seed setting in the mutated plants under fertilization permissive conditions remain to be elucidated. Vigorous inflorescences vibration resulted in many seeded fruits from plants that otherwise set mainly seedless ones (data not shown). In the absence of intentional vibration, enhanced tendency was clearly associated with two parameters. First, the small fruits developed on old plants under ambient conditions, frequently did bear seeds. This is an exceptional phenomenon, as it is broadly accepted that seeded fruits are larger than under-seeded or parthenocarpic ones developed on the same plants (e.g. Imanshi and Hiura 1975, Varga and Bruinsma. 1976, Carmi et al 2003).). Second, fruits that set at temperature mildly lower than optimal were frequently found to contain seeds. In both cases seeds production presumably reflect conditions slowing the rate of ovary expansion into fruit, thus allowing the pollen grains to complete germination, elongation and fertilization of ovules before the style is detached from the otherwise rapidly expanding ovule/fruit. Many seeded fruits developed also on (m/m) F$_2$ progenies of the 2012×Marmande hybrid (FIGS. 9A-B). Similarly, under ambient conditions, the de novo mutated AGL6 in the MP-1 background also enabled both seedless and seeded fruit development (Table 5, FIG. 12).

Example 7

Slagl6 Improves Yielding Under Heat Stress

Yielding under natural heat stress conditions was examined by comparing MP-1 and sg1 line homozygous for Slagl6 and devoid of the Cas9 cassette (at R$_2$). Plants were planted in a net-house on 20 Apr. 2016 and the first harvest was performed 67 days later. During the months of May and June the day temperatures were very high including a three days long spell (between 14 and 16 of May 2016) of extremely high temperatures (Maximum day temperature 38° C. and above, FIG. 13H). These naturally occurring heat stress conditions fall under the definition of "chronic mild heat stress" known to hamper microsporogenesis and hence fertilization dependent fruit set (see Mesihovic et al., 2016, and references therein). As demonstrated in FIG. 13A, under these climatic conditions, the red fruit yield of the parental line MP-1 was significantly lower than that of line sg1 (ca. 85% lower). This difference reflects mainly a dramatic difference in the number of fruits produced (FIG. 13,B,F,G) which was 83% lower in line MP-1, and also a significant lower fruit weight in the latter (FIG. 13C), though by 13% only. Similar to other parthenocarpic mutants (e.g. Carmi et al., 2003; Casas Diaz et al., 1987), the Total Soluble Solids (TSS) content, expressed as Brix, of red ripe seedless fruits was significantly higher than that of seeded fruits of MP-1 (FIG. 13D), while the acidity (pH) of the fruits remained similar (FIG. 13E).

TABLE 1

Description of the SNPs in chromosome 1, residing between nucleotide 85115654 and 88965277 (SL2.50 version), the predicted location of the 2012 mutation. Given are the numbers of reads of the WT nucleotides and the number of mutated nucleotide in each of the nine SNPs in this region, in each of the two sequenced libraries. The presented information is based on bioinformatics analysis of reads derived from two lanes per library. SNPs II and VII represent transversion rather than the canonical EMS induced transition mutations.

| SNP | DYN probe No. of the SNP | Position on Ch 1 (M82) SL2.50 | No. WT nt reads/No. mutated nt reads NP library | No. WT nt reads/No. mutated nt reads 2012 library | Mutation position according to IGV | Annotation |
|---|---|---|---|---|---|---|
| I | 1 | 85115654 | 52G/28A | 0G/60A | Solyc01g091480 (first intron) | Armadillo repeat kinesin 2 |
| II | 2 | 85400236 | 59A/29C | 0A/67C | Solyc01g091860 ($10^{th}$ intron) | SET domain protein, possibly involved in peptidyl-lysine monomethylation |
| III | 3 | 85536662 | 32G/25A | 0G/53A | Solyc01g093960 (ORF stop) | AGL6, Agamous-like MADS-box 6 |
| IV |  | 85785954 | 32G/25A | 0G/53A | Solyc01g094230 (silent) | Protein phosphatase-2C |
| V | 4 | 86070972 | 55T/16C | 0T/71C | Intergenic |  |
| VI |  | 86587877 | 25G/6A | 0G/55A | Solyc01g095250 (mis sense) | Chitinase, Glycoside hydrolase X2 |
| VII |  | 87367821 | 22T/13A | 0T/45A | Intergenic |  |
| VIII | 5 | 88007968 | 61C/24T | 0C/99T | Solyc01g097030 (first intron) | MUSTANG transposase Zn-fingers |
| IX | 6 | 88965277 | 49A/26G | 0A/65G | Intergenic |  |
| Total Distance |  | 3,849,623 |  |  |  |  |

TABLE 2

Analysis of a 2012 mutation test-cross population for co-segregation of the parthenocarpic phenotype and each of the six SNPs specified in Table 1 (column 2). The population was grown and characterized on the late summer 2013 (for details see results section). m/m homozygote for mutated SNP, +/+ homozygote for the WT version of the SNP, +/m heterozygote for the SNP. Although 96 plants were phenotyped and tested for all the six SNPs, in a few cases the genotyping did not produce a conclusive result, thus less than 96 results are presented for some of the SNPs.

| SNP Site # | Distance between consecutive SNPs (#nt) | Phenotype | m/m | +/m | +/+ |
|---|---|---|---|---|---|
| 1 | 0 | Parthenocarpic | 0 | 0 | 50 |
|  |  | Non-parthenocarpic. | 0 | 0 | 46 |
| 2 | 284582 | Parthenocarpic | 44 | 4 | 0 |
|  |  | Non-parthenocarpic | 1 | 44 | 0 |
| 3 | 136426 | Parthenocarpic. | 47 | 3 | 0 |
|  |  | Non-parthenocarpic | 1 | 45 | 0 |
| 4 | 534310 | Parthenocarpic | 46 | 3 | 0 |
|  |  | Non-parthenocarpic. | 3 | 42 | 0 |
| 5 | 1936996 | Parthenocarpic | 44 | 5 | 0 |
|  |  | Non-parthenocarpic | 5 | 41 | 0 |
| 6 | 957309 | Parthenocarpic | 29 | 17 | 3 |
|  |  | Non-parthenocarpic | 3 | 24 | 18 |
| Total Distance | 3,849,623 |  |  |  |  |

TABLE 3

Analysis of co-segregation of the parthenocarpic phenotype and the three different genotypes of SNPs No. 2 and 3, in the segregating $BC_2F_2$ population for the 2012 mutation. Out of the 498 plants tested, the 126 plants homozygote for mutated version of SNP No. 3 were also analyzed for their genotype of SNP No. 4. It should be noted that the 3 non-parthenocarpic plants homozygote for the mutated SNP No. 3 are also homozygote for mutated SNP No. 4. The population was grown and characterized on the late spring of 2014 (for details see Table 1, and results section). m/m homozygote for mutated SNP, +/+ homozygote for the WT version of the SNP, +/m heterozygote for the SNP.

| SNP Site # | Distance between consecutive SNPs (#nt) | Phenotype | m/m | +/m | +/+ |
|---|---|---|---|---|---|
| 2 | 0 | Parthenocarpic | 123 | 1 | 0 |
|  |  | Non-parthenocarpic | 6 | 254 | 114 |
| 3 | 136426 | Parthenocarpic | 123 | 1 | 0 |
|  |  | Non-parthenocarpic | 3 | 257 | 114 |
| 4 | 534310 | Parthenocarpic | 120 | 3 | 0 |
|  |  | Non-parthenocarpic | 3 | 0 | 0 |
| Total Distance | 670,736 |  |  |  |  |

TABLE 4

Description of the four AGL6 mutations studied: the EMS induced 2012 mutation and sg1, sg4, sg5, the three R0 CRISPR induced mutations further studied. In B. AA shaded grey differ from those of the WTAGL6 protein.

A. the mutations.

| Name | Sequence changes. |
|---|---|
| 2012: | C268/T |
| sg5 (R$_0$): | Single nt (T213) deletion |
| sg4$^a$ (R$_0$): | (1) Two nucleotides (G213/T213?) deletion, and (2) one nucleotide addition after T213 |
| sg1 (R$_0$): | 175 nt deletion, comprising the last 98 nt of intron 1, all of exon 2 (76 nt), and the first nt of intron 2. |

B. Hypothetical Translated products of the four AGL6 mutations tested

S1AGL6# (SEQ ID NO: 23)
MGRGRVELKRIENKINRQVIFSKRRNGLLKKAYELSVLCEAEVALIIFSS
RGKLYEFGSAGITKILERYQRCCLNPQDNCGERETQSWYQEVSKLKAKFE
......

2012 (SEQ ID NO: 24)
MGRGRVELKRIENKINRQVTFSKRRNGLLKKAYELSVLCEAEVALIIFSS
RGKLYEFGSAGITKTLERYQRCCLNPQDNCGERETQSWY* sg4$^a$ (SEQ ID NO: 25)
MGRGRVELKRIENKINRQVTFSKRRNGLLKKAYELSVLCEAEVALIIFSS
RGKLYEFGSAGITKTLERYQRLLP* sg5 (SEQ ID NO: 26)
MGRGRVELKRIENKINRQVTFSKRRNGLLKKAYELSVLCEAEVALIIFSS
RGKLYEFGSAGITKTLERYQRVALILKTIVVKEKHRAGTKRSLN* sg1a/sp## (SEQ ID NO: 27)
MGRGRVELKRIENKINRQVTFSKRRNGLLKKAYELSVLCEAEVALIIFSS
RGKLYEFGSAELVPRGL* sg1b/usp& (SEQ ID NO: 28)
MGRGRVELKRIENKINRQVTFSKRRNGLLKKAYELSVLCEAEVALIIFSS
RGKLYEFGSAGYIHTYIYYLFFLYIYMKNVSSLLCMGS*

For simplicity of alignments presentation, only the first 100 AA of the WT AGL6 protein are presented, underlined is the MADS box domain (see FIG. 5A).
Predicated product of sg1 if spliced from the 5' intact end of intron 1 to the intact 3' end of exon 2.
&Predicated product of sg1 if the defective intron 1 is not spliced.
*Premature stop codon

TABLE 5

Analysis of parthenocarpic fruit bearing in R$_1$ progenies derived from three different R$_0$ CRISPR/cas9 induced mutated AGL6 plants in the background of tomato line MP-1. Notice that all the tested progenies of sg4 were found to be either bi-allelic mutants or homozygote for a mutated version of AGL6. Only fruits weighing over 8 g were included in the presented analysis. (+) the WT allele, (m) - all versions of CRISPR/cas9 mutated AGL6 alleles. Fruits were classified into three categories: (P), Parthenocarpic if bearing no seeds at all; (F), Bearing a few seeds only, (≤10 seeds), (S) seeded- if bearing more than 10 seeds.

| Name Ro Plant | Plant No. (SlAGL6 genotype) | Parthenocarpic (P) (0-seeds) | Few seeds (F) (<10 seeds) | Seeded (S) (>10 seeds) | Total fruit No. | % P | % P&F | % S |
|---|---|---|---|---|---|---|---|---|
| sg5 | 5-36 (m/m) | 27 | 0 | 2 | 29 | 93.1 | 93.1 | 6.9 |
| | 5-51 (m/m) | 6 | 1 | 7 | 14 | 42.9 | 50.0 | 50.0 |
| | 5-9 (m/m) | 37 | 3 | 2 | 42 | 88.1 | 95.2 | 4.8 |
| | 5-25 (m/m) | 9 | 1 | 6 | 16 | 56.3 | 62.5 | 37.5 |
| | 5-74 (m/m) | 8 | 3 | 8 | 19 | 42.1 | 57.9 | 42.1 |
| | 5-35 (m/m) | 19 | 2 | 4 | 25 | 76.0 | 84.0 | 16.0 |
| | 5-75 (m/m) | 3 | 2 | 3 | 8 | 37.5 | 62.5 | 37.5 |
| | 5-78 (m/m) | 7 | 0 | 4 | 11 | 63.6 | 63.6 | 36.4 |
| | 5-82 (m/m) | 22 | 0 | 1 | 23 | 95.7 | 95.7 | 4.3 |
| | 5-43 (m/m) | 19 | 0 | 2 | 21 | 90.5 | 90.5 | 9.5 |
| | 5-20 (m/m) | 14 | 0 | 2 | 16 | 87.5 | 87.5 | 12.5 |
| | 5-21 (m/m) | 19 | 3 | 2 | 24 | 79.2 | 91.7 | 8.3 |
| | 5-80 (m/m) | 31 | 3 | 1 | 35 | 88.6 | 97.1 | 2.9 |
| | 5-89 (m/m) | 15 | 1 | 4 | 20 | 75.0 | 80.0 | 20.0 |
| | 5-101 (m/m) | 20 | 1 | 6 | 27 | 74.1 | 77.8 | 22.2 |
| | 5-76 (m/m) | 8 | 0 | 0 | 8 | 100.0 | 100.0 | 0.0 |
| | 5-79 (m/m) | 10 | 0 | 0 | 10 | 100.0 | 100.0 | 0.0 |
| | 5-11 (m/m) | 16 | 1 | 0 | 17 | 94.1 | 100.0 | 0.0 |
| | No. Plants (m/m) with ≥50% parth. | | | | | 15/18 (83.3%) | 17/18 (94.45) | |
| | 5-6 (+/m) | 0 | 0 | 19 | 19 | 0.0 | 0.0 | 100.0 |
| | 5-17 (+/m) | 0 | 0 | 14 | 14 | 0.0 | 0.0 | 100.0 |
| | 5-39 (+/m) | 0 | 0 | 19 | 19 | 0.0 | 0.0 | 100.0 |
| sg4 | 4-2 P (m/m) | 51 | 5 | 7 | 63.0 | 81.0 | 88.9 | 11.1 |
| | 4-11 P (m/m) | 40 | 0 | 0 | 40.0 | 100.0 | 100.0 | 0.0 |

TABLE 5-continued

Analysis of parthenocarpic fruit bearing in $R_1$ progenies derived from three different $R_0$ CRISPR/cas9 induced mutated AGL6 plants in the background of tomato line MP-1. Notice that all the tested progenies of sg4 were found to be either bi-allelic mutants or homozygote for a mutated version of AGL6. Only fruits weighing over 8 g were included in the presented analysis. (+) the WT allele, (m) - all versions of CRISPR/cas9 mutated AGL6 alleles. Fruits were classified into three categories: (P), Parthenocarpic if bearing no seeds at all; (F), Bearing a few seeds only, (≤10 seeds), (S) seeded- if bearing more than 10 seeds.

| Name Ro Plant | Plant No. (SlAGL6 genotype) | No. of Fruits in each seed content category | | | Total fruit No. | % P | % P&F | % S |
|---|---|---|---|---|---|---|---|---|
| | | Parthenocarpic (P) (0-seeds) | Few seeds (F) (<10 seeds) | Seeded (S) (>10 seeds) | | | | |
| | 4-22 P (m/m) | 43 | 3 | 1 | 47.0 | 91.5 | 97.9 | 2.1 |
| | 4-26 P (m/m) | 14 | 2 | 2 | 18.0 | 77.8 | 88.9 | 11.1 |
| | 4-27 P (m/m) | 12 | 3 | 0 | 15.0 | 80.0 | 100.0 | 0.0 |
| | 4-3 P (m/m) | 18 | 1 | 0 | 19.0 | 94.7 | 100.0 | 0.0 |
| | 4-18 P (m/m) | 12 | 1 | 11 | 24.0 | 50.0 | 54.2 | 45.8 |
| | 4-62 P (m/m) | 17 | 0 | 0 | 17.0 | 100.0 | 100.0 | 0.0 |
| | 4-31 P (m/m) | 16 | 0 | 0 | 16.0 | 100.0 | 100.0 | 0.0 |
| | 4-99 P (m/m) | 15 | 0 | 0 | 15.0 | 100.0 | 100.0 | 0.0 |
| | No. Plants (m/m) with ≥50% parth | | | | 10/10 (100%) | | | |
| sg1 | 1-8 (m/m) | 35 | 5 | 17 | 57 | 61.4 | 70.2 | 29.8 |
| | 1-13 (m/m) | 47 | 3 | 11 | 61 | 77.0 | 82.0 | 18.0 |
| | 1-21 (m/m) | 32 | 3 | 11 | 46 | 69.6 | 76.1 | 23.9 |
| | 1-23 (m/m) | 13 | 1 | 1 | 15 | 86.7 | 93.3 | 6.7 |
| | 1-26 (m/m) | 10 | 1 | 0 | 11 | 90.9 | 100.0 | 0.0 |
| | 1-3 (m/m) | 14 | 0 | 3 | 17 | 82.4 | 82.4 | 17.6 |
| | 1-11 (m/m) | 14 | 1 | 6 | 21 | 66.7 | 71.4 | 28.6 |
| | 1-27 (m/m) | 16 | 1 | 2 | 19 | 84.2 | 89.5 | 10.5 |
| | No. Plants (m/m) with ≥50% parth | | | | 8/8 (100%) | | | |
| | 1-9 (+/m) | 0 | 0 | 35 | 35 | 0.0 | 0.0 | 100.0 |
| | 1-20 (+/m) | 0 | 0 | 30 | 30 | 0.0 | 0.0 | 100.0 |
| | 1-15 (+/m) | 0 | 0 | 11 | 11 | 0.0 | 0.0 | 100.0 |
| | 1-18 (+/m) | 0 | 0 | 30 | 30 | 0.0 | 0.0 | 100.0 |
| | 1-10 (+/m) | 0 | 0 | 10 | 10 | 0.0 | 0.0 | 100.0 |
| WT | MP-7 (+/+) | 0 | 0 | 26 | 26 | 0.0 | 0.0 | 100.0 |
| | MP-10 (+/+) | 0 | 0 | 31 | 31 | 0.0 | 0.0 | 100.0 |
| | MP-12 (+/+) | 0 | 0 | 11 | 11 | 0.0 | 0.0 | 100.0 |
| | MP-13 (+/+) | 0 | 0 | 12 | 12 | 0.0 | 0.0 | 100.0 |
| | MP-14 (+/+) | 0 | 0 | 13 | 13 | 0.0 | 0.0 | 100.0 |

TABLE 6

Fruit set from emasculated flowers of CRISPR/cas9 mutated plants. Between 31 Aug. 2015-8 Sep. 2015, flowers were emasculated at preanthesis and tagged. Tags of aborted flowers were collected and recorded. Red ripe fruits developed from emasculated flowers were picked and analyzed on the 24 and 30 Sep. 2015.

| Line | SlAGL6 genotype* | No. aborted# | No. set Fruit** | No. Plants### |
|---|---|---|---|---|
| MP-1 | +/+ | 10 + 4& | 0 | 4 |
| sg 1-R1 | +/m | 5 | 0 | 2 |
| sg 5-R1 | +/m | 20 | 0 | 3 |
| | m/m | 2 | 10 | 3 |
| sg 4-R1 | m/m | 6 | 4 | 2 |

*m allele stands for all the various cas9 mutated versions of SlAGL6.
**No. of emasculated flowers that set fruit.
No. of plants per genotype from which the data was collected.
No. of emasculated flowers that aborted.
&In the parental MP-1, besides the 10 emasculated flowers, 4 flowers were tagged at pre-anthesis without emasculation, those were also aborted due to the heat stress.

Example 8

Generation of Facultative Parthenocarpic Eggplant and Pepper

The CaAGL6 (pepper) or the SmAGL6 (eggplant) are mutated by chemical mutagenesis of seeds, similar to that done as described in tomato (in Example 1 hereinabove), and $M_1$ mutagenized families arising from selfed plant grown from the mutagen treated seeds are screened for mutation in the target gene following e.g. TILLING technology (Till et al 2003). Families identified as carrying a mutation in the target gene are propagated under fertilization restrictive conditions, either heat stress, or by flower emasculation and tested for parthenocarpic fruit set. Alternatively, deletions are generated in the target gene by gene editing exploiting for example CRISPR/Cas9 technology, as was done for tomato, via stable transformation.

The following are exemplary sequences that can be used as target for CRISPR based gene editing:
Pepper
>Capana01g00134 gene target between nucleotides Chr01-44480416-44480435

GTATCACCAAAACCCTTGAG. (SEQ ID NO: 17)

Capana01g00134 cDNA is targeted between nucleotides 182-201, cleavage is predicted to occur between nucleotides 198-199.
Eggplant
>Sme2.5_06058.1 target between nucleotides 29543-29562 (minus strand)

GAGGATTAAGGCAACAACGT. (SEQ ID NO: 18)

SME2.5 06058.1 cDNA is targeted between nucleotides 204-229, cleavage is predicted to occur between nucleotides 212-213

Regenerated plants are analyzed for chimeric sections carrying a deletion in the target site as was done for tomato and progenies are similarly screened for carrying the mutation. Progenies homozygous for mutated AGL6 allele are analyzed phenotypically for parthenocarpy.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

In addition, citation or identification of any reference in this application shall not be construed as an admission that such reference is available as prior art to the present invention. To the extent that section headings are used, they should not be construed as necessarily limiting.

REFERENCES 1. 100 Tomato Genome Sequencing Consortium, Aflitos S, Schijlen E, de Jong H, de Ridder D, Smit S, Finkers R, Wang J, Zhang G, Li N, Mao L, Bakker F, Dirks R, Breit T, Gravendeel B, Huits H, Struss D, Swanson-Wagner R, van Leeuwen H, van Ham R C, Fito L, Guignier L, Sevilla M, Ellul P, Ganko E, Kapur A, Reclus E, de Geus B, van de Geest H, Te Lintel Hekkert B, van Haarst J, Smits L, Koops A, Sanchez-Perez G, van Heusden A W, Visser R, Quan Z, Min J, Liao L, Wang X, Wang G, Yue Z, Yang X, Xu N, Schranz E, Smets E, Vos R, Rauwerda J, Ursem R, Schuit C, Kerns M, van den Berg J, Vriezen W, Janssen A, Datema E, Jahrman T, Moquet F, Bonnet J, Peters S. (2014) Exploring genetic variation in the tomato (*Solanum* section *Lycopersicon*) clade by whole-genome sequencing. Plant J 80(1):136-48.
2. Adelberg J W; Xhang X P, Rhodes B B. (1997) Micropropagation of *Citrullus lanatus* (Thunb.) Matsum. and Nakai (watermelon). In: Bajaj, Y. P. S., ed. Biotechnology in agriculture and forestry, Vol. 39: High-tech micropropagation. Berlin: Springer-Verlag; pp.:60-76.
3. Ariizumi T, Shinozaki Y, Ezura H. (2013) Genes that influence yield in tomato. Breed Sci. 63(1):3-13.
4. Barg R, Pilowsky M, Shabtai S, Carmi N, Szechtman A D, Dedicova B, Salts Y. (1997) The TYLCV-tolerant tomato line MP-1 is characterized by superior transformation competence J. Exp. Bot 48: 1919-1923.
5. Beraldi D, Picarella M E, Soressi G P, Mazzucato A. Fine mapping of the parthenocarpic fruit (pat) mutation in tomato. Theor Appl Genet. 2004.
6. Bohner J, Bangerth F (1988) Cell number, cell size and hormone levels in semi-isogenic mutants of *Lycopersicon pimpinellifolium* differing in fruit size. Physiologia Plant. 72: 316-320.
7. Bolger A, Scossa F, Bolger M E, Lanz C, Maumus F, Tohge T, Quesneville H, Alseekh S, Sørensen I, Lichtenstein G, Fich E A, Conte M, Keller H, Schneeberger K, Schwacke R, Ofner I, Vrebalov J, Xu Y, Osorio S, Aflitos S A, Schijlen E, Jiménez-Goméz J M, Ryngajllo M, Kimura S, Kumar R, Koenig D, Headland L R, Maloof J N, Sinha N, van Ham R C, Lankhorst R K, Mao L, Vogel A, Arsova B, Panstruga R, Fei Z, Rose J K, Zamir D, Carrari F, Giovannoni J J, Weigel D, Usadel B, Fernie A R. (2014) The genome of the stress-tolerant wild tomato species *Solanum* pennellii. Nat Genet. 46(9):1034-1038.
8. Bolger A M, Lohse M, Usadel B. (2014) Trimmomatic: a flexible trimmer for Illumina sequence data. Bioinformatics. 30(15):2114-2120.
9. Carmi N, Salts Y, Dedicova B, Shabtai S, Barg R (2003) Induction of parthenocarpy in tomato via specific expression of the rolB gene in the ovary. Planta 217: 726-735.
10. Casas Diaz A V, Hewitt J D, Lapushner D (1987) Effects of parthenocarpy on fruit quality in tomato.—J Am Soc Hort Sci 112:634-637.
11. El Ahmadi A B, Stevens M A (1979)—Reproductive responses of heat-tolerant tomatoes to high temperatures. J. Amer. Soc. Hort. Sci. 104:686-691.
12. Falavigna A, Badino M, Soressi G P.—(1978) Potential of the monomendelian factor pat in the tomato breeding for industry. Genetica Agraria, 32: 159-160 (Abstr.).
13. Ficcadenti N, Sestili S, Pandolfini T, Cirillo C, Rotino G L, Spena A (1999) Genetic engineering of parthenocarpic fruit development in tomato, Mol. Breed. 5:463-470.
14. Galpaz N, Burger Y, Lavee T, Tzuri G, Sherman A, Melamed T, Eshed R, Meir A, Portnoy V, Bar E, Shimoni-Shor E, Feder A, Saar Y, Saar U, Baumkoler F, Lewinsohn E, Schaffer A A, Katzir N, Tadmor Y. (2013) Genetic and chemical characterization of an EMS induced mutation in *Cucumis melo* CRTISO gene. Arch Biochem Biophys. 539(2):117-125.
15. Ghio C, Ramos M L, Altieri E, Bulos M, Sala C A. (2013) Molecular characterization of Als1, an acetohydroxyacid synthase mutation conferring resistance to sulfonylurea herbicides in soybean. Theor Appl Genet. 126(12):2957-2968.
16. Gillaspy G, Ben-David H, Gruissem W (1993) Fruits: a developmental perspective. Plant Cell 5: 1439-1451.
17. Gorguet B, Eggink P M, Ocana J, Tiwari A, Schipper D, Finkers R, Visser R G F, van Heusden A W (2008) Mapping and characterization of novel parthenocarpy QTLs in tomato. Theor Appl Genet 116:755-767.
18. Gorguet B, van Heusden A W, Lindhout P. (2005) Parthenocarpic fruit development in tomato. Plant Biol (Stuttg). 7:131-139.

19. Hazra P, Dutta A K. (2010). Inheritance of parthenocarpy in tomato (*Solanum lycopersicum*) and its association with two marker characters. Int J Plant Sci, 1: 144-149.
20. Imanshi S, Hiura I (1975) Relationship between fruit weight and seed content in the tomato. J Jpn Soc Hort Sci 44:33-40.
21. Joubes J, Chevalier C. (2000) Endoreduplication in higher plants. Plant Mol Biol. 43:735-745. Review.
22. Koo, S. C., Bracko, O., Park, M. S., Schwab, R., Chun, H. J., Park, K. M., Seo, J. S., Grbic, V., Balasubramanian, S., Schmid, M., Godard, F., Yun, D. J., Lee, S. Y., Cho, M. J., Weigel, D. and Kim, M. C. (2010) Control of lateral organ development and flowering time by the *Arabidopsis thaliana* MADS-box Gene AGAMOUS-LIKE6. Plant J. 62, 807-816.
23. Li H, Durbin R. (2009) Fast and accurate short read alignment with Burrows-Wheeler transform. Bioinformatics. 25(14):1754-1760.
24. Li H, Handsaker B, Wysoker A, Fennell T, Ruan J, Homer N, Marth G, Abecasis G, Durbin R; 1000 Genome Project Data Processing Subgroup. (2009) The Sequence Alignment/Map format and SAMtools. Bioinformatics. 25(16):2078-2079.
25. Li J F, Norville J E, Aach J, McCormack M, Zhang D, Bush J, Church G M, Sheen J. (2013). Multiplex and homologous recombination-mediated genome editing in *Arabidopsis* and *Nicotiana benthamiana* using guide RNA and Cas9. Nat. Biotechnol. 31:688-691.
26. Lieber M R. (2010) The mechanism of double-strand DNA break repair by the nonhomologous DNA end-joining pathway. Annu Rev Biochem. 79:181-211.
27. Lin S, George W L, Splittstoesser W E (1984) Expression and inheritance of parthenocarpy in 'Severianin' tomato. J Hered 75 (1): 62-66.
28. Lippman Z, Tanksley S D. (2001) Dissecting the genetic pathway to extreme fruit size in tomato using a cross between the small-fruited wild species *Lycopersicon pimpinellifolium* and *L. esculentum* var. Giant Heirloom. Genetics. 158: 413-422.
29. Mazzucato A, Taddei A R, Soressi G P (1998) The parthenocarpic fruit (pat) mutant of tomato (*Lycopersicon esculentum* Mill.) sets seedless fruits and has aberrant anther and ovule development. Development 125:107-114.
30. Michelmore R W, Paran I, Kesseli R V. (1991) Identification of markers linked to disease-resistance genes by bulked segregant analysis: a rapid method to detect markers in specific genomic regions by using segregating populations. Proc Natl Acad Sci USA. 88(21):9828-9832.
31. Nuez F, Costa J, Cuartero J (1986) Genetics of the parthenocarpy for tomato varieties "Sub-Artic Plenty," "75/59" and "Severianin.". Z Pflanzenzucht 96:200-206.
32. Pan, I. L., McQuinn, R., Giovannoni, J. J. and Irish, V. F. (2010) Functional diversification of AGAMOUS lineage genes in regulating tomato flower and fruit development. J. Exp. Bot. 61, 1795-1806.
33. Pandolfini T, Rotino G L, Camerini S, Defez R, Spena A. (2002) Optimisation of transgene action at the post-transcriptional level: high quality parthenocarpic fruits in industrial tomatoes. BMC Biotechnol. 2:1
34. Anderson P. (1995) Mutagenesis. Methods Cell Biol.; 48:31-58. Review.
35. Pattison R J, Csukasi F, Zheng Y, Fei Z, van der Knaap E, Catali C. (2015) Comprehensive tissue-specific transcriptome analysis reveals distinct regulatory programs during early tomato fruit development. Plant Physiol. 168:1684-1701.
36. Perry F E. (1915) The inheritance of size in tomatoes. The Ohio Naturalist 15: 473-497.
37. Philouze J, Maisonneuve B (1978b) Heredity of the natural ability to set parthenocarpic fruits in a German line. Tomato Genet. Coop. 28: 12.
38. Philouze J. (1989) Natural parthenocarpy in tomato. IV. A study of the polygenic control of parthenocarpy in line 75/59. Agronomie 9:63-75.
39. Picken A J F (1984) A review of pollination and fruit set in the tomato (*Lycopersicon esculentum* Mill.). J Hort Sci 59:1-13.
40. Ruan Y L, Patrick J W, Bouzayen M, Osorio S, Fernie A R. (2012) Molecular regulation of seed and fruit set. Trends Plant Sci. 17:656-665.
41. Sato S, Kamiyama M, Iwata T, Makita N, Furukawa H, Ikeda H. (2006) Moderate increase of mean daily temperature adversely affects fruit set of *Lycopersicon esculentum* by disrupting specific physiological processes in male reproductive development. Ann Bot (Lond). 97:731-738.
42. Shan Q, Wang Y, Li J, Zhang Y, Chen K, Liang Z, Zhang K, Liu J, Xi J J, Qiu J L, Gao C. (2013) Targeted genome modification of crop plants using a CRISPR-Cas system. Nat Biotechnol. 31(8):686-688.
43. Shinozaki Y, Ezura K. (2016) Tomato fruit set and its modification using molecular breeding techniques. In: Functional Genomics and Biotechnology in Solanaceae and Cucurbitaceae Crops (H. Ezura et al. eds.), Biotechnology in Agriculture and Forestry 70. Springer-Verlag Berlin Heidelberg. pp. 93-112.
44. Smaczniak C, Immink R G, Angenent G C, Kaufmann K. (2012) Developmental and evolutionary diversity of plant MADS-domain factors: insights from recent studies. Development. 139:3081-3098.
45. Tang N, Deng W, Hu G, Hu N, Li Z. (. 2015) Transcriptome profiling reveals the regulatory mechanism underlying pollination dependent and parthenocarpic fruit set mainly mediated by auxin and gibberellin. PLoS One 24; 10(4): e0125355.
46. Vardy E, Lapushner D, Genizi D, Hewitt J (1989a) Genetics of parthenocarpy in tomato under a low temperature regime: I. Line R P75/59. Euphytica 41:1-8.
47. Vardy E, Lapushner D, Genizi D, Hewitt J (1989b) Genetics of parthenocarpy in tomato under a low temperature regime: II. Cultivar "Severianin". Euphytica 41: 9-15.
48. Varga A, Bruinsma J (1986) Tomato. In: CRC Handbook of Fruit Set and Development (Ed. Monselise S P) CRC Press Inc. Boca Raton, FL pp. 461-481.
49. Varga A, Bruinsma J. (1976) Roles of seeds and auxins in tomato fruit growth. Zeitschrift fUr Pflanzenphysiologie 1976; 80:95-104.
50. Varoquaux F, Blanvillain R, Delseny M, Gallois P. (2000) Less is better: new approaches for seedless fruit production. Trends Biotechnol. 18(6):233-242. Review.
51. Waibel F. Filipowicz W. (1990) U6 snRNA genes of *Arabidopsis* are transcribed by RNA polymerase III but contain the same two upstream promoter elements as RNA polymerase 11-transcribed U-snRNA genes. Nucleic Acids Res., 18:3451-3458.
52. Wang H, Jones B, Li Z, Frasse P, Delalande C, Regad F, Chaabouni S, Latché A, Pech J C, Bouzayen M. (2005) The tomato Aux/IAA transcription factor IAA9 is involved in fruit development and leaf morphogenesis. Plant Cell. 17(10):2676-2692.
53. Wang H, Schauer N, Usadel B, Frasse P, Zouine M, Hernould M, Latché A, 54. Wang, P., Liao, H., Zhang, W., Yu, X., Zhang, R., Shan, H., Duan, X., Yao, X. and Kong, H. (2015) Flexibility in the structure of spiral flowers and its underlying mechanisms. Nat. Plants, 2, 15188.
55. Pech J C, Fernie A R, Bouzayen M. (2009) Regulatory features underlying pollination-dependent and -independent tomato fruit set revealed by transcript and primary metabolite profiling. Plant Cell. 21:1428-1452.
56. Ye J, Parra E J, Sosnoski D M, Hiester K, Underhill P A, Shriver M D. (2002) Melting curve SNP (McSNP) genotyping: a useful approach for diallelic genotyping in forensic science. J Forensic Sciences 47: 593-600.
57. Erickson A N., Markhart A H (2002) Flower developmental stage and organ sensitivity of bell pepper (Capsicum annuum L.) to elevated temperature. Plant Cell Environment 25(1): 123-130
58. Kawasaki Y (2015) Fruit set and temperature stress. In: Abiotic stress biology in horticultural plants. (Y. Kanayama, A. Kochetov, eds.), Springer Japan. Pp. 87-99.
59. Karapanos I C, Mahmood S, Thanopoulos C (2008) Fruit Set in Solanaceous Vegetable Crops as Affected by Floral and Environmental Factors. The European Journal of Plant Science and Biotechnology 2 (Special Issue 1), 88-105.
60. Till B J, Reynolds S H, Greene E A, Codomo C A, Enns L C, Johnson J E, Burtner C, Odden A R, Young K, Taylor N E, Henikoff J G, Comai L, Henikoff S. (2003) Large-scale discovery of induced point mutations with high-throughput TILLING. Genome Res. 13(3):524-530
62. Selleri, L. (2011) Ph. D. Thesis www.hdl.handle.net/2067/2501 Bassel, G. W., Mullen, R. T. and Bewley, J. D. (2008) procera is a putative DELLA mutant in tomato (Solanum lycopersicum): effects on the seed and vegetative plant. J. Exp. Bot. 59, 585-593.
63. Mazzucato, A., Cellini, F., Bouzayen, M., Zouine, M., Mila, I., Minoia, S., Petrozza, A., Maurizio, E. Picarella, M. E., Ruiu, F. and. Carriero, F. (2015) A TILLING allele of the tomato Aux/IAA9 gene offers new insights into fruit set mechanisms and perspectives for breeding seedless tomatoes. Mol. Breeding, 35, 22.
64. Saito, T., Ariizumi, T., Okabe, Y., Asamizu, E., Hiwasa-Tanase, K., Fukuda, N., Mizoguchi, T., Yamazaki, Y., Aoki, K. and Ezura, H. (2011) TOMATOMA: a novel tomato mutant database distributing Micro-Tom mutant collections. Plant Cell Physiol. 52, 283-896.
65. Carrera, E., Ruiz-Rivero, O., Peres, L/E., Atares, A. and Garcia-Martinez, J. L. (2012) Characterization of the procera tomato mutant shows novel functions of the SlDELLA protein in the control of flower morphology, cell division and expansion, and the auxin-signaling pathway during fruit-set and development. Plant Physiol. 160, 1581-1596.
66. Zhang, J., Nallamilli, B. R., Mujahid, H. and Peng, Z. (2010) OsMADS6 plays an essential role in endosperm nutrient accumulation and is subject to epigenetic regulation in rice (Oryza sativa). Plant J. 64, 604-617
67. Duan, Y., Xing, Z., Diao, Z., Xu, W., Li, S., Du, X., Wu, G., Wang, C., Lan, T., Meng, Z., Liu, H., Wang, F., Wu, W. and Xue, Y. (2012) Characterization of Osmads6-5, a null allele, reveals that OsMADS6 is a critical regulator for early flower development in rice (Oryza sativa L.). Plant Mol. Biol. 80, 429-442.

SEQUENCE LISTING

```
<160> NUMBER OF SEQ ID NOS: 28

<210> SEQ ID NO 1
<211> LENGTH: 5155
<212> TYPE: DNA
<213> ORGANISM: Lycopersicon esculentum
<220> FEATURE:
<221> NAME/KEY: misc_feature
<222> LOCATION: (1)..(5155)
<223> OTHER INFORMATION: SlAG6 gene sequence

<400> SEQUENCE: 1
gctaacccca cctcccctat tcattactga tcataacata aataatcttt ttgatagaat    60
tagctagctc taggaataga agaagaaaaa aatggggaga gggagagtgg aactaaagag   120
aatagagaac aaaatcaacc gtcaagtgac attttctaag aggaggaatg gtttgttgaa   180
gaaagcttat gaattatcag tgctttgtga ggctgaagtt gctctcatca tcttctctag   240
tcgtggaaag ctctatgagt ttggtagtgc agggtatata cacacatata tatattatct   300 tttttttta tatatataca tgaaaaatgt gtcaagttta ctttgtatgg gctcttaatt   360
attagtaata aataattttt gatgatatgg ggttcttcta aatcataaaa agattacaac   420
ttcaagttat tttttcatat ggggttcttc taaatcataa aaagattaca actttaagtt   480
attttttcat atggggttct tctaaatcat aaaaagatta ctaactttat ggttttttta   540
ttatatgggg ttcttctaaa acataaaaag attacaactt tatgttattt tttcatatgg   600
ggttcttcta aatcacaaaa aagattacaa agtttttttt ttttcgtatg gggttcttca   660
aaaatcataa aaagattata actatgtgta tattttcata cggggttcat agtaactaag   720
```

```
ttttcttata catgaaaagt ctgtcaagtt tactttgtgg gggctcttaa tagctaattc      780
tagaaaatgg ggttcttcta aatcataaaa agattacaac ttcatgtttg ttttcatatg      840
aggttcatca tataaatatg tactaagctt tttaacacat gaaaagtgtg tctagtttat      900
tactttgtga ggatctaatt agctaattct tgaaatgggg ttctttaaat cataaaaaga      960
ttacaatttt atgtttttt tatggggatc atcatatata taagaaaga taataacaca      1020
gagagagtga aagacagtga ggtcagttgt ttttgtttt tgtgggagtg gattttatgt      1080
ttttaattca acttttttt taaaataaat aaaataaatt gttggataaa tagacttgct      1140
aaattggtat gggcttttgc agcactttac acaagcacca acttatcttt atctcttgtc      1200
tgttaagtgg agttttcaga tttgtatctc tctttgagtt ctctttcttc tttcatttta      1260
atgtttgatc aaaatgtcat gaatatgaga aggggttttt ggttctacca attggatatt      1320
gacacgtttc aatggtcaat ccacaaaatc aaaagatcag agtaagaact gaccaggtct      1380
agaaacttct tcttccaact cttttggaca aatgtgaaag atctagggtt tctctccatt      1440
ttgttcctac tatttccttt catcttttc tttaatgctt tgctgtttt ttggaacact      1500
tgttagtcca atggttataa aacatcaaaa agtttcaaac tttgtctact ttataccttt      1560
tcatccatag atcttgaagt cctttcaatg atttctactt catataccaa acacatacat      1620
tttgttctgt tatgaccaaa tcctttgtgt aaaagagagt attgtactaa actgcacatc      1680
aaaaaatagt ggcatatgcc tgttaaaaag gaatttgttc atatttgaga tttcttgcat      1740
ttatcagttt tgcaggttag tatataatct gattgctact ttttatgcat atgaaaaaag      1800
gagttttctt tatcagttcc catacccaa gaactgatta agatctcttt tttctttcca      1860
ttttagtgaa atttattact gatgagtgtt atgagattct tgagttttc aatatgtatt      1920
accaactcat attaccaaca aaaaaatgag ttttcatat tcttcagttt tcttgatatc      1980
atttttttgt tattgttta ttgaagaatg atagtgttaa tgtaaaaatg ctttttttgtt      2040
attggtaact ttttaaact catacacatc aatatcttgg ggtaatagca gtgttaaaag      2100
aggactcctt ttttgctcaa tttttttgt tgtctttcca aaaaaaaaaa atggtgtcca      2160
actaataatt tcttgtgttc ataatcacat ttgttctacc atgtaacact tttgtttaga      2220
attagggttt tgtatggagc aaatgtgttg caaaatgaaa aacttgtttt aatttcttga      2280
atagtactcc atacgttcat attagttgtt cactttcatg tttacatgtt aatctataga      2340
gagcccttaa ttccactttc ccccaactaa tatgggatgt ctgaagtagt acaaaaagct      2400
attaagcct taattcaatg tctaaatagt attgttata taattatatt ctatctaatt      2460
atccttaaag aattgtcaaa atgaatttct gtttccactt atatttgcta agtcttttc      2520
cactttccaa atatgaaagg ttggaactta gaagaaggaa aaagacatcc acttgttgta      2580
ctaatggcca attaaataaa atggagcaaa tgaatagaaa tgagaagact tttgctattt      2640
taatccttgt gtaatgtact cttccagctt ttgtcttttt aatttctaat gtatgcctcc      2700
ttttttgtcca ttatataatc aatagtttgt ttgtttgatc ttgtgtttat ttttcttttt      2760
tgatttgggg tagaatggat ggtcgagcct gatgagtctt tttcatggtt atatatgtga      2820
attttatttt taaagtggtg gccgtaggat ttgaatttgg aattttctc tgctttgata      2880
tcatattaac gtgtataata atcaaaatat ttaaactatt aaacataata ggctgtagct      2940
tacatatagt gctaaaatg atagtggaaa ttaaacttgg tatgagcttg actcccatac      3000
acctattta gcagtactcg cttcattcca atttatttgt tttaactttc tttattccat      3060
ttataaaagg agtgtgtctt gtatttgttt ttttttttaa atttacttt caatatgacc      3120
```

-continued

```
ttatgatcgc aaaataaatg acactttcac acatccataa tttataatttt aaaatcacaa    3180
attttaaatt ttttttttata ttcttaaaat tcgtttcaag tcgaaatcac aaattttatg    3240
ttgatgcctt tacatgtttt atgtaatatt atatgtcttt tgagtgtttt ttaccctcaa    3300
caaggcatta tttaatagcc ttgaaatcag taagagtatt ggttaccatt aattatgttt    3360
tatctctcct taatcgtgtc acttaattag ttgaaacaat aagaataaga tttggaaaga    3420
aaagtaatat tttgaatatt atgtttgttt tgttggcagt atcactaaaa cccttgagag    3480
gtaccaacgt tgttgcctta atcctcaaga caattgtggt gaaagagaaa cacaggtttg    3540
tagcttcatc taggatttta ctaacttttta cttatcatgt tttgcataaa tttttttattt    3600
ttgttgtaaa tttagagctg gtaccaagag gtctctaaat taaaggccaa gtttgaagca    3660
cttcaacgaa ctcaaaggtt atttatgtca ttttttgctta ttcatttgac ataattatat    3720
tataattttg acacacatat atatatatat atccttgaaa ttaagtgtgt ttaagttttt    3780
tgagatgttt tttttattgg tataataata catatgaagg cacttgcttg gtgaagatct    3840
tggagcacta agtgtgaagg agttgcaaaa tcttgaaaaa caacttgaag gtgcacttgc    3900
acaagctaga caaagaaagg tatatactaa attgccatct ttttgccatt gttgttaaat    3960
atgatatatg aaaaacttta ttatatcgtg ttcacacaat tgatattagt tgcttgagcc    4020
atgaggcttc tctttgcctc atgtattcaa atctaattct tttaaggtcc actaaatttg    4080
gatttacctt ttctgtctcg taagtcgagc tgtatcataa aatattaaga atttgtttct    4140
acattttgta gacacaaata atgatggaac agatggagga gcttcgtaga aaggtaagat    4200
gtataaaatg ctgaatgact aatttcttcc tttccaaact agctattcgg aataccacct    4260
aaataattat agtcgtagag taaattaagt tgggttgaaa tagtttgagg tttattcaat    4320
gatgtatatg atacatcttg gtggttaatt atcaaggggg tatattcact ttgatacacg    4380
tgaattcata atttctttt aaaattaagt atattatata aatgttttt taaaaaaaaa    4440
ttctaaattc atttacgttg gtaattgatt tttattcatg ttatcaggag cgtcatcttg    4500
gtgatgtgaa caagcagttg aagattaagg tttctcttga actatcatcg gtactactcc    4560
ataatattgc tcgaattctt taaaaatatc agagcaagcg agtgcatatg tttgaatgtt    4620
ctttgttgta tgttgacagt ttgagggtga aggacaaggt gttcctttc catggagtaa    4680
ttgtaatgca tctttagatg aagcaggaag cagcaccttt catgtccacc attctcaatc    4740
aaatcacatg gactgtgatt tacctgatcc agttcttcaa atagggtatg cacctacatt    4800
actttcatct attaattgat cgcgctcact caacttatga taattcacat taaaaaaacg    4860
tcttttcttt tgtttttttcg aaagtcattt tacttgacct aattagcttt aacattaatg    4920
taaaactgta ggtatcatca gtatatggct gcagatggct cctcagggtc aaggaacatg    4980
gctgttgaga gtaacattat ccatggttgg ggtctttaat ttctaattct aattatggat    5040
tatactagta caagttttttt gcttttaagt ttttcagatt aaaaaactca agtgacatat    5100
aattatgatt tgaaatgcat gttatatagt aatgtataat tttagcaagt gtcat    5155
```

<210> SEQ ID NO 2
<211> LENGTH: 986
<212> TYPE: DNA
<213> ORGANISM: Lycopersicon esculentum
<220> FEATURE:
<221> NAME/KEY: misc_feature
<222> LOCATION: (1)..(986)
<223> OTHER INFORMATION: SlAG6 mRNA Sequence

<400> SEQUENCE: 2

```
gctaaccca cctcccctat tcattactga tcataacata aataatcttt ttgatagaat      60
tagctagctc taggaataga agaagaaaaa aatggggaga gggagagtgg aactaaagag     120
aatagagaac aaaatcaacc gtcaagtgac attttctaag aggaggaatg gtttgttgaa     180
gaaagcttat gaattatcag tgctttgtga ggctgaagtt gctctcatca tcttctctag     240
tcgtggaaag ctctatgagt ttggtagtgc aggtatcact aaaacccttg agaggtacca     300
acgttgttgc cttaatcctc aagacaattg tggtgaaaga gaaacacaga gctggtacca     360
agaggtctct aaattaaagg ccaagtttga agcacttcaa cgaactcaaa ggcacttgct     420
tggtgaagat cttggagcac taagtgtgaa ggagttgcaa atcttgaaa aacaacttga     480
aggtgcactt gcacaagcta gacaaagaaa gacacaaata atgatggaac agatggagga     540
gcttcgtaga aaggagcgtc atcttggtga tgtgaacaag cagttgaaga ttaaggtttc     600
tcttgaacta tcatcgtttg agggtgaagg acaaggtgtt cctttccat ggagtaattg      660
taatgcatct ttagatgaag caggaagcag cacctttcat gtccaccatt ctcaatcaaa     720
tcacatggac tgtgatttac ctgatccagt tcttcaaata gggtatcatc agtatatggc     780
tgcagatgga gcctcagggt caaggaacat ggctgttgag agtaacatta ccatggttg      840
gggtctttaa tttctaattc taattatgga ttatactagt acaagttttt tgcttttaag     900
tttttcagat taaaaaactc aagtgacata taattatgat ttgaaatgca tgttatatag     960
taatgtataa ttttagcaag tgtcat                                          986
```

<210> SEQ ID NO 3
<211> LENGTH: 252
<212> TYPE: PRT
<213> ORGANISM: Lycopersicon esculentum
<220> FEATURE:
<221> NAME/KEY: MISC_FEATURE
<222> LOCATION: (1)..(252)
<223> OTHER INFORMATION: SlAG6 amino acid sequence

<400> SEQUENCE: 3

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Glu Ala Glu Val Ala Leu Ile Ile Phe
        35                  40                  45

Ser Ser Arg Gly Lys Leu Tyr Glu Phe Gly Ser Ala Gly Ile Thr Lys
    50                  55                  60

Thr Leu Glu Arg Tyr Gln Arg Cys Cys Leu Asn Pro Gln Asp Asn Cys
65                  70                  75                  80

Gly Glu Arg Glu Thr Gln Ser Trp Tyr Gln Glu Val Ser Lys Leu Lys
                85                  90                  95

Ala Lys Phe Glu Ala Leu Gln Arg Thr Gln Arg His Leu Leu Gly Glu
            100                 105                 110

Asp Leu Gly Ala Leu Ser Val Lys Glu Leu Gln Asn Leu Glu Lys Gln
        115                 120                 125

Leu Glu Gly Ala Leu Ala Gln Ala Arg Gln Arg Lys Thr Gln Ile Met
    130                 135                 140

Met Glu Gln Met Glu Glu Leu Arg Arg Lys Glu Arg His Leu Gly Asp
145                 150                 155                 160

Val Asn Lys Gln Leu Lys Ile Lys Val Ser Leu Glu Leu Ser Ser Phe
```

```
                165                 170                 175
Glu Gly Glu Gly Gln Gly Val Pro Phe Pro Trp Ser Asn Cys Asn Ala
            180                 185                 190

Ser Leu Asp Glu Ala Gly Ser Ser Thr Phe His Val His His Ser Gln
        195                 200                 205

Ser Asn His Met Asp Cys Asp Leu Pro Asp Pro Val Leu Gln Ile Gly
    210                 215                 220

Tyr His Gln Tyr Met Ala Ala Asp Gly Ala Ser Gly Ser Arg Asn Met
225                 230                 235                 240

Ala Val Glu Ser Asn Ile Ile His Gly Trp Gly Leu
                245                 250

<210> SEQ ID NO 4
<211> LENGTH: 6341
<212> TYPE: DNA
<213> ORGANISM: Capsicum annuum
<220> FEATURE:
<221> NAME/KEY: misc_feature
<222> LOCATION: (1)..(6341)

<400> SEQUENCE: 4
```

| | | | | |
|---|---|---|---|---|
| atggggagag ggagagtgga actaaagaga atagagaaca aaatcaaccg tcaagtgacg | 60 |
| ttttctaaga ggaggaatgg tttgttgaag aaagcttatg aactttcagt gctttgtgat | 120 |
| gctgaagttg ctctcatcat cttctctggt cgcggaaaac tctatgagtt tggtaatgca | 180 |
| gggtatatat actaagcttt cttacacatg aaaaggtgtt acgtttactt tgtatgggct | 240 |
| cttaatagct gattccttgat atgggggttc ttctaaatca taaaaagatt agaactttat | 300 |
| gtttgttttc atctggggtt catcagatat atatactaag cttgttgtac atggaagtgt | 360 |
| gccaactttta tttgtgtggg ttcttaatgg ctaattcttg ataaggggtt cttctaaatc | 420 |
| ataaaagatt acaactttat gtttgttttt catatggggt tcattagata tataaagaaa | 480 |
| gatgaggtga gtgtgtgttg tttatgttgt gggagtggga ttataagtct ttaaaagcct | 540 |
| aattactctg acttgctaaa ttggtattgg cttttgcagc actttacaca agcaccaact | 600 |
| tattttatct gttgtctgtt aagtagagta gttagttgct gttttcagat ttggttcttt | 660 |
| cttgtgtttt ctttctttc ttagttgtct gtttgatcaa aatgtgctga aaggggggtt | 720 |
| tggttttacc aatgggaaat tgacacgttt caattgtttt tgagtagaga gcttaccaat | 780 |
| ccacaaatac ctaagatcag agtaaaggac tgcagtgtgt gctctctcac tcagtccaag | 840 |
| aaacttcttc caacccttttt ggacaactgt tcaagatcta gggtttctct ccattttgtt | 900 |
| cctactatat tacctttcat ctttttattt aatgcttttg gagtttcttg gagcacttat | 960 |
| tagtccaatg gttctaaaac atcagaaagt ttcaaacttt gttttcttaa ttttttcatcc | 1020 |
| tatgatcttg aggtctcttc actgatttct actataccaa actcatagtt tttcctttct | 1080 |
| gttgtcatga ctaaatcctt tgtgtaaaag agagtattgt actgcactgc acatcaaaaaa | 1140 |
| taagtggcat gcctgtgaga agggaatttg ttcatatttg atgttgca tttatcagtt | 1200 |
| ttgcaggtaa gaatatgatc tgattgctac tttctatgta agaaaaggag ttttctttat | 1260 |
| caattcacaa accccaagaa ctgatcaaga tttctatttt tcattccatt tggtgaaac | 1320 |
| ttaatattat tggtgtaaaa tgccagagct ggtttaaatg tgtgacagtt tgattcttga | 1380 |
| gctttaattt ccatatgtta gcaactttgg ttccagttca tgttctttga gtaagtgtta | 1440 |
| tgaaactgtg tacttttatt ccctcccacc caaagcctta aacttctcac tgtgcaggtc | 1500 |
| caatttttatc atcccttttgt ttatgttttat ttgcaaatgt tttgtatgta catcaatgtt | 1560 |

```
gctcggcttc ttcaaaaatg ttaaccaggc gtgtcatatt ctccaaaagt aatgtattta    1620
ttgagagtta gacatagatg caacatcgaa gtgatgaaga gttcccgcaa cctagttgta    1680
catatgttct ttttcatatt cttcaaattt tgacatcttt tgaagaatga ttttgtattt    1740
aagaaaaaat gcttctttat tttttgataa ttttatttga cttttaagtc atgcaataat    1800
ttcatcaata tcttggagta atagcacagt gttgaagagg agtcctcttt tgcataatat    1860
ttttttgtaa tctttcaaga aaattactaa acaaaaagat gtagtggcca aataccattc    1920
ttgtcttaat cacatttgta ttacaatgta gcacttttgt ttagaattag gttttgtat     1980 ggagtaaaag tgatagtatt agttattgat gacaaaaaga aaacttgatt ggcagtttta    2040
aatccttaaa ttcaatgtct aaatggttta gtttatgttt ctaattatgc ttaaggaatt    2100
gcccaaatga atttcttttt ccactttttc tttttgctaa ctcttttttcc actttccaat   2160 tatggaaggt tggaagaagg aaaaagacaa cctcatgctg tacttatggc caattaaata    2220
aaatggagca aatacataga aatgagaaga catttgctat attaatcctt gtgtactcaa    2280
tcagcttttg cctctactgt atttttattc tgctgtatgc ccccttttg cccattatat     2340 attcaatggt tttctattat ttggagtttg tttgtttgtt tttgtttgtc ttttgttttg    2400
ggtggaatgg atggttagtt gaaccttctt ttcatgggct aagcaagtac tgcctccttg    2460
acacattaat taaaaattaa ttaattaata atacgattat tttatcataa ttctattaga    2520
tgatatttac attgtgtctt gaaattaatt tagagaaaaa ataactaatg ctaagagtaa    2580
aatagaaaaa aaaaatgtta tcttatttga tatgtcaaaa atgatagaaa ttcaattagg    2640
aaattagtga tgagtaaaag tgaacaagga caataatttt ttttttaaa aaaaaaattg     2700 atgacaataa ttaagacttg aattcagact atttccttgg tctaattaat atcatttttaa   2760 atgtatgaat atgtaatcta aatttttaaa ctaaacataa caggccgtag cttaaatata    2820
tatattgcat ttaattatct aaaagatgtg ctgaatatca tagtggaaat taaacttggt    2880
atagacttta acttcccata cgcattattt agtagtactc actctatttc aattaatttg    2940
ttaaaaataa tgaatatttt ttttttttga taattcttta atttcaattt ttcatatgag    3000
atatgtcatg tttaagatta caaaattaaa gatattttga taaattatac ttttctttaa    3060
gagcataaaa ttctaaaatt tttttttttt ttttaaaaat attatgtcaa gttaaaagca    3120
gataaataaa ttgaaatgga ggcagaaata agtatgcaag agccaaaatc attttatct     3180 gtgaagcaca taaccacctg gtgtaaccag tgtgcaaaat catgttgtat acctgattgt    3240
atgttgatgt ctttccatgc tgtatgtaat actatctgtc ttttgaggtt tttaaattca    3300
ataaggttaa tagccttaat ttaattatcc ttttatctcc ccttaaacgt cttgcttaat    3360
taattgaaac aataataata gatagttgga aagaaaagta atttctttga atattgtatt    3420 cattttttg gcagtatcac caaaaccctt gagaggtatc aacgctgttg cattaatcct     3480
caagacaatt gtggtgaaag agaaacacag gttaatttga aagcttcata ttttatgtgt    3540
ccagaaaaac ataataacaa tcaatcaaca ttggcttagt attatatcac aattagggtt    3600
gtactaactt taagttggaa aaaattgcta cttttatgat aatttattat ggttagttct    3660
tccaaatcat aatttatttt tgttgttgtt gtaaatttag agctggtacc aagaggtctc    3720
aaaattgaag gccaagttcg aagctcttca acgaactcaa aggttatgtc aattgcttat    3780
ttagacatga cttcttgaca tgcacatttt ttttttgta ctgcgtagat gtaacacact     3840
ctgaggttca gtaaagatat aaataatagt cgatcatata aaatgttaaa aggggagaga    3900
```

```
aatacaatat aatattcaca cacacacaca tatatatata tatatccttg aaagtgtgtt    3960
ataatacatg aaggcactta cttggtgaag atctggggac actaagtgtg aaggagttgc    4020
agaatcttga aaaacaactt gaaggtgcac ttgcacaagc tagacaaaga aaggtaccac    4080
tctattcaaa gaaaggaatt gccatctttt tatgattgtt acatacaata tgaaaaattt    4140
tattatgtgc ttcacacgat tggtattagt cgtatgagat ttcttttcgt ctcacaaaaa    4200
gtggatccaa gtcttatact tttaagtcca tgtacaaact ttggatcgat cctgctgtga    4260
gattaaaggg aatttcaaac gactagtgtc aattgtgtga gtcaaagtaa attgtttttt    4320
ccatacaata tgtagatttt ttttatttt tttttactt tggcactaaa catttgtttc      4380
ttcattgtgt agacccaaat aatgatggag cagatggagg agctccgcag aaaggtaaga    4440
tggaatatgc tgaatgaaga atattaatag tagtctatta ttttgaggt tctggtcgat     4500
cagtactaat taattggtac atatatatga tcattcttga ttatcacaac tataaatttg    4560
ttataattaa aaggttaatg gatgcaaaag aatggtgatt aatttagagt tggaagggat    4620
taaaatagta agaagatatg ttgtaaagag cagtacactg gaggaggatt atattgtaca    4680
gcttaatttg tacccattat aaaaggactt tctgaaccgg ccttttgatg tcttttgtg     4740
tcatgcatga tgagtgataa gtcacaacta cattgttggt gagacaagtc gatggataac    4800
ctttgatccg agacctcttt tattggaaaa aaaaatagtt aaatttgtga aaaagttatt    4860
tgttactcgc ctagtttctt ccgtccattc tcaagaaatt agttttcga aataccacct     4920
aaataactat gatcatagag tcaataagtt ggataaaaag agtctgatgt tggtccaatg    4980
tcatcataca ttgcatctta gtaaatttga tgcaagtgat ataacgaata tgaattcata    5040
aagttcacat tctaaacccg tctttggaga tatatatata cacaacaaca acaacaacaa    5100
acccagtgta ttcccactta gtggggtctg ggggggtaag atgtacgcag tccataccct    5160
tacctctgat gaagtagaaa ggctgtttcc gaaagacccc cggctcaggc acaagatatc    5220
acacaaacac atagtaaagc acagaagcag atgacaataa tataaataag gcacccatac    5280
ggactataaa acagaggaaa gcagaggaaa gcacacagat tcgtaataag catggaacac    5340
tgaatacgga atcataacag gaataaaaaa ataaaaaacc cccaccaagt aattccctac    5400
actagcgacc caatctggcc ctactcttct gccgtaattc gcctcttcca gaccatccta    5460
tctagggtca tgtcctcggt gagctgtttg gagatatata tatatggaca tatatttaat    5520
ctctctcatt atattgtgaa agctagcttt tgaattctga gtaattatct attttgacat    5580
gataatgatt atgttatcag gagcgtcatc ttggtgatgt gaacaagcag ctgaagatta    5640
aggtttccct tgaactatca tcggtactca ttcaacttga agaacgtaca ttactatgtt    5700
gcttagactc ttcgaaagta ccctcaaatg catgtctaat agcttatata tatatgagtg    5760
gaattacatt atatattttt gaagaatcca agcgacatag gactcttaag atgacatata    5820
tatatgttgc tacttctttg ttaagttcat atagaatagt tgcataaaca gtgaagagtt    5880
ttctttttct atttttggcag tttgagactg aaggacaagg actgagagct cttcctaatt    5940
ttccatggag ttgtaatgca tcagcagaag ctggaagcag ctcctttcat gtccaccatt    6000
ctcaatcaaa tcacatggat tgtgatcaac ctgatccagt tcttcaaata gggtatatat    6060
attgtaaata aacttcatct aattaccagt cgattgctcg tatggtcact caaccttggg    6120
taactggcta tcaaagtcat ctgttagaaa agggcagccc gggcactaa gctcccgccc     6180
gaccacaggg atccagcctc accttgtaac atcatgatga tctaaattgt aacaataatg    6240
tatcctgcag gtatcaacag tatatgtctg cagatggagc ctcagggtca aggagcaata    6300
```
tggcaattga gaacaacatc atccatggct ggggtctttg a        6341

<210> SEQ ID NO 5
<211> LENGTH: 768
<212> TYPE: DNA
<213> ORGANISM: Capsicum annuum
<220> FEATURE:
<221> NAME/KEY: misc_feature
<222> LOCATION: (1)..(810)
<223> OTHER INFORMATION: AGL6 coding sequence

<400> SEQUENCE: 5

```
atggggagag ggagagtgga actaaagaga atagagaaca aaatcaaccg tcaagtgacg      60
ttttctaaga ggaggaatgg tttgttgaag aaagcttatg aactttcagt gctttgtgat     120
gctgaagttg ctctcatcat cttctctggt cgcggaaaac tctatgagtt tggtaatgca     180
ggtatcacca aaacccttga gaggtatcaa cgctgttgca ttaatcctca agacaattgt     240
ggtgaaagag aaacacagag ctggtaccaa gaggtctcaa aattgaaggc caagttcgaa     300
gctcttcaac gaactcaaag gcacttactt ggtgaagatc tggggacact aagtgtgaag     360
gagttgcaga atcttgaaaa acaacttgaa ggtgcacttg cacaagctag acaaagaaag     420
acccaaataa tgatggagca gatggaggag ctccgcagaa aggagcgtca tcttggtgat     480
gtgaacaagc agctgaagat taaggtttcc cttgaactat catcgtttga gactgaagga     540
caaggactga gagctcttcc taattttcca tggagttgta atgcatcagc agaagctgga     600
agcagctcct ttcatgtcca ccattctcaa tcaaatcaca tggattgtga tcaacctgat     660
ccagttcttc aaataggata tcaacagtat atgtctgcag atggagcctc agggtcaagg     720
agcaatatgg caattgagaa caacatcatc catggctggg gtctttga               768
```

<210> SEQ ID NO 6
<211> LENGTH: 255
<212> TYPE: PRT
<213> ORGANISM: Capsicum annuum
<220> FEATURE:
<221> NAME/KEY: MISC_FEATURE
<222> LOCATION: (1)..(255)
<223> OTHER INFORMATION: AGL6 protein amino acid sequence

<400> SEQUENCE: 6

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Gly Arg Gly Lys Leu Tyr Glu Phe Gly Asn Ala Gly Ile Thr Lys
    50                  55                  60

Thr Leu Glu Arg Tyr Gln Arg Cys Cys Ile Asn Pro Gln Asp Asn Cys
65                  70                  75                  80

Gly Glu Arg Glu Thr Gln Ser Trp Tyr Gln Glu Val Ser Lys Leu Lys
                85                  90                  95

Ala Lys Phe Glu Ala Leu Gln Arg Thr Gln Arg His Leu Leu Gly Glu
            100                 105                 110

Asp Leu Gly Thr Leu Ser Val Lys Glu Leu Gln Asn Leu Glu Lys Gln
        115                 120                 125

Leu Glu Gly Ala Leu Ala Gln Ala Arg Gln Arg Lys Thr Gln Ile Met
    130                 135                 140
```

```
Met Glu Gln Met Glu Glu Leu Arg Arg Lys Glu Arg His Leu Gly Asp
145                 150                 155                 160

Val Asn Lys Gln Leu Lys Ile Lys Val Ser Leu Glu Leu Ser Ser Phe
            165                 170                 175

Glu Thr Glu Gly Gln Gly Leu Arg Ala Leu Pro Asn Phe Pro Trp Ser
        180                 185                 190

Cys Asn Ala Ser Ala Glu Ala Gly Ser Ser Ser Phe His Val His His
            195                 200                 205

Ser Gln Ser Asn His Met Asp Cys Asp Gln Pro Asp Pro Val Leu Gln
        210                 215                 220

Ile Gly Tyr Gln Gln Tyr Met Ser Ala Asp Gly Ala Ser Gly Ser Arg
225                 230                 235                 240

Ser Asn Met Ala Ile Glu Asn Asn Ile Ile His Gly Trp Gly Leu
            245                 250                 255
```

<210> SEQ ID NO 7
<211> LENGTH: 6321
<212> TYPE: DNA
<213> ORGANISM: Solanum melongena
<220> FEATURE:
<221> NAME/KEY: misc_feature
<222> LOCATION: (1)..(6321)
<223> OTHER INFORMATION: AGL6 gene sequence

<400> SEQUENCE: 7

```
atggggagag ggagagtgga actaaagaga atagagaaca aaatcaaccg tcaagtgaca     60
ttttctaaga ggaggaatgg tttgttgaag aaagcttatg aactatcagt tctttgtgat    120
gctgaagttg ctctcatcat cttctctggt cgtggaaagc tctatgagtt tggtagtgca    180
gggtatacac acatatatat actaactttt ttactttgtc tgggctctta atagctaatt    240
cttgttatgg ggttcttcta aatcataaaa agattacaac tttatgttat ggtgttacgt    300
tcatcatata tattactaag ctttttttcac acatggaaag tatgtcaagt ctactttgtg    360
gtgtgggctc ttaattaata gttgattctt gatatggggt tcttctaaat cacaaaaaga    420
ttacaacttt atggttttttt ttttccatat ggggttcatt atgtgtgtgt atatataaag    480
aaggataaac atacacagag gcaaagatag agtgaggtca gttgttgttt gtttatgtat    540
gagagtgggt tttaagtctc taattctaaa ttactctaaa aaaatatttt ttattatttt    600
ggggggggaag aaatagactt tgctaaattg gtatggactt ctgcagcact ttacacaagc    660
accaacttat gttgtttgtt aagtggagtt ttcagatttg gatctctctt gagttttctt    720
tcttctctca gtttaatgtt tgatcaaaat ttgatgaaat gagaaggggc tttgtgtttt    780
accaatggga aattgacacg tttcaatggt ttttgagct ttctaatcta caaatacaaa    840
aagatcagag taaggactga ccaggtctag aaacttcttc ctcttccaac cctttttggac    900
aaatgtgtaa gatctagggt ttctctccat tttgttccta ctattccctt tcatcttttt    960
ctttaatgct tttggagttt cttggagcac ttcttagtcc aatggttcta aaacatcatg   1020
aagttccaaa ctttgtcttc tttataccctt ttcatcctta aatcttgagg tcctttcact   1080
gaattctacc aaacctcata cattttcatc ttttgttacc aaatcctttg tgtaaaagag   1140
ggtattgtac tgcactgcac atcaaaaaag tattggcata tgcctgtgaa aagggaaatt   1200
ttttcatata tgagaatttt ggcatttatt agttttgcag gtaagtatat gatctgattg   1260
caacttctca tatatgtata agagaaagga gttttcttta tcagttccca aacccccaaga   1320
actgattaag atctctttttt tcttcccatt ttggtgaaac ttattactga tgagccttag   1380
```

```
tagattcttg agttttttcaa tatgtattag aaattttgct tccatttcat gttctttaat    1440
gtgaacaagt gcgtagctgt gaaaatgagt acttttattt ctataacact gtgcaggttc    1500
aaaaaaaaat tttcatccct tgttcatgc ttttttttcc tcttcaggtt ttctttgcta     1560
gtgttatata tgtacatact ttcttttttca tatactttt ttttgacatc attgctttgt    1620
tcttgttttg ttgaagaatg attgtattaa agaaaaattg ctcctttgtt tttggtaata    1680
tctctgactt tttgactcat acaaatcatc taggggtaag agcataatgt tgaagaggac    1740
ttctcttttg cattttttt gttatctttc aagaaaataa caagaaaaga tgtagtggcc     1800
aattacaaaa ttcttgtctt cttaatcaga tttgtactac cacatgtagc acttttgttt    1860
tgcattaggg ttttgtgcgg agaaatgtga tctttgttat tatagacaaa aagaaatat     1920
taatcagtgg ttttgaattc ttgaattgta ctcgtatcat attcattgtt cactttttc     1980
tttacacgcc tgaaatcaaa aggaaaggtt ggaagaagga aaagttatga gcccttccac    2040
tttaatttct ccgtactaat atgggataga gagagtaata aaaaaaatcta tagagtcctc   2100
aattcaatgt ctaaatggtt ttgtgtatat tctacttatc cttaaggaat tgccaaaatg    2160
aatttcttt accacgttta tttggtttag tctttttttcc acttttccaaa tatggaagtt   2220
tggaagaagg aaaaagacaa catcttgcta tactagtgga caattacata caatgatgca   2280
aatgaataga aatgagaaga cttttgctat tttaatcttt gtgcactctt tcgacttta    2340
tctttattgc ttttttaattt tactgcatga ccccttttta gcccattgta tatcatataa   2400
cttctttttc ttttgaagtt tgtttctttg ctcttgtgtt ttttttttc ttttttggatt   2460
tgggatggaa tgaatggtta attaagcctt ctttttttat gattaggtgt gtgattattt    2520
tttttattat ttggtgatag tacgattcaa attagaaatt ttttctatgc tctgatatca    2580
tgttaatgtt tataaactat ccgatctcaa acttaaccat taaacataat aggagtagct    2640
taaacatagt ggaaattaaa cttggtatgg gcttcatttc catacacatg cattgttcat    2700
agtactcact atgtttcaat ttatttgttt tattgttttt aaatctaatt aaaaatgaat    2760
ctttctttt taagtaactc tttaatttaa tttttcatat gacttaaaaa ttacaaagtt    2820
aaagaacagt taggtacatt ctgtatattt ttagtttata accataaagt taaaaatctt    2880
ctttattatt ttaaatttca tgttaagtaa aagccaaaat taaagaacaa ttaggtacat    2940
tatgtatatt tttagtttat aaccataaag ttaaaaatct tctttattat tttaaatttc    3000
atgttaagta aaagccaaaa ttaaagaacg gttaggtaca ttctgtatat ttttagttta    3060
taaccataaa gttaaaaatc ttctttatta ttttaaattt catgttaagt aaaagccaaa    3120
attaaagaac agttaggtac attatgtata tttttagttt atgaccacaa agttaaaaat    3180
cttctttatt attttaaatt tcatgttaag tcaaagccaa acaagcaaat taaatgagag    3240
tgtaataagt ttacgagcgc caaaaattca atttttttgt gaagcacaaa aggaatcccc    3300
ttgtatgacc tttgtgcaaa atcatgttct acacataatt gtatgttgtt gtctttccat    3360
gttttatgta attctatctg tcttttgagg tttttacaca caaaaaagaa ttatttatcc    3420
tcctaaatca gtagagcatt tgtctaatta attatattct ctcttcttaa acgtctcact    3480
taattcattg caataataag aacaagattt gtaagaaaaa gtaaactttt gaatgttgtg    3540
tttgttttgt tggcagaatc acgaaaaccc ttgagagata ccaacgttgt tgccttaatc    3600
ctcaagacaa ttatggtgaa agagaaacac aggtttgtag cttcttattc ttttacatgt    3660
ttttttttgg taaataaaag atattatatt aacttagtaa tatgcttcag tacaaggtag    3720
```

-continued

```
ttacgtatac aaaatctggg ctatactgcc cgggggagg gggattaca aaagcttta      3780
tcaatattga tctcttcttt acatgttaat tatgtttcca aaaaatcaat caattggcta   3840
attattatta ttcacagttt tagagttta ctaactttaa gttattattt agcatgcata    3900
atttgttttt ctggttgttg taaatttaga gctggtacca agaagtctca aaattgaagg   3960
ccaaattcga agcccttcaa cgaactcaaa ggttaattat gtcaattgac aatattataa   4020
ttttgagata tatatatgtg tgtgtgtgaa gttttttgta tatttttaa aatttgtttg    4080
gtaatacata tgaaggcatt tacttggtga agatcttggg gcactaagtg tgaaggagtt   4140
gcaaaatctt gaaaaacaac ttgaaggtgc acttgcacaa gctaggcaaa gaaaggtact   4200
ctattgtttt tcaattttat tacgcgcttc acgcaattga tattagttgg acgaggcttt   4260
tctttacatc acaaaaaaag attatgaggt ccacaaactt cgatctacct ttttttttgtg  4320
tgtgaaataa aaaggaattt caacaattgt gcgaatgaaa aatttaactt ttgtccgtag   4380
gataggtata aattttactt ttggtactac ttatgcattg gttgctgcat tgtgtagaca   4440
cagataatga cggaacagat ggaggagctt cgtaaaaagg taagatataa ttgtcatttt   4500
tgactatcac aattatgaat ttgttataaa aggtaaatgg atgattaatt aagagttgga   4560
agggatttga atcttaagaa aatatgttat aaagaatagt acactacagg agggctgtac   4620
agttcaattt gtactcatta taaaggactt ggtgagcctt tgatgtctt tttgtgtcat    4680
gcatggtgac tgatcataag tcccaactat attgttgtga cagcaccttt tccatttagt   4740
tgatgacacc tattttcagg tcgataaagt ttgatccaat acctctttta attaaacaaa   4800
taataattat atttgctaaa tggaagcctt tgaaactagc tatacgaaat accacctaaa   4860
taactatggt cctagagtca aataagttgc actgaaagag ttgaaggtgg gtccaatgac   4920
atatcatact ttttggtaat tggacatgaa tttaattgtg tcacggtacc atcaacgtct   4980
cgattgaaac tctgtaaatg taacatctag attaacaact ggtaaagctc aattttcctt   5040
ttacctagaa tggaacctct tctaactaaa tacttaactg caccaagtag acatgacttt   5100
atcttgtgct aaaaattgct aagaaatatc aaattgttat aaatatatt gtgttgcagt    5160
gaatgtttat tacgtaagtt ttttggagaa aatttaggaa ctctaactta aggagcaagt   5220
caggtttcct ctatagataa aggagtttc cttccttgta ataaatatta ttcgagagaa    5280
ctcagaattc ttcttctc tccctacttt cttcttgttc ttactttata ctttcataac    5340
acaaatatag ttttactctg tgaatatttg acatcacttt cctaaaatgc cgtgacaacc   5400
aaagctttca aattttgaat ccgctaaatc tttctcattt tcaatgagct agtgaattcc   5460
aagctgataa ggtaggtgac gaacaacaat tgatactaga aaaaaaaag aacaacattc    5520
ttaattatca actttgacat gataattgtt atgttatata tcaggagcgt catcttggtg   5580
atgtaaacaa gcagctgaag attaaggttt ctctaggact atcaacggta ctcattcaac   5640
ttgaacacag tactatgttg ttgaaacttt tcaaaaatat taacaatgcg atgatatttt   5700
tggagaattc caacaacatt agatctatgt aacaatattg cttttgaata gtttgttttt   5760
tgtatgtttg cagttggagt ctgaaggaca agatggactg agaggtcttc cttttccatg   5820
gagttgtaat gcatcagcag aagctggaag tagcaccttt catgttcacc attctcaatc   5880
aaatcacatg gattgtgatc aacctgatcc agttcttcaa atagggtatt cctacatctc   5940
caccttcttc gtttagagca tgagacacgc gctaaacgaa ttatatttga tatttaagtg   6000
cagaaagtta gacgggcata cctattatac ctaaattttg aacattaaca tttgattcct   6060
catgatgaaa tttctcgatc ataaataaat tatattacct atctcgaaaa aaaatgtggt   6120
```

```
agtaatattg tgaagtttct tttctttctc gcctaaatat tgagttgatc ttatccaatt    6180
gagggggaag ggtactttaa tttgcatgat cttcatgatg tatataccct caggtatcat    6240
gagtatatgg cagcagatgg agcctcaggg tcaaggagca tggctattga gagcaacatc    6300
atccatggct ggggtctttg a                                              6321
```

<210> SEQ ID NO 8
<211> LENGTH: 744
<212> TYPE: DNA
<213> ORGANISM: Solanum melongena
<220> FEATURE:
<221> NAME/KEY: misc_feature
<222> LOCATION: (1)..(744)
<223> OTHER INFORMATION: AGL6 coding sequence

<400> SEQUENCE: 8

```
atggggagag ggagagtgga actaaagaga atagagaaca aaatcaaccg tcaagtgaca     60
ttttctaaga ggaggaatgg tttgttgaag aaagcttatg aactatcagt tctttgtgat    120
gctgaagttg ctctcatcat cttctctggt cgtggaaagc tctatgagtt tggtagtgca    180
ggaatcacga aaacccttga gagataccaa cgttgttgcc ttaatcctca agacaattat    240
ggtgaaagag aaacacagag ctggtaccaa gaagtctcaa aattgaaggc caaattcgaa    300
gcccttcaac gaactcaaag gcatttactt ggtgaagatc ttggggcact aagtgtgaag    360
gagttgcaaa atcttgaaaa acaacttgaa ggtgcacttg cacaagctag gcaaagaaag    420
acacagataa tgacggaaca gatggaggag cttcgtaaaa aggagcgtca tcttggtgat    480
gtaaacaagc agctgaagat taagttggag tctgaaggac aagatggact gagaggtctt    540 cctttttccat ggagttgtaa tgcatcagca gaagctggaa gtagcacctt tcatgttcac    600
cattctcaat caaatcacat ggattgtgat caacctgatc cagttcttca aatagggtat    660
catgagtata tggcagcaga tggagcctca gggtcaagga gcatggctat tgagagcaac    720
atcatccatg gctggggtct ttga                                           744
```

<210> SEQ ID NO 9
<211> LENGTH: 247
<212> TYPE: PRT
<213> ORGANISM: Solanum melongena
<220> FEATURE:
<221> NAME/KEY: MISC_FEATURE
<222> LOCATION: (1)..(247)
<223> OTHER INFORMATION: AGL6 protein amino acid sequence

<400> SEQUENCE: 9

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Gly Arg Gly Lys Leu Tyr Glu Phe Gly Ser Ala Gly Ile Thr Lys
    50                  55                  60

Thr Leu Glu Arg Tyr Gln Arg Cys Cys Leu Asn Pro Gln Asp Asn Tyr
65                  70                  75                  80

Gly Glu Arg Glu Thr Gln Ser Trp Tyr Gln Glu Val Ser Lys Leu Lys
                85                  90                  95

Ala Lys Phe Glu Ala Leu Gln Arg Thr Gln Arg His Leu Leu Gly Glu
            100                 105                 110
```

```
Asp Leu Gly Ala Leu Ser Val Lys Glu Leu Gln Asn Leu Glu Lys Gln
            115                 120                 125

Leu Glu Gly Ala Leu Ala Gln Ala Arg Gln Arg Lys Thr Gln Ile Met
        130                 135                 140

Thr Glu Gln Met Glu Glu Leu Arg Lys Lys Glu Arg His Leu Gly Asp
145                 150                 155                 160

Val Asn Lys Gln Leu Lys Ile Lys Leu Glu Ser Glu Gly Gln Asp Gly
                165                 170                 175

Leu Arg Gly Leu Pro Phe Pro Trp Ser Cys Asn Ala Ser Ala Glu Ala
            180                 185                 190

Gly Ser Ser Thr Phe His Val His Ser Gln Ser Asn His Met Asp
        195                 200                 205

Cys Asp Gln Pro Asp Pro Val Leu Gln Ile Gly Tyr His Glu Tyr Met
210                 215                 220

Ala Ala Asp Gly Ala Ser Gly Ser Arg Ser Met Ala Ile Glu Ser Asn
225                 230                 235                 240

Ile Ile His Gly Trp Gly Leu
            245

<210> SEQ ID NO 10
<211> LENGTH: 61
<212> TYPE: DNA
<213> ORGANISM: Artificial Sequence
<220> FEATURE:
<223> OTHER INFORMATION: Single strand DNA oligonucleotide

<400> SEQUENCE: 10
agagtcgaca tagcgattga ggattaaggc aacaacgtgt tttagagcta gaaatagcaa      60
g                                                                     61

<210> SEQ ID NO 11
<211> LENGTH: 34
<212> TYPE: DNA
<213> ORGANISM: Artificial Sequence
<220> FEATURE:
<223> OTHER INFORMATION: Single strand DNA oligonucleotide

<400> SEQUENCE: 11
taagctaagc ttcgatctaa aaaaagcacc gact                                  34

<210> SEQ ID NO 12
<211> LENGTH: 6
<212> TYPE: DNA
<213> ORGANISM: Artificial Sequence
<220> FEATURE:
<223> OTHER INFORMATION: AclI restriction enzyme site

<400> SEQUENCE: 12 aacgtt                                                                 6

<210> SEQ ID NO 13
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 13
gccttgaaat cagtaagagt attgg                                            25
```

-continued

```
<210> SEQ ID NO 14
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 14
gttcgttgaa gtgcttcaaa cttgg                                          25

<210> SEQ ID NO 15
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 15
cgacaatctg atccaagctc a                                              21

<210> SEQ ID NO 16
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 16
cgacaatctg atccaagctc a                                              21

<210> SEQ ID NO 17
<211> LENGTH: 20
<212> TYPE: DNA
<213> ORGANISM: Artificial Sequence
<220> FEATURE:
<223> OTHER INFORMATION: Exemplary sequences that can be used as target
      for CRISPR based gene editing in the Capana01g00134 gene

<400> SEQUENCE: 17
gtatcaccaa aacccttgag                                                20

<210> SEQ ID NO 18
<211> LENGTH: 20
<212> TYPE: DNA
<213> ORGANISM: Artificial Sequence
<220> FEATURE:
<223> OTHER INFORMATION: Exemplary sequences that can be used as target
      for CRISPR based gene editing  in the Sme2.5_06058.1 gene

<400> SEQUENCE: 18
gaggattaag gcaacaacgt                                                20

<210> SEQ ID NO 19
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 19
cgacaatctg atccaagctc a                                              21

<210> SEQ ID NO 20
<211> LENGTH: 20
<212> TYPE: DNA
<213> ORGANISM: Artificial Sequence
<220> FEATURE:
```

<223> OTHER INFORMATION: Single strand DNA oligonucleotide

<400> SEQUENCE: 20
gacactgacg gctttatgcc                                                    20

<210> SEQ ID NO 21
<211> LENGTH: 252
<212> TYPE: PRT
<213> ORGANISM: Artificial Sequence
<220> FEATURE:
<223> OTHER INFORMATION: protein sequence of the MADS box protein SlAGL6

<400> SEQUENCE: 21

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Glu Ala Glu Val Ala Leu Ile Ile Phe
        35                  40                  45

Ser Ser Arg Gly Lys Leu Tyr Glu Phe Gly Ser Ala Gly Ile Thr Lys
    50                  55                  60

Thr Leu Glu Arg Tyr Gln Arg Cys Cys Leu Asn Pro Gln Asp Asn Cys
65                  70                  75                  80

Gly Glu Arg Glu Thr Gln Ser Trp Tyr Gln Glu Val Ser Lys Leu Lys
                85                  90                  95

Ala Lys Phe Glu Ala Leu Gln Arg Thr Gln Arg His Leu Leu Gly Glu
            100                 105                 110

Asp Leu Gly Ala Leu Ser Val Lys Glu Leu Gln Asn Leu Glu Lys Gln
        115                 120                 125

Leu Glu Gly Ala Leu Ala Gln Ala Arg Gln Arg Lys Thr Gln Ile Met
    130                 135                 140

Met Glu Gln Met Glu Glu Leu Arg Arg Lys Glu Arg His Leu Gly Asp
145                 150                 155                 160

Val Asn Lys Gln Leu Lys Ile Lys Val Ser Leu Glu Leu Ser Ser Phe
                165                 170                 175

Glu Gly Glu Gly Gln Val Pro Phe Pro Trp Ser Asn Cys Asn Ala
            180                 185                 190

Ser Leu Asp Glu Ala Gly Ser Ser Thr Phe His Val His His Ser Gln
        195                 200                 205

Ser Asn His Met Asp Cys Asp Leu Pro Asp Pro Val Leu Gln Ile Gly
    210                 215                 220

Tyr His Gln Tyr Met Ala Ala Asp Gly Ala Ser Gly Ser Arg Asn Met
225                 230                 235                 240

Ala Val Glu Ser Asn Ile Ile His Gly Trp Gly Leu
                245                 250

<210> SEQ ID NO 22
<211> LENGTH: 382
<212> TYPE: PRT
<213> ORGANISM: Artificial Sequence
<220> FEATURE:
<223> OTHER INFORMATION: ORF of SlAGL6

<400> SEQUENCE: 22

Ala Thr Gly Gly Gly Ala Gly Ala Gly Gly Ala Gly Ala Gly
1               5                   10                  15

Thr Gly Gly Ala Ala Cys Thr Ala Ala Ala Gly Ala Gly Ala Ala Thr
            20                  25                  30

```
Ala Gly Ala Gly Ala Ala Cys Ala Ala Ala Thr Cys Ala Ala Cys
        35                  40                  45
Cys Gly Thr Cys Ala Ala Gly Thr Gly Ala Cys Ala Thr Thr Thr
    50                  55                  60
Cys Thr Ala Ala Gly Ala Gly Gly Ala Gly Ala Ala Thr Gly Gly
65                  70                  75                  80
Thr Thr Thr Gly Thr Thr Gly Ala Ala Gly Ala Ala Gly Cys Thr
                85                  90                  95
Thr Ala Thr Gly Ala Ala Thr Thr Ala Thr Cys Ala Gly Thr Gly Cys
            100                 105                 110
Thr Thr Thr Gly Thr Gly Ala Gly Gly Cys Thr Gly Ala Ala Gly Thr
            115                 120                 125
Thr Gly Cys Thr Cys Thr Cys Ala Thr Cys Ala Thr Cys Thr Thr Cys
            130                 135                 140
Thr Cys Thr Ala Gly Thr Cys Gly Thr Gly Gly Ala Ala Ala Gly Cys
145                 150                 155                 160
Thr Cys Thr Ala Thr Gly Ala Gly Thr Thr Thr Gly Gly Thr Ala Gly
                165                 170                 175
Thr Gly Cys Ala Gly Gly Thr Ala Thr Cys Ala Cys Thr Ala Ala Ala
                180                 185                 190
Ala Cys Cys Cys Thr Thr Gly Ala Gly Ala Gly Gly Thr Ala Cys Cys
            195                 200                 205
Ala Ala Cys Thr Thr Gly Thr Thr Gly Cys Cys Thr Thr Ala Ala Thr
            210                 215                 220
Cys Cys Thr Cys Thr Ala Ala Gly Ala Cys Ala Ala Thr Thr Gly Thr Gly
225                 230                 235                 240
Gly Thr Gly Ala Ala Ala Gly Ala Gly Ala

Arg Gln Val Thr Phe Ser Lys Arg Asn Gly Leu Leu Lys Lys Ala
            20                  25                  30

Tyr Glu Leu Ser Val Leu Cys Glu Ala Glu Val Ala Leu Ile Ile Phe
        35                  40                  45

Ser Ser Arg Gly Lys Leu Tyr Glu Phe Gly Ser Ala Gly Ile Thr Lys
50                  55                  60

Thr Leu Glu Arg Tyr Gln Arg Cys Cys Leu Asn Pro Gln Asp Asn Cys
65                  70                  75                  80

Gly Glu Arg Glu Thr Gln Ser Trp Tyr Gln Glu Val Ser Lys Leu Lys
                85                  90                  95

Ala Lys Phe Glu
            100

<210> SEQ ID NO 24
<211> LENGTH: 89
<212> TYPE: PRT
<213> ORGANISM: Artificial Sequence
<220> FEATURE:
<223> OTHER INFORMATION: mutated AGL6  partial amino acid sequence

<400> SEQUENCE: 24

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Glu Ala Glu Val Ala Leu Ile Ile Phe
        35                  40                  45

Ser Ser Arg Gly Lys Leu Tyr Glu Phe Gly Ser Ala Gly Ile Thr Lys
50                  55                  60

Thr Leu Glu Arg Tyr Gln Arg Cys Cys Leu Asn Pro Gln Asp Asn Cys
65                  70                  75                  80

Gly Glu Arg Glu Thr Gln Ser Trp Tyr
                85

<210> SEQ ID NO 25
<211> LENGTH: 74
<212> TYPE: PRT
<213> ORGANISM: Artificial Sequence
<220> FEATURE:
<223> OTHER INFORMATION: mutated AGL6  partial amino acid sequence

<400> SEQUENCE: 25

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Glu Ala Glu Val Ala Leu Ile Ile Phe
        35                  40                  45

Ser Ser Arg Gly Lys Leu Tyr Glu Phe Gly Ser Ala Gly Ile Thr Lys
        50                  55                  60

Thr Leu Glu Arg Tyr Gln Arg Leu Leu Pro
65                  70

<210> SEQ ID NO 26
<211> LENGTH: 94
<212> TYPE: PRT
<213> ORGANISM: Artificial Sequence
<220> FEATURE:
<223> OTHER INFORMATION: mutated AGL6  partial amino acid sequence

<400> SEQUENCE: 26

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Glu Ala Glu Val Ala Leu Ile Ile Phe
            35                  40                  45

Ser Ser Arg Gly Lys Leu Tyr Glu Phe Gly Ser Ala Gly Ile Thr Lys
    50                  55                  60

Thr Leu Glu Arg Tyr Gln Arg Val Ala Leu Ile Leu Lys Thr Ile Val
65                  70                  75                  80

Val Lys Glu Lys His Arg Ala Gly Thr Lys Arg Ser Leu Asn
                85                  90

<210> SEQ ID NO 27
<211> LENGTH: 67
<212> TYPE: PRT
<213> ORGANISM: Artificial Sequence
<220> FEATURE:
<223> OTHER INFORMATION: mutated AGL6  partial amino acid sequence

<400> SEQUENCE: 27

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Glu Ala Glu Val Ala Leu Ile Ile Phe
            35                  40                  45

Ser Ser Arg Gly Lys Leu Tyr Glu Phe Gly Ser Ala Glu Leu Val Pro
    50                  55                  60

Arg Gly Leu
65

<210> SEQ ID NO 28
<211> LENGTH: 88
<212> TYPE: PRT
<213> ORGANISM: Artificial Sequence
<220> FEATURE:
<223> OTHER INFORMATION: mutated AGL6  partial amino acid sequence

<400> SEQUENCE: 28

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Glu Ala Glu Val Ala Leu Ile Ile Phe
            35                  40                  45

Ser Ser Arg Gly Lys Leu Tyr Glu Phe Gly Ser Ala Gly Tyr Ile His
    50                  55                  60

Thr Tyr Ile Tyr Tyr Leu Phe Phe Leu Tyr Ile Tyr Met Lys Asn Val
65                  70                  75                  80

Ser Ser Leu Leu Cys Met Gly Ser
                85

What is claimed is:

1. A tomato plant exhibiting a facultative parthenocarpy having a loss-of-function mutation in a homozygous form in a coding sequence of SlAGAMOUS-LIKE 6 (SlAGL6) gene, wherein said plant further exhibits (i) for fruits selected weighing minimum 8 grams each a fruit yield/plant at least about the same as that of a seed-bearing, non-parthenocarpic tomato of the same genetic background when grown together under identical conditions, wherein said about is defined as ±10%, and (ii) an average fruit weight/plant at least about the same as that of a seed-bearing, non-parthenocarpic tomato of the same genetic background when grown together under identical conditions, wherein said about is defined as ±10%, and wherein said loss of function mutation comprises (I) a mutation comprising a 175 nucleotide deletion, comprising the last 98 nucleotides of intron 1, all of exon 2 (76 nucleotides), and the first nucleotide of intron 2, or (II) a $C_{268}/t$ mutation in said SlAGL6 gene, said mutation resulting in a premature stop codon in said coding sequence.

2. The plant of claim 1, further exhibiting at least one of:

(i) comprising jelly fill; and (ii) enlarged ovules within the seedless fruits developed from non-fertilized ovaries.

3. The plant of claim 1, wherein said tomato is selected from the group consisting of a single fruit per truss, branched tomato and cherry tomato.

4. The plant of claim 1, wherein said facultative parthenocarpy is manifested under heat or cold stress.

5. The plant of claim 1 being an inbred.

6. A fruit of the plant of claim 1.

7. A seed of the plant of claim 1.

8. The seed of claim 7 being a hybrid seed.

9. An edible processed product of the plant of claim 1 comprising genomic DNA of the plant and wherein the edible processed product is selected from the group consisting of a tomato paste, a ketchup, a tomato sauce, a tomato soup, a tomato juice, a tomato powder, a tomato dice, a crushed tomato, a chopped tomato and a tomato concentrate.

10. A method of producing the mutant plant of claim 1, the method comprising:

i) carrying out gene editing on the endogenous AGL6 gene of a tomato plant, ii) selecting a mutant plant comprising the mutation in part I or the mutation in part II of claim 1, iii) allowing the selected plant to self-pollinate, and iv) selecting a plant that is homozygous for the mutation; whereby, the selected homozygous mutant plant has a loss of function of the AGL6 gene.

11. A method of breeding comprising selfing or crossing the plant of claim 1.

* * * * *

UNITED STATES PATENT AND TRADEMARK OFFICE
CERTIFICATE OF CORRECTION

| | | |
|---|---|---|
| PATENT NO. | : 11,839,195 B2 | |
| APPLICATION NO. | : 16/071097 | |
| DATED | : December 12, 2023 | |
| INVENTOR(S) | : Rivka Barg et al. | |

It is certified that error appears in the above-identified patent and that said Letters Patent is hereby corrected as shown below:

On the Title Page

In item (71) Applicant, Line 1:
"Isreal" should be changed to --Israel--

Signed and Sealed this
Fourth Day of June, 2024

Katherine Kelly Vidal
*Director of the United States Patent and Trademark Office*